(12) United States Patent
Claiborne et al.

(10) Patent No.: US 7,211,595 B2
(45) Date of Patent: May 1, 2007

(54) FARNESYLTRANSFERASE INHIBITORS

(75) Inventors: Akiyo K. Claiborne, Mundelein, IL (US); Stephen L. Gwaltney, II, Lindenhurst, IL (US); Lisa A. Hasvold, Grayslake, IL (US); Qun Li, Libertyville, IL (US); Tongmei Li, Waukegan, IL (US); Nan-Horng Lin, Vernon Hills, IL (US); Robert A. Mantei, Franklin, WI (US); Todd W. Rockway, Grayslake, IL (US); Hing L. Sham, Vernon Hills, IL (US); Gerard M. Sullivan, Round Lake Beach, IL (US); Yunsong Tong, Grayslake, IL (US); Gary Wang, Niles, IL (US); Le Wang, Mundelein, IL (US); Xilu Wang, Skokie, IL (US); Wei-Bo Wang, Grayslake, IL (US)

(73) Assignee: Abbott Laboratories, Abbott Park, IL (US)

( * ) Notice: Subject to any disclaimer, the term of this patent is extended or adjusted under 35 U.S.C. 154(b) by 149 days.

(21) Appl. No.: 09/997,323

(22) Filed: Nov. 30, 2001

(65) Prior Publication Data

US 2003/0087940 A1 May 8, 2003

Related U.S. Application Data

(60) Provisional application No. 60/307,798, filed on Jul. 25, 2001, and provisional application No. 60/250,207, filed on Nov. 30, 2000.

(51) Int. Cl.
| | |
|---|---|
| *A61K 31/415* | (2006.01) |
| *C07D 401/04* | (2006.01) |
| *C07D 401/12* | (2006.01) |
| *C07D 233/32* | (2006.01) |

(52) U.S. Cl. .................. 514/396; 514/397; 514/336; 546/173; 546/268.4; 546/272.1; 548/346.1

(58) Field of Classification Search .............. 548/346.1; 514/396, 397; 546/152, 173, 268.1, 268.4, 546/272.7

See application file for complete search history.

(56) References Cited

U.S. PATENT DOCUMENTS

| 5,030,644 A | * | 7/1991 | Baldwin et al. ............ 514/393 |
| 5,245,061 A | | 9/1993 | Singh |
| 5,624,947 A | * | 4/1997 | Keown et al. ............... 514/392 |
| 5,714,479 A | * | 2/1998 | Ishikawa et al. ............... 514/80 |
| 5,854,264 A | | 12/1998 | Anthony et al. |
| 5,854,265 A | | 12/1998 | Anthony |
| 5,859,035 A | | 1/1999 | Anthony et al. |
| 5,872,136 A | | 2/1999 | Anthony et al. |
| 5,874,452 A | | 2/1999 | Anthony |
| 5,880,140 A | | 3/1999 | Anthony |
| 5,883,105 A | | 3/1999 | Anthony |
| 5,939,557 A | | 8/1999 | Anthony et al. |
| 6,080,870 A | | 6/2000 | Anthony |
| 6,143,766 A | * | 11/2000 | Kaltenbronn et al. ....... 514/312 |

FOREIGN PATENT DOCUMENTS

| WO | 97/36875 | 10/1997 |
| WO | 97/36876 | 10/1997 |
| WO | 97/36881 | 10/1997 |
| WO | 97/36897 | 10/1997 |
| WO | 97/36901 | 10/1997 |
| WO | 99/17777 | 4/1999 |
| WO | 99/18096 | 4/1999 |
| WO | 99/20609 | 4/1999 |
| WO | 99/27928 | 6/1999 |
| WO | 99/27929 | 6/1999 |
| WO | 99/27933 | 6/1999 |
| WO | 99/28313 | 6/1999 |
| WO | 99/28314 | 6/1999 |
| WO | 00/12498 | 3/2000 |

OTHER PUBLICATIONS

Caplus Abstract DN 114:42649 Brian Phillips et al 1990.*
Goldstein, J.L. et al., "Nonfarnesylated Tetrapeptide Inhibitors of Protein Farnesyltransferase," Journal of Biological Chemistry 266(24):15575–15578 (1991).
IUPAC, IUPAC "Commission on Nomenclature of Organic Chemistry, Rules for the Nomenclature of Organic Chemistry," 45:13–30 (1976).
Moores, S.L. et al., "Sequence Dependence of Protein Isoprenylation," Journal of Biological Chemistry 266(22):14603–14610 (1991).
Reiss, Y. et al., "Inhibition of Purified p21$^{ras}$ Farnesyl:Protein Transferase by Cys–AAX Tetrapeptides," Cell 62:81–88 (1990).
Vogt, A. et al., "Non–Peptide Mimetic of Ras–CAAX: Selective Inhibition of Farnesyltransferase and Ras Processing," Journal of Biological Chemistry 270(2):660–664 (1995).

* cited by examiner

*Primary Examiner*—Rita Desai
(74) *Attorney, Agent, or Firm*—Johanna M. Corbin; Gregory W. Steele

(57) ABSTRACT

Substituted imidazoles and thiazoles having the formula (I)

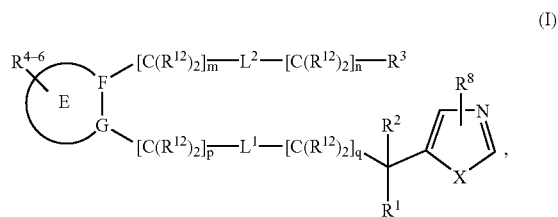

are useful for inhibiting farnesyltransferase. Also disclosed are farnesyltransferase-inhibiting compositions and methods of inhibiting farnesyltransferase in a patient.

34 Claims, No Drawings

FARNESYLTRANSFERASE INHIBITORS

CROSS-REFERENCE TO RELATED APPLICATIONS

This application claims priority to U.S. provisional application Ser. Nos. 60/307,798, which was filed Jul. 25, 2001 and 60/250,207, which was filed Nov. 30, 2000.

TECHNICAL FIELD

The present invention provides substituted imidazoles and thiazoles which inhibit farnesyltransferase, methods for making the compounds, pharmaceutical compositions containing the compounds, and methods of treatment using the compounds.

BACKGROUND OF THE INVENTION

Ras oncogenes are the most frequently identified activated oncogenes in human tumors, and transformed protein Ras is involved in the proliferation of cancer cells. The Ras must be farnesylated by farnesyl pyrophosphate before this proliferation can occur, and farnesylation of Ras by farnesyl pyrophosphate is effected by protein farnesyltransferase. Inhibition of protein farnesyltransferase, and thereby farnesylation of the Ras protein, blocks the ability of transformed cells to proliferate.

Activation of Ras and related proteins which are farnesylated also partially mediates smooth muscle cell proliferation (*Circulation*, I-3:88 (1993)). Inhibition of protein isoprenyl transferases, and thereby farnesylation of the Ras protein, also aids in the prevention of intimal hyperplasia associated with restenosis and atherosclerosis, a condition which compromises the success of angioplasty and surgical bypass for obstructive vascular lesions.

Because of the pivotal role played by farnesyltransferase in tumor formation and metastasis, compounds such as those reported in WO 97/36897, WO 97/36881, WO 97/36875, WO 97/36901, WO 99/17777, WO 99/18096, WO 99/20609, WO 99/27928, WO 99/27933, WO 99/27929, WO 99/28313, WO 99/28314, U.S. Pat. Nos. 5,872,136, and 5,939,557 have been the subject of current research. However, there is still an ongoing need for farnesyltransferase inhibitors with modified or improved profiles of activity.

SUMMARY OF THE INVENTION

In its principle embodiment, the present invention provides a farnesyltransferase inhibitor of formula (I)

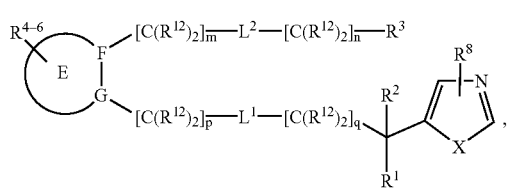

(I)

or a therapeutically acceptable salt thereof, wherein

E is a five-, six-, or seven-membered aromatic or non-aromatic carbocyclic ring wherein from zero to three carbon atoms are replaced by nitrogen;

F and G are independently selected from the group consisting of C and N; with the proviso that when one of F and G is N, the other is C;

$L^1$ and $L^2$ are each independently selected from the group consisting of a bond, $C_2$ alkenylene, $C_2$ alkynylene, O, $NR^9$, C(O), S, S(O), $SO_2$, $SO_2NR^9$, $NR^9SO_2$, $C(O)NR^9$, $NR^9C(O)$, and $CO_2$;

X is selected from the group consisting of S and $NR^7$;

$R^1$ is selected from the group consisting of aryl, arylalkyl, heterocycle, and (heterocycle)alkyl;

$R^2$ is selected from the group consisting of hydrogen, alkoxy, alkyl, amino, aminoalkyl, cyano, cyanoalkyl, cycloalkyl, cycloalkylalkyl, halo, haloalkyl, heterocycle, (heterocycle)alkyl, hydroxy, and hydroxyalkyl;

$R^3$ is selected from the group consisting of aryl, heterocycle, and cycloalkyl;

$R^{4-6}$ are each independently selected from the group consisting of hydrogen, $NR^9C(O)$, $C(O)NR^9$, alkanoyl, alkenyl, alkoxy, alkoxyalkyl, alkyl, alkylsulfonyl, alkynyl, amido, amino, aminoalkyl, aminosulfonyl, aryl, arylalkyl, aryloxy, arylsulfonyl, azido, carboxy, cyano, cyanoalkyl, cycloalkyl, cycloalkylalkyl, halo, haloalkoxy, haloalkyl, heterocycle, (heterocycle)alkyl, hydroxy, hydroxyalkyl, nitro, nitroalkyl, oxo, and thio(oxo);

$R^7$ is selected from the group consisting of hydrogen, alkyl, aryl, cycloalkyl, cycloalkylalkyl, heterocycle, (heterocycle)alkyl, and trialkylsilyl;

$R^9$ is selected from the group consisting of hydrogen, alkoxyalkyl, alkyl, amidoalkyl, aminoalkyl, aryl, arylalkyl, cycloalkyl, cycloalkylalkyl, carboxyalkyl, heterocycle, (heterocycle)alkyl, hydroxyalkyl, and a nitrogen protecting group;

each $R^{12}$ is independently selected from the group consisting of hydrogen, alkoxy, alkyl, amino, halo, and hydroxy;

m is 0,1,2,3 or 4;

n is 0,1,2,3 or 4;

p is 0,1,2,3 or 4; and q is 0,1,2,3 or 4.

In another embodiment, the present invention provides a compound of formula (II)

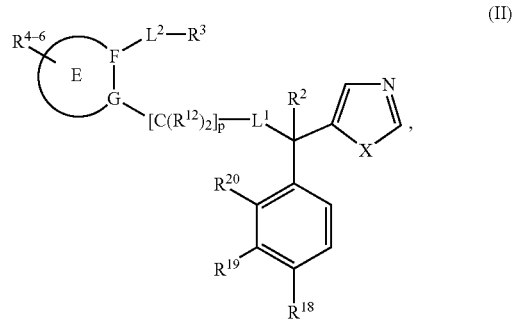

(II)

or a therapeutically acceptable salt thereof, wherein

E, F, G, $L^1, L^2$, X, $R^2$, $R^3$, $R^{4-6}, R^{12}$, and p are as defined in formula (I); and $R^{18}$, $R^{19}$, and $R^{20}$ are each independently selected from the group consisting of hydrogen, cyano, and halo.

In a preferred embodiment, the present invention provides a compound of formula (II) wherein E, F, G, and $R^{4-6}$ are as defined in formula (I); and $L^1$ is selected from the group consisting of O and $C_2$ alkynylene;

$L^2$ is selected from the group consisting of a bond, $NR^9SO_2$; and $C(O)NR^9$;

wherein each group is drawn with its left end attached to F and its right end attached to $R^3$;

X is NR⁷;

R² is selected from the group consisting of hydrogen and hydroxy;

R³ is selected from the group consisting of aryl and heterocycle;

R¹² is hydrogen; and p is 0 or 1.

In another embodiment the present invention provides a compound of formula (III)

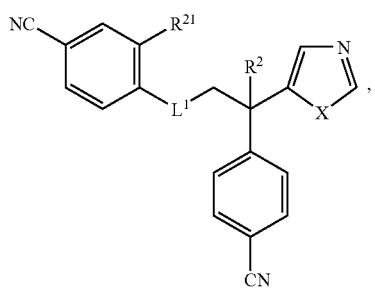

(III)

or a therapeutically acceptable salt therof, wherein $L^1$, X, and $R^2$ are as defined in formula (I); and $R^{21}$ is selected from the group consisting of aryl and heterocycle.

In a preferred embodiment the present invention provides a compound of formula (III) wherein $L^1$ is selected from the group consisting of $NR^9$ and O;

X is selected from the group consisting of $NR^7$ and S; and $R^2$ is selected from the group consisting of amino, halo and hydroxy.

In a more preferred embodiment the present invention provides a compound of formula (III) wherein $L^1$ is O; and X is $NR^7$.

In a most preferred embodiment the present invention provides a compound of formula (III) wherein $L^1$ is O;

X is $NR^7$;

$R^2$ is hydroxy; and $R^{21}$ is aryl.

In another embodiment the present invention provides a process for preparing a single enantiomer of a compound of formula (IV)

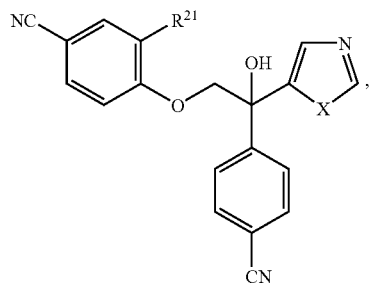

(IV)

or a therapeutically acceptable salt thereof, wherein
$R^{21}$ and X are as defined in formula (III);
the process comprising:
(a) reacting a compound of formula (V)

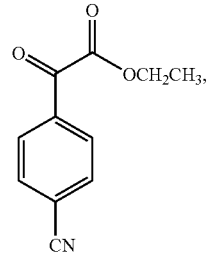

(V)

with (1R,2S,5R)-(–)-menthol in the presence of titanium ethoxide;
(b) reacting the product of step (a) with a compound of formula (VI)

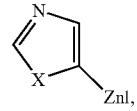

(VI)

wherein X is as defined in formula (III),
in the presence of magnesium bromide diethyl etherate;
(c) reacting the product of step (b) with a reducing agent; and
(d) reacting the product of step (c) with a compound of formula (VII)

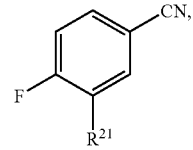

(VII)

in the presence of a base.

In another embodiment the present invention provides a process for preparing a single enantiomer of a compound of formula (IV), the process comprising:
(a) reacting a compound of formula (V) with (1R,2S,5R)-(–)-menthol in the presence of titanium ethoxide;
(b) reacting the product of step (a) with a compound of formula (VI) in the presence of magnesium bromide diethyl etherate;
(c) reacting the product of step (b) with a reducing agent;
(d) reacting the product of step (c) with 4-fluoro-3-bromobenzonitrile in the presence of a base; and
(e) reacting the product of step (d) with a compound of formula (VIII)

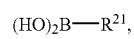

(VIII)

in the presence of a palladium catalyst.

In another embodiment the present invention provides a pharmaceutical composition comprising a compound of formula (I)–(III) or a therapeutically acceptable salt thereof, in combination with a therapeutically acceptable carrier.

In another embodiment the present invention provides a method for inhibiting farnesyltransferase in a patient in recognized need of such treatment comprising administering to the patient a therapeutically acceptable amount of a compound of formula (I)–(III), or a therapeutically acceptable salt thereof.

In another embodiment the present invention provides a method for treating cancer in a patient in recognized need of such treatment comprising administering to the patient a therapeutically acceptable amount of a compound of formula (I)–(III), or a therapeutically acceptable salt thereof.

DETAILED DESCRIPTION OF THE INVENTION

The present invention provides substituted imidazoles and substituted thiazoles which inhibit farnesyltransferase. As used in the specification, the following terms have the meanings indicated:

The term "alkanoyl," as used herein, refers to an alkyl group attached to the parent molecular moiety through a carbonyl group.

The term "alkenyl," as used herein, refers to a monovalent straight or branched chain group of two to six carbon atoms containing at least one carbon-carbon double bond.

The term "alkenylene," as used herein, refers to a divalent group derived from a straight or branched chain hydrocarbon containing at least one double bond.

The term "$C_2$ alkenylene," as used herein, refers to a divalent group derived from a hydrocarbon of two carbon atoms containing a double bond.

The term "alkoxy," as used herein, refers to an alkyl group attached to the parent molecular moiety through an oxygen atom.

The term "alkoxyalkyl," as used herein, refers to an alkoxy group attached to the parent molecular moiety through an alkyl group.

The term "alkoxycarbonyl," as used herein, refers to an alkoxy group attached to the parent molecular moiety through a carbonyl group.

The term "alkyl," as used herein, refers to a monovalent group derived from a straight or branched chain saturated hydrocarbon by the removal of a single hydrogen atom.

The term "alkylene," as used herein, refers to a divalent group derived from a straight or branched saturated hydrocarbon.

The term "alkylsulfonyl," as used herein, refers to an alkyl group attached to the parent molecular moiety through a sulfonyl group.

The term "alkynyl," as used herein, refers to a monovalent straight or branched chain group of two to six carbon atoms containing at least one triple bond.

The term "alkynylene," as used herein, refers to a divalent group derived from a straight or branched chain hydrocarbon containing at least one triple bond.

The term "$C_2$ alkynylene," as used herein, refers to a divalent group derived from a hydrocarbon of two atoms containing a triple bond.

The term "amido," as used herein, refers to an amino group attached to the parent molecular moiety through a carbonyl group.

The term "amidoalkyl," as used herein, refers to an amido group attached to the parent molecular moiety through an alkyl group.

The term "amino," as used herein, refers to —$NR^{10}R^{11}$, wherein $R^{10}$ and $R^{11}$ are independently selected from the group consisting of hydrogen, alkanoyl, alkoxyalkyl, alkoxycarbonyl, alkyl, alkylsulfonyl, aryl, arylalkyl, and a nitrogen protecting group, wherein the aryl and the aryl part of the arylalkyl can be further optionally substituted with one, two, three, four, or five substituents independently selected from the group consisting of alkanoyl, alkyl, cyano, halo, hydroxy, and nitro.

The term "aminoalkyl," as used herein, refers to an amino group attached to the parent molecular moiety through an alkyl group.

The term "aminosulfonyl," as used herein, refers to an amino group attached to the parent molecular moiety through a sulfonyl group.

The term "aryl," as used herein, refers to a monocyclic-ring system, or a bicyclic- or a tricyclic-fused ring system wherein one or more of the fused rings are aromatic. Representative examples of aryl include, but are not limited to, anthracenyl, azulene, fluorenyl, indanyl, indenyl, naphthyl, phenyl, tetrahydronaphthyl, and the like. Aryl groups having an unsaturated or partially saturated ring fused to an aromatic ring can be attached through the saturated or the unsaturated part of the group. The aryl groups of this invention can be optionally substituted with one, two, three, four, or five substituents independently selected from the group consisting of $NR^9C(O)$, $C(O)NR^9$, alkanoyl, alkenyl, alkoxy, alkoxyalkyl, alkoxycarbonyl, alkyl, alkylsulfonyl, alkynyl, amido, amino, aminoalkyl, aminosulfonyl, arylalkyl, aryloxy, arylsulfonyl, azido, carbonyloxy, carboxy, cyano, cyanoalkyl, cycloalkyl, cycloalkylalkyl, formyl, halo, haloalkoxy, haloalkyl, heterocycle, (heterocycle)alkyl, hydroxy, hydroxyalkyl, nitro, nitroalkyl, oxo, thioalkoxy, thioalkoxyalkyl, thio(oxo), and an additional aryl group; wherein the additional aryl group, the aryl part of the arylalkyl, the aryl part of the aryloxy, the aryl part of the arylsulfonyl, the heterocycle, and the heterocycle part of the (heterocycle)alkyl can be further optionally substituted with one, two, or three substituents independently selected from the group consisting of $NR^9C(O)$, $C(O)NR^9$, alkanoyl, alkenyl, alkoxy, alkoxyalkyl, alkoxycarbonyl, alkyl, alkylsulfonyl, alkynyl, amino, aminoalkyl, aminosulfonyl, azido, carbonyloxy, carboxy, cyano, cyanoalkyl, cycloalkyl, formyl, halo, haloalkoxy, haloalkyl, hydroxy, hydroxyalkyl, nitro, nitroalkyl, oxo, thioalkoxy, thioalkoxyalkyl, and thio(oxo).

The term "arylalkyl," as used herein, refers to an aryl group attached to the parent molecular moiety through an alkyl group.

The term "aryloxy," as used herein, refers to an aryl group attached to the parent molecular moiety through an oxygen atom.

The term "arylsulfonyl," as used herein, refers to an aryl group attached to the parent molecular moiety through a sulfonyl group.

The term "azido," as used herein, refers to —$N_3$.

The term "base," as used herein, represents a reagent capable of accepting protons during the course of a reaction. Examples of bases include carbonate salts such as potassium carbonate, potassium bicarbonate, sodium carbonate, sodium bicarbonate, and cesium carbonate; halides such as cesium fluoride; phosphates such as potassium phosphate, potassium dihydrogen phosphate, and potassium hydrogen phosphate; hydroxides such as lithium hydroxide, sodium hydroxide, and potassium hydroxide; alkoxides such as sodium tert-butoxide, potassium tert-butoxide, and lithium tert-butoxide; alkyllithiums such as tert-butyllithium, n-butyllithium, and methyllithium; dialkylamides such as lithium diisopropylamide; disilylamides such as lithium hexamethyldisilazide, potassium hexamethyldisilazide, and sodium hexamethyldisilazide; alkylamines such as triethylamine, diisopropylamine, and diisopropylethylamine; heterocyclic amines such as 4-dimethylaminopyridine, 2,6-lutidine, 1-methylimidazole, pyridine, pyridazine, pyrimidine, and pyrazine; bicyclic amines such as 1,8-diazabicyclo(4.3.0)undec-7-ene; and hydrides such as lithium hydride, sodium hydride, and potassium hydride. The base chosen for a particular conversion depends on the nature of the starting materials, the solvent or solvents in which the reaction is conducted, and the temperature at which the reaction is conducted.

The term "carbonyl," as used herein, refers to —C(O)—.

The term "carbonyloxy," as used herein, refers to an alkanoyl group attached to the parent molecular moiety through an oxygen atom.

The term "carboxy," as used herein, refers to —CO$_2$H.

The term "carboxyalkyl," as used herein refers to a carboxy group attached to the parent molecular moiety through an alkyl group.

The term "cyano," as used herein, refers to —CN.

The term "cyanoalkyl," as used herein, refers to a cyano group attached to the parent molecular moiety through an alkyl group.

The term "cycloalkyl," as used herein, refers a non-aromatic cyclic ring system having three to eight carbon atoms, wherein each five-membered ring has zero to one double bond, each six-membered ring has zero to two double bonds, and each seven- and eight-membered ring has zero to three double bonds. Examples of cycloalkyl groups include cyclohexenyl, cyclohexyl, cyclopentyl, and the like. The cycloalkyl groups of the present invention can be optionally substituted with one, two, three, four, or five substituents independently selected from the group consisting of alkanoyl, alkoxy, alkoxyalkyl, alkoxycarbonyl, alkyl, amino, aminoalkyl, carbonyloxy, cyano, cyanoalkyl, formyl, halo, haloalkoxy, haloalkyl, hydroxy, hydroxyalkyl, nitro, nitroalkyl, oxo, thioalkoxy, thioalkoxyalkyl, and thio(oxo).

The term "cycloalkylalkyl," as used herein, refers to a cycloalkyl group attached to the parent molecular moiety through an alkyl group.

The term "formyl," as used herein, refers to a hydrogen attached to the parent molecular moiety through a carbonyl group.

The term "halo," or "halogen," as used herein, refers to F, Cl, Br, or I.

The term "haloalkoxy," as used herein, refers to a haloalkyl group attached to the parent molecular moiety through an oxygen atom.

The term "haloalkyl," as used herein, refers to an alkyl group substituted by one, two, three, or four halogen atoms.

The term "heterocycle," as used herein, refers to a five-, six-, or seven-membered ring containing one, two, or three heteroatoms independently selected from the group consisting of nitrogen, oxygen, and sulfur. The five-membered ring has zero to two double bonds and the six- and seven-membered rings have zero to three double bonds. The term "heterocycle" also includes bicyclic groups in which the heterocycle ring is fused to an aryl group or another heterocycle. The heterocycle groups of the present invention can be substituted at a carbon atom or a nitrogen atom in the group. Representative examples of heterocycle include, but are not limited to, pyridinyl, dihydropyridinyl, 2(1H)-pyridonyl, 4(1H)-pyridonyl, pyrimidinyl, dihydropyrimidinyl, thienyl, furyl, pyrazinyl, and the like.

The heterocycle groups of the present invention can be optionally substituted with one, two, three, or four substituents independently selected from the group consisting of NR$^9$C(O), C(O)NR$^9$, alkanoyl, alkenyl, alkoxy, alkoxyalkyl, alkoxycarbonyl, alkyl, alkylsulfonyl, alkynyl, amido, amino, aminoalkyl, aminosulfonyl, aryl, arylalkyl, aryloxy, arylsulfonyl, azido, carbonyloxy, carboxy, cyano, cyanoalkyl, cycloalkyl, cycloalkylalkyl, formyl, halo, haloalkoxy, haloalkyl, (heterocycle)alkyl, hydroxy, hydroxyalkyl, nitro, nitroalkyl, thioalkoxy, thioalkoxyalkyl, thio(oxo), and an additional heterocycle group; wherein the additional heterocycle group, the heterocycle part of the (heterocycle)alkyl, the aryl, the aryl part of the arylalkyl, the aryl part of the aryloxy, and the aryl part of the arylsulfonyl can be further optionally substituted with one, two, or three substituents independently selected from the group consisting of NR$^9$C(O), C(O)NR$^9$, alkanoyl, alkenyl, alkoxy, alkoxyalkyl, alkoxycarbonyl, alkyl, alkylsulfonyl, alkynyl, amino, aminoalkyl, aminosulfonyl, azido, carbonyloxy, carboxy, cyano, cyanoalkyl, cycloalkyl, formyl, halo, haloalkoxy, haloalkyl, hydroxy, hydroxyalkyl, nitro, nitroalkyl, oxo, thioalkoxy, thioalkoxyalkyl, and thio(oxo).

The term "(heterocycle)alkyl," as used herein, refers to a heterocycle group attached to the parent molecular moiety through an alkyl group.

The term "hydroxy," as used herein, refers to —OH.

The term "hydroxyalkyl," as used herein, refers to a hydroxy group attached to the parent molecular moiety through an alkyl group.

The term "nitro," as used herein, refers to —NO$_2$.

The term "nitroalkyl," as used herein, refers to a nitro group attached to the parent molecular moiety through an alkyl group.

The term "nitrogen protecting group," as used herein, refers to groups intended to protect an amino group against undesirable reactions during synthetic procedures. Common N-protecting groups comprise acyl groups such as acetyl, benzoyl, 2-bromoacetyl, 4-bromobenzoyl, tert-butylacetyl, carboxaldehyde, 2-chloroacetyl, 4-chlorobenzoyl, α-chlorobutyryl, 4-nitrobenzoyl, o-nitrophenoxyacetyl, phthalyl, pivaloyl, propionyl, trichloroacetyl, and trifluoroacetyl; sulfonyl groups such as benzenesulfonyl, and p-toluenesulfonyl; carbamate forming groups such as benzyloxycarbonyl (Cbz), tert-butyloxycarbonyl (Boc), p-chlorobenzyloxycarbonyl, p-methoxybenzyloxycarbonyl, and the like.

The term "oxo," as used herein, refers to (═O).

The term "coupling catalyst," as used herein, represents a palladium complex which enhances the rate of a biaryl coupling. Examples of catalysts include palladium(II) acetate, tetrakis(triphenylphosphine)palladium(0), Pd$_2$(dba)$_3$, Pd$_2$Cl$_2$(dba), and PdCl$_2$(PPh$_3$)$_2$. Each of these catalysts can be used with an additive such as triphenylphosphine, 2-dicyclohexylphosphino-2'-dimethylaminobiphenyl, triphenylarsine, or a trialkylphosphine such as tributylphosphine optionally present.

The term "reducing agent," as used herein, represents a reagent capable of converting a ketone to an alcohol. Preferred reducing agents for the practice of the present invention include sodium borohydride, sodium cyanoborohydride, sodium triacetoxyborohydride, and lithium borohydride.

The term "sulfonyl," as used herein, refers to —SO$_2$—.

The term "thioalkoxy," as used herein, refers to an alkyl group attached to the parent molecular moiety through a sulfur atom.

The term "thioalkoxyalkyl," as used herein, refers to a thioalkoxy group attached to the parent molecular moiety through an alkyl group.

The term "thio(oxo)," as used herein, refers to (=S).

The term "trialkylsilyl," as used herein, refers to —SiR$^{13}_3$, wherein R$^{13}$ is alkyl.

The compounds of the present invention can exist as therapeutically acceptable salts. The term "therapeutically acceptable salt," as used herein, represents salts or zwitterionic forms of the compounds of the present invention which are water or oil-soluble or dispersible, which are suitable for treatment of diseases without undue toxicity, irritation, and allergic response; which are commensurate with a reasonable benefit/risk ratio, and which are effective for their intended use. The salts can be prepared during the final isolation and purification of the compounds or separately by reacting an amino group with a suitable acid. Representative acid addition salts include acetate, adipate, alginate, citrate, aspartate, benzoate, benzenesulfonate, bisulfate, butyrate, camphorate, camphorsulfonate, digluconate, glycerophosphate, hemisulfate, heptanoate, hexanoate, formate, fumarate, hydrochloride, hydrobromide, hydroiodide, 2-hydroxyethansulfonate (isethionate), lactate, maleate, mesitylenesulfonate, methanesulfonate, naphthylenesulfonate, nicotinate, 2-naphthalenesulfonate, oxalate, pamoate, pectinate, persulfate, 3-phenylproprionate, picrate, pivalate, propionate, succinate, tartrate, trichloroacetate, trifluoroacetate, phosphate, glutamate, bicarbonate, para-toluenesulfonate, and undecanoate. Also, amino groups in the compounds of the present invention can be quaternized with methyl, ethyl, propyl, and butyl chlorides, bromides, and iodides; dimethyl, diethyl, dibutyl, and diamyl sulfates; decyl, lauryl, myristyl, and steryl chlorides, bromides, and iodides; and benzyl and phenethyl bromides. Examples of acids which can be employed to form therapeutically acceptable addition salts include inorganic acids such as hydrochloric, hydrobromic, sulfuric, and phosphoric, and organic acids such as oxalic, maleic, succinic, and citric.

The present compounds can also exist as therapeutically acceptable prodrugs. The term "therapeutically acceptable prodrug," refers to those prodrugs or zwitterions which are suitable for use in contact with the tissues of patients without undue toxicity, irritation, and allergic response, are commensurate with a reasonable benefit/risk ratio, and are effective for their intended use. The term "prodrug," refers to compounds which are rapidly transformed in vivo to parent compounds of formula (I) for example, by hydrolysis in blood.

Asymmetric centers exist in the compounds of the present invention. When the absolute stereochemistry is known, it is designated using the terms "R" and "S" as defined in "IUPAC 1974 Recommendations for Section E, Fundamental Stereochemistry," *Pure Appl. Chem*. 1976, 45, 13–30 or the symbols (+) or (−) as determined by optical rotation. If absolute stereochemistry is not known, the terms "R", "S", (+), and (−) are omitted. In the absence of these terms, the presence of a single enantiomer will be demonstrated by the spectroscopic data shown for that example (i.e., optical rotation, chiral HPLC). It should be understood that the invention encompasses both stereochemical isomeric forms, or mixtures thereof, which possess the ability to inhibit farnesyltransferase. Individual stereoisomers of compounds can be prepared by synthesis from starting materials containing chiral centers or by preparation of mixtures of enantiomeric products followed by separation such as conversion to a mixture of diastereomers followed by separation or recrystallization, chromatographic techniques, or direct separation of enantiomers on chiral chromatographic columns. Starting compounds of particular stereochemistry are either commercially available or can be made and resolved by techniques known in the art.

According to methods of treatment, the compounds of the present invention can be useful for the prevention of metastases from the tumors described above either when used alone or in combination with radiotherapy and/or other chemotherapeutic treatments conventionally administered to patients for treating cancer. When using the compounds of the present invention for chemotherapy, the specific therapeutically effective dose level for any particular patient will depend upon factors such as the disorder being treated and the severity of the disorder; the activity of the particular compound used; the specific composition employed; the age, body weight, general health, sex, and diet of the patient; the time of administration; the route of administration; the rate of excretion of the compound employed; the duration of treatment; and drugs used in combination with or coincidently with the compound used. For example, when used in the treatment of solid tumors, compounds of the present invention can be administered with chemotherapeutic agents such as alpha inteferon, COMP (cyclophosphamide, vincristine, methotrexate, and prednisone), etoposide, mBACOD (methortrexate, bleomycin, doxorubicin, cyclophosphamide, vincristine, and dexamethasone), PRO-MACE/MOPP (prednisone, methotrexate (w/leucovin rescue), doxorubicin, cyclophosphamide, taxol, etoposide/ mechlorethamine, vincristine, prednisone, and procarbazine), vincristine, vinblastine, angioinhibins, TNP-470, pentosan polysulfate, platelet factor 4, angiostatin, LM-609, SU-101, CM-101, Techgalan, thalidomide, SP-PG, and the like. For example, a tumor may be treated conventionally with surgery, radiation or chemotherapy and a compound of the present invention subsequently administered to extend the dormancy of micrometastases and to stabilize and inhibit the growth of any residual primary tumor.

The compounds of the present invention can be administered orally, parenterally, osmotically (nasal sprays), rectally, vaginally, or topically in unit dosage formulations containing carriers, adjuvants, diluents, vehicles, or combinations thereof. The term "parenteral" includes infusion as well as subcutaneous, intravenous, intramuscular, and intrasternal injection.

Parenterally administered aqueous or oleaginous suspensions of the compounds of the present invention can be formulated with dispersing, wetting, or suspending agents. The injectable preparation can also be an injectable solution or suspension in a diluent or solvent. Among the acceptable diluents or solvents employed are water, saline, Ringer's solution, buffers, dilute acids or bases, dilute amino acid solutions, monoglycerides, diglycerides, fatty acids such as oleic acid, and fixed oils such as monoglycerides or diglycerides.

The chemotherapeutic effect of parenterally administered compounds can be prolonged by slowing their absorption. One way to slow the absorption of a particular compound is administering injectable depot forms comprising suspensions of crystalline, amorphous, or otherwise water-insoluble forms of the compound. The rate of absorption of the compound is dependent on its rate of dissolution which is, in turn, dependent on its physical state. Another way to slow absorption of a particular compound is administering injectable depot forms comprising the compound as an oleaginous solution or suspension. Yet another way to slow absorption of a particular compound is administering injectable depot forms comprising microcapsule matrices of the compound trapped within liposomes, microemulsions, or biodegradable polymers such as polylactide-polyglycolide, polyorthoesters or polyanhydrides. Depending on the ratio of drug to polymer and the composition of the polymer, the rate of drug release can be controlled.

Transdermal patches also provide controlled delivery of the compounds. The rate of absorption can be slowed by using rate controlling membranes or by trapping the compound within a polymer matrix or gel. Conversely, absorption enhancers can be used to increase absorption.

Solid dosage forms for oral administration include capsules, tablets, pills, powders, and granules. In these solid dosage forms, the active compound can optionally comprise diluents such as sucrose, lactose, starch, talc, silicic acid, aluminum hydroxide, calcium silicates, polyamide powder, tableting lubricants, and tableting aids such as magnesium stearate or microcrystalline cellulose. Capsules, tablets and pills can also comprise buffering agents; and tablets and pills can be prepared with enteric coatings or other release-controlling coatings. Powders and sprays can also contain excipients such as talc, silicic acid, aluminum hydroxide, calcium silicate, polyamide powder, or mixtures thereof. Sprays can additionally contain customary propellants such as chlorofluorohydrocarbons or substitutes thereof.

Liquid dosage forms for oral administration include emulsions, microemulsions, solutions, suspensions, syrups, and elixirs comprising inert diluents such as water. These compositions can also comprise adjuvants such as wetting, emulsifying, suspending, sweetening, flavoring, and perfuming agents.

Topical dosage forms include ointments, pastes, creams, lotions, gels, powders, solutions, sprays, inhalants, and transdermal patches. The compound is mixed under sterile conditions with a carrier and any needed preservatives or buffers. These dosage forms can also include excipients such as animal and vegetable fats, oils, waxes, paraffins, starch, tragacanth, cellulose derivatives, polyethylene glycols, silicones, bentonites, silicic acid, talc and zinc oxide, or mixtures thereof. Suppositories for rectal or vaginal administration can be prepared by mixing the compounds of the present invention with a suitable nonirritating excipient such as cocoa butter or polyethylene glycol, each of which is solid at ordinary temperature but fluid in the rectum or vagina. Ophthalmic formulations comprising eye drops, eye ointments, powders, and solutions are also contemplated as being within the scope of the present invention.

The total daily dose of the compounds of the present invention administered to a host in single or divided doses can be in amounts from about 0.1 to about 200 mg/kg body weight or preferably from about 0.25 to about 100 mg/kg body weight. Single dose compositions can contain these amounts or submultiples thereof to make up the daily dose.

Preferred compounds of the present invention are compounds of formula (III) wherein $L^1$ is selected from the group consisting of $NR^9$ and O;

X is selected from the group consisting of $NR^7$ and S; and $R^2$ is selected from the group consisting of amino, halo, and hydroxy.

The compounds of the invention have been shown to demonstrate enhanced potency as well as improved pharmacokinetic and electrophysiological profiles.

Determination of Biological Activity

The ability of the compounds of the present invention to inhibit farnesyltransferase can be measured according to the method described in *J. Biol. Chem.*, 266: 14603 (1991) or *J. Biol. Chem.*, 270:660–664 (1995). Procedures for determination of the inhibition of farnesylation of the oncogene protein Ras are described in *J. Biol. Chem.*, 266:15575–15578 (1991) and U.S. Pat. No. 5,245,061. Inhibition of rat brain farnesyltransferase can also be measured in vitro using an Amersham Life Science commercial scintillation proximity assay kit and substituting a biotin-K Ras B fragment (0.1 µM final concentration) for the biotin-lamin substrate provided by Amersham. The enzyme can be purified according to *Cell*, 62: 81–88 (1990), utilizing steps one, two, and three. The specific activity of the enzyme is approximately 10 nmol substrate farnesylated/mg of enzyme/hour. The percent inhibition of the farnesylation caused by the compounds of the present invention (at $10^{-6}$ M) compared to an uninhibited control sample can be evaluated in the same Amersham test system.

Briefly, $^3$H-Farnesyldiphosphate (final concentration 0.6 µM), H-Ras (final concentration 5.0 µM), and the test compound (various final concentrations from a stock solution in 50% DMSO/water; final concentration DMSO <2%) were mixed in a buffer comprising 50 mM HEPES (pH 7.5), 30 mM $MgCl_2$, 20 mM KCl, 10 µM $ZnCl_2$, 5 mM DTT, and 0.01% Triton X-100) to give a final volume of 50 µL. The mixture was brought to 37° C., treated with enzyme, incubated for 30 minutes, treated with 1 M HCl/ethanol (1 mL) to stop the reaction, stirred for 15 minutes at room temperature, diluted with ethanol (2 mL), filtered through a 2.5 cm glass microfiber filter (Whatman) with ethanol rinses (4×2 mL). The glass filter was transferred to a scintillation vial and treated with scintillation fluid (5 mL). The radioisotope retained on the glass fiber filter was counted and reflected the activity of the enzyme. The percent inhibition of farnesyltransferase was determined for representative compounds of the present invention at concentrations of $10^{-7}$M, $10^{-8}$M, or $10^{-9}$M. The results are summarized in Tables 1 and 2.

TABLE 1

Inhibitory Potencies of Representative Compounds

| Example | % Inhibition at $10^{-7}$ M |
|---|---|
| 1 | 73 |
| 2 | >66 |
| 3 | 90 |
| 4 | 89 |
| 5 | 79 |
| 6 | >91 |
| 7 | >85 |
| 8 | 96 |
| 9 | >91 |
| 10 | 94 |
| 11 | 92 |
| 12 | 92 |
| 13 | 84 |
| 14 | 96 |
| 15 | 82 |
| 16 | >83 |
| 17 | >85 |
| 18 | 97 |
| 19 | >95 |
| 20 | 94 |
| 21 | 91 |
| 22 | 64 |
| 23 | >92 |
| 24 | 94 |
| 25 | 87 |

TABLE 1-continued

Inhibitory Potencies of Representative Compounds

| Example | % Inhibition at $10^{-7}$ M |
|---|---|
| 26 | 98 |
| 27 | 47 |
| 28 | >85 |
| 29 | 92 |
| 30 | 92 |
| 31 | >97 |
| 32 | >98 |
| 33 | >98 |
| 34 | >97 |
| 35 | 96 |
| 36 | 70 |
| 37 | >96 |
| 38 | 80 |
| 39 | 74 |
| 40 | >83 |
| 41 | 10 |
| 42 | 87 |
| 43 | >81 |
| 44 | 89 |
| 45 | 87 |
| 46 | 100 |
| 47 | 100 |
| 48 | 100 |
| 49 | 100 |
| 50 | 100 |
| 51 | 100 |
| 52 | 100 |
| 53 | 100 |
| 54 | 100 |

TABLE 2

Inhibitory Potencies of Representative Compounds

| Example | % Inhibition at $10^{-8}$ M |
|---|---|
| 55 | 98 |
| 56 | 97 |
| 57 | 98 |
| 58 | 96 |
| 59 | 83 |
| 60 | 73 |
| 61 | 96 |
| 62 | 93 |
| 63 | 97 |
| 64 | 90 |
| 65 | 75 ($10^{-9}$ M) |
| 66 | 93 |
| 67 | 94 |
| 68 | 91 |
| 69 | 95 |
| 70 | 94 |
| 71 | 97 |
| 72 | 94 |
| 73 | 96 |
| 74 | 95 |
| 75 | 96 |
| 76 | 95 |
| 77 | 98 |
| 78 | 97 |
| 79 | 96 |
| 80 | 90 |
| 81 | 90 |
| 82 | 15 |
| 83 | 96 |
| 84 | 92 |
| 85 | 65 |
| 86 | 94 |
| 87 | 91 |
| 88 | 90 |

TABLE 2-continued

Inhibitory Potencies of Representative Compounds

| Example | % Inhibition at $10^{-8}$ M |
|---|---|
| 89 | 75 ($10^{-9}$ M) |
| 90 | 92 |
| 91 | 77 |
| 92 | 94 |
| 93 | 90 ($10^{-9}$ M) |

As shown by the data in Table 1, the compounds of the present invention, including but not limited to those specified in the examples, are useful for the treatment of diseases caused or exacerbated by farnesyltransferase. As farnesyltransferase inhibitors, these compounds are useful in the treatment of both primary and metastatic solid tumors and carcinomas of the breast; colon; rectum; lung; oropharynx; hypopharynx; esophagus; stomach; pancreas; liver; gallbladder; bile ducts; small intestine; urinary tract (kidney, bladder,and urothelium); female genital tract (cervix, uterus, and ovaries); male genital tract (prostate, seminal vasicles, and testes); endocrine glands (thyroid, adrenal, and pituitary); skin (hemangiomas, melanomas, and sarcomas); tumors of the brain, nerves, and eyes; meninges (astrocytomas, gliomas, glioblastomas, retinoblastomas, neuromas, neuroblastomas, and meningiomas); solid tumors arising from hematopoietic malignancies (leukemias and chloromas); plasmacytomas; plaques; tumors of mycosis fungoides; cutaneous T-cell lymphoma/leukemia; lymphomas including Hodgkin's and non-Hodgkin's lymphomas; prophylaxis of autoimmune diseases (rheumatoid, immune and degenerative arthritis); ocular diseases (diabetic retinopathy, retinopathy of prematurity, corneal graft rejection, retrolental fibroplasia, neovascular glaucoma, rubeosis, retinal neovascularization due to macular degeneration, and hypoxia); skin diseases (psoriasis, hemagiomas and capillary proliferation within atherosclerotic plaques).

Synthetic Methods

Abbreviations which have been used in the descriptions of the schemes and the examples that follow are: THF for tetrahydrofuran; MTBE for methyl tert-butyl ether; NBS for N-bromosuccinimide; AIBN for 2,2'-azobisisobutyronitrile; dba for dibenzylideneacetone; DMF for N,N-dimethylformamide; NMP for N-methylpyrrolidinone; TBAF for tetrabutylammonium fluoride; PDC for pyridinium dichromate; OAc for acetate; DMSO for dimethylsulfoxide; dba for dibenzylideneacetone; Et for ethyl; and DME for 1,2-dimethoxyethane.

The compounds and processes of the present invention will be better understood in connection with the following synthetic schemes which illustrate the methods by which the compounds of the invention may be prepared. Starting materials can be obtained from commercial sources or prepared by well-established literature methods known to those of ordinary skill in the art. The groups $R^{1-9}$ are as defined above unless otherwise noted below.

This invention is intended to encompass compounds having formulas (I), (II), and (III) when prepared by synthetic processes or by metabolic processes. Preparation of the compounds of the invention by metabolic processes include those occurring in the human or animal body (in vivo) or processes occurring in vitro.

Scheme 1

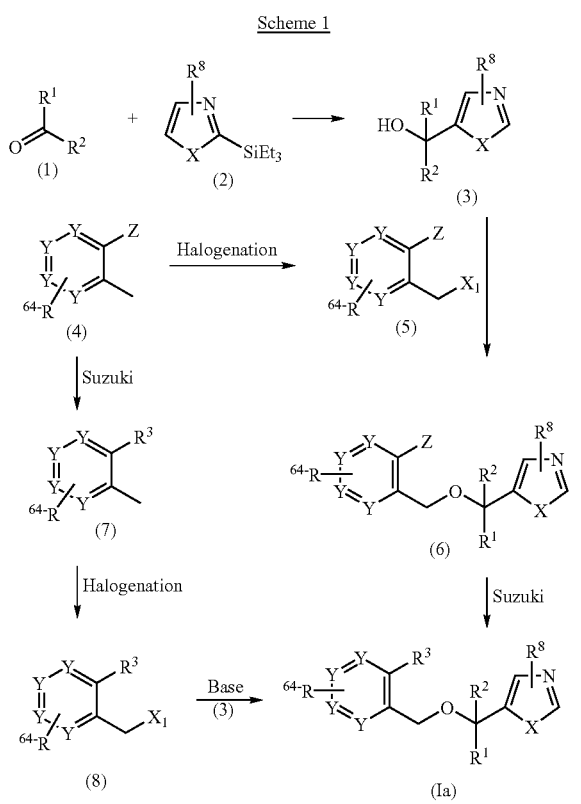

Scheme 2

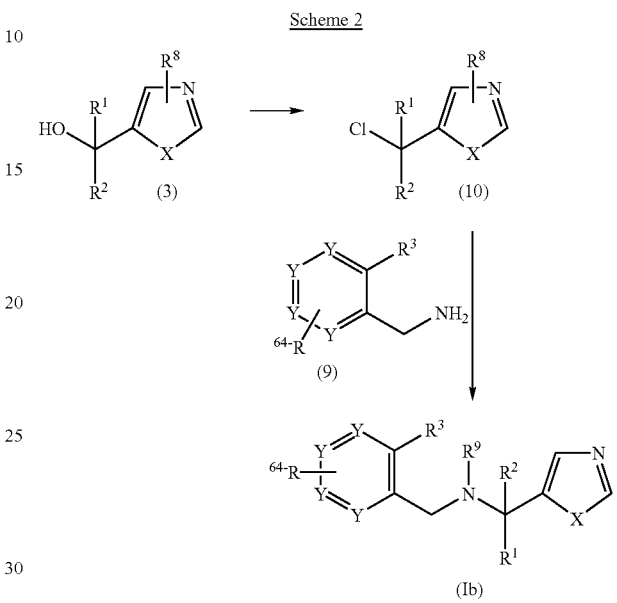

Scheme 1 shows the synthesis of compounds of formula (Ia) (wherein Y is CH or N). Compounds of formula (2) can be treated sequentially with strong base, compounds of formula (1), and acid to provide compounds of formula (3). A representative base is tert-butyllithium, while representative acids include HCl, HF, and acetic acid. Examples of solvents used in these reactions include THF, MTBE, and diethyl ether. The reaction is conducted at about −78° C. for about 30 minutes to about 2 hours.

Compounds of formula (5) wherein $X_1$ is Br and Z is a halogen (prepared by radical halogenation of compound (4) with NBS in the presence of an additive such as benzoyl peroxide or AIBN) can be reacted with compounds of formula (3) in the presence of a base, such as silver (I) oxide, to provide compounds of formula (6). Examples of solvents used in these reactions include dichloromethane, carbon tetrachloride, and chloroform. The reaction is conducted at about 20° C. to about 35° C. and reaction times are typically about 8 to about 24 hours.

Compounds of formula (6) can be converted to compounds of formula (Ia) wherein $R^3$ is aryl or heterocycle by coupling with the corresponding boronic acid in the presence of catalytic palladium and base. Representative palladium catalysts include $Pd(PPh_3)_4$, $PdCl_2(PPh_3)_2$, and $Pd_2(dba)_3$ with tris 2-furylphosphine. Examples of bases used in these reactions include $Na_2CO_3$, $Cs_2CO_3$, and $K_2CO_3$. Solvents typically used in these reactions include toluene, ethanol, water, and mixtures thereof. The reaction is usually conducted at about 80° C. to about 110° C. and reaction times are typically about 8 to about 24 hours.

Alternatively, compounds of formula (4) can be converted to compounds of formula (7) by Suzuki, Negishi or Stille coupling. Radical halogenation of compounds of formula (7) with a halide source such as NBS and an initiator such as AIBN in a solvent such as carbon tetrachloride at a temperature of about 80° C. to about 110° C. over approximately 6 to 24 hours gives compounds of formula (8).

Compounds of formula (8) can be reacted directly with compounds of formula (3) in the presence of a base (such as silver oxide or NaH) to provide compounds of formula (Ia).

As shown in Scheme 2, compounds of formula (3) can be converted to compounds of formula (10) by treatment with a chlorinating agent such as thionyl chloride in a non-reactive solvent such as THF. Compounds of formula (10) can be reacted with compounds of formula (9) (formed by treatment of compounds of formula (8) with sodium azide and triphenylphosphine) to provide compounds of formula (Ib) wherein $R^9$ is hydrogen.

Compounds of formula (Ib) wherein $R^9$ is hydrogen can be intraconverted to compounds of formula (Ib) wherein $R^9$ is alkyl, a nitrogen protecting group, or phenyl by methods known to those of ordinary skill in the art.

Scheme 3

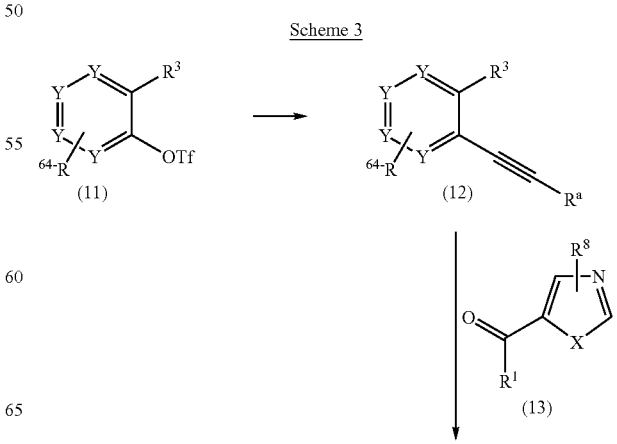

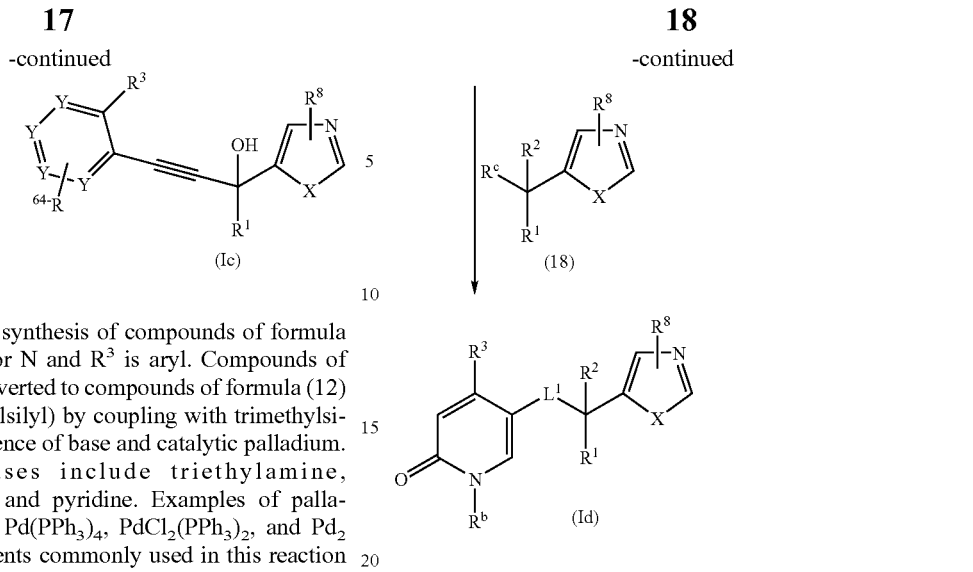

(Ic)

(18)

(Id)

Scheme 3 shows the synthesis of compounds of formula (Ic) wherein Y is CH or N and $R^3$ is aryl. Compounds of formula (11) can be converted to compounds of formula (12) (wherein $R^a$ is trimethylsilyl) by coupling with trimethylsilylacetylene in the presence of base and catalytic palladium. Representative bases include triethylamine, diisopropylethylamine, and pyridine. Examples of palladium catalysts include $Pd(PPh_3)_4$, $PdCl_2(PPh_3)_2$, and $Pd_2(dba)_3$ with $PPh_3$. Solvents commonly used in this reaction include DMF, NMP, and dioxane. The reaction is conducted at about 60° C. to about 90° C. and reaction times are typically about 1 to about 4 hours.

Conversion of compounds of formula (12) (wherein $R^a$ is trimethylsilyl) to compounds of formula (12) (wherein $R^a$ is hydrogen) can be accomplished by treatment with a desilylating agent such as $K_2CO_3$ or TBAF using conditions known to those of ordinary skill in the art.

Compounds of formula (12) can be treated with strong base and reacted with compounds of formula (13) (prepared by oxidation of compounds of formula (3) using reagents such as $MnO_2$, $KMnO_4$, or PDC) to provide compounds of formula (Ic). Representative bases include tert-butyllithium, n-butyllithium, and lithium hexamethyldisilazide. Examples of solvents used in these reactions include THF, pentane, hexane, diethyl ether, and mixtures thereof. The reaction is usually conducted at about −78° C. to about 30° C. and reaction times are typically about 6 to about 24 hours.

Compounds of formula (Ic) can be converted to the corresponding alkenylene or alkylene compound by hydrogenation in the presence of a catalyst. Representative hydrogenation catalysts include Pd—$CaCO_3$ with quinoline, $Pd(OAc)_2$, Pd—$BaSO_4$ with quinoline, Pd/C, and $PdCl_2$ with DMF.

Scheme 4

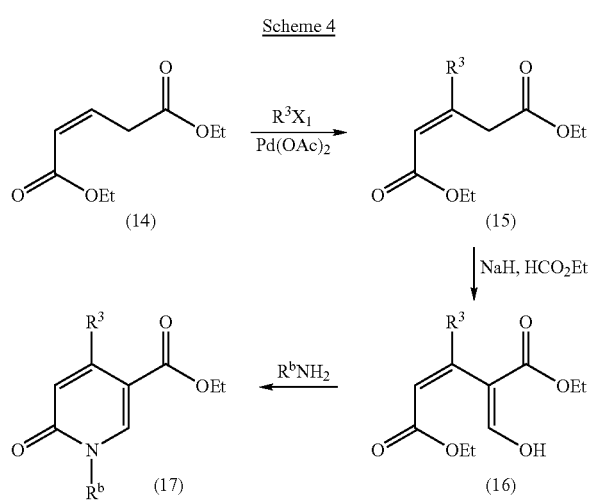

Scheme 4 shows the synthesis of compounds of formula (Id). Compounds of formula (14) can be converted to compounds of formula (15) by coupling with an appropriately substituted halide ($R^3X_1$) in the presence of a palladium catalyst. Representative palladium catalysts include $Pd(OAc)_2$ and $PdCl_2$. Example of solvents used in these reactions include DMF, NMP, and dioxane. The reaction is usually conducted at about 80° C. to about 110° C. and reaction times are typically about 12 to about 36 hours.

Compounds of formula (15) can be condensed with ethyl formate in the presence of base to provide compounds of formula (16). Examples of bases include NaH, KH, and lithium hexamethyldisilazide. Solvents typically used in these reactions include diethyl ether, MTBE, and THF. The reaction is usually conducted at about 20° C. to about 30° C. and reaction times are typically about 2 to about 6 hours.

Conversion of compounds of formula (16) to compounds of formula (17) can be accomplished by treatment with an appropriately substituted amine ($R^bNH_2$ wherein $R^b$ is alkyl, aryl, or benzyl) in the presence of acid. Representative acids include acetic acid and trifluoroacetic acid. Examples of solvents used in these reactions include THF, acetonitrile, ethanol, and mixtures thereof. The reaction is usually conducted at about 65° C. to about 100° C. and reaction times are typically about 30 minutes to about 2 hours.

Compounds of formula (17) can be converted to compounds of formula (Id) wherein $L^1$ is $CO_2$ or CONH by hydrolysis of the ester (using methods known to those of ordinary skill in the art), conversion to the acid chloride by treatment with oxalyl chloride and DMF, and condensation with compounds of formula (18) ($R^c$ is OH, prepared as described in Scheme 1; or $NH_2$, prepared by reacting compounds of formula (10) with ammonia). Examples of solvents used in these reactions include THF, MTBE, and diethyl ether. The reaction is conducted at about −10° C. to about 30° C. and reaction times are typically about 12 to about 24 hours.

Scheme 5

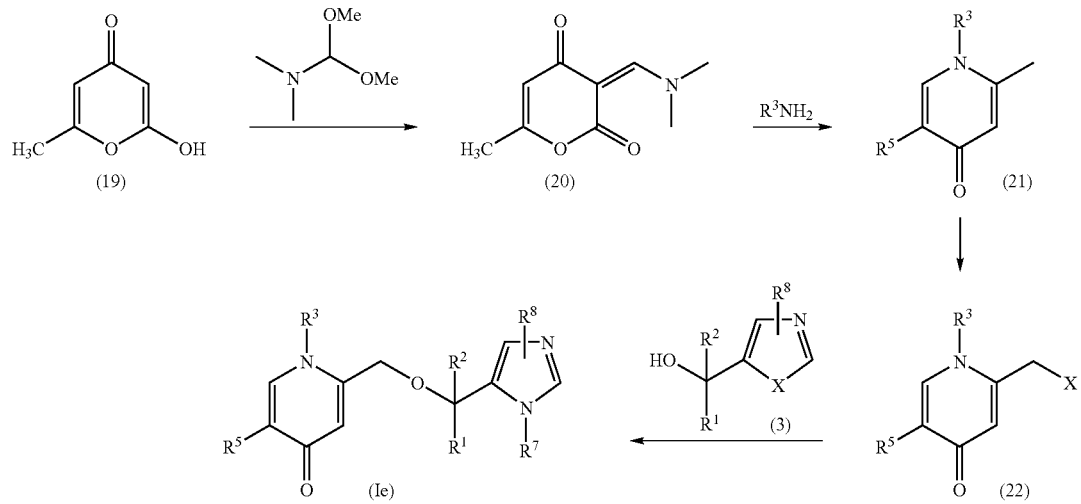

Scheme 5 shows the synthesis of compounds of formula (Ie). Compounds of formula (19) can be converted to compounds of formula (20) by treatment with dimethylformamide dimethyl acetal. Examples of solvents used in this reaction include toluene, benzene, and xylene. The reaction is conducted at about 20° C. to about 30° C. and reaction times are typically about 2 to about 8 hours.

Compounds of formula (20) can be converted to compounds of formula (21) ($R^5$ is $CO_2H$) by treatment with an appropriately substituted amine ($R^3NH_2$) in the presence of base. Representative bases include sodium tert-butoxide, sodium methoxide, and potassium tert-butoxide. Examples of solvents include ethanol, methanol, and isopropanol. The reaction is conducted at about 80° C. to about 100° C. and reaction times are typically about 12 to about 24 hours.

Compounds of formula (21) wherein $R^5$ is $CO_2H$ can be converted to compounds of formula (21) wherein $R^5$ is cyano by methods known to those of ordinary skill in the art.

Conversion of compounds of formula (21) to compound of formula (Ie) can be achieved following the procedures described in Scheme 1.

Scheme 6

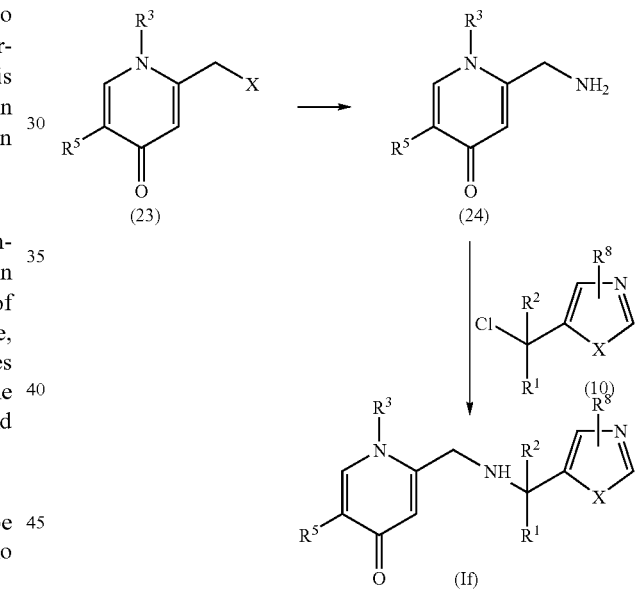

Scheme 6 shows the synthesis of compounds of formula (If). Compounds of formula (23) can be converted to compounds of formula (If) in two steps using the procedures described in Scheme 2.

Scheme 7

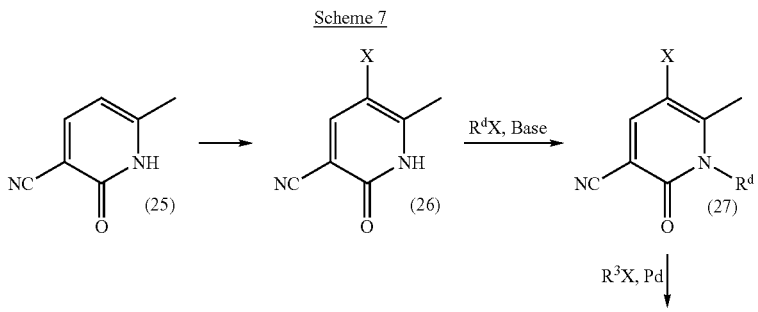

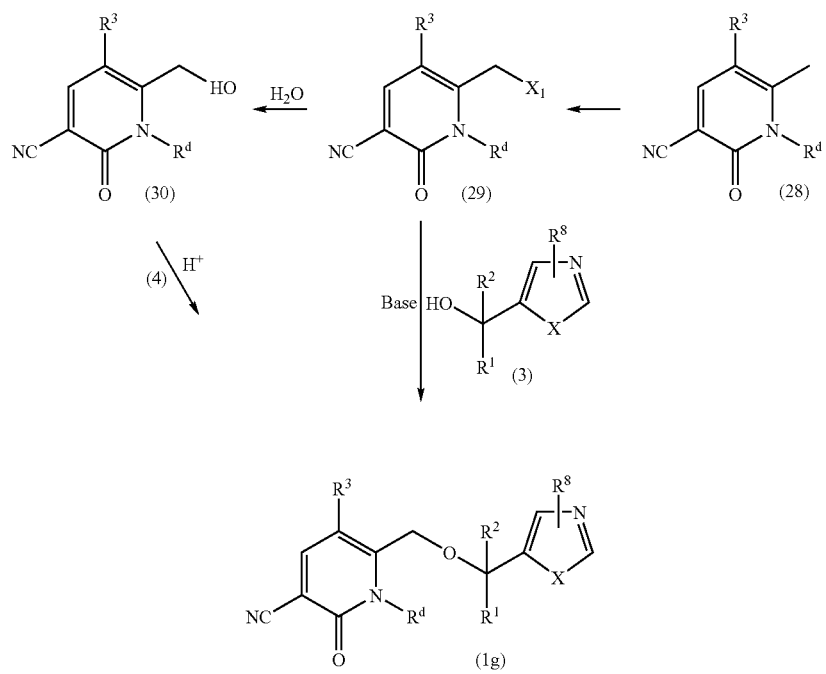

Scheme 7 shows the synthesis of compounds of formula (Ig). Compounds of formula (25) can be converted to compounds of formula (26) wherein X is a halogen. Typically X is Br which can be formed by treatment of compound (25) with NBS in a solvent such as carbon tetrachloride.

Compounds of formula (26) can be converted to compounds of formula (27) by reaction with $R^dX_1$ (usually $R^d$ is alkyl, acyl, allyl, or benzyl) and base. Palladium-assisted coupling of compounds of formula (27) and $R^3X_1$ produces compounds of formula (28). Typically, $R^3X_1$ is a boronic acid reacted with a compound of formula (27), a palladium catalyst, and a base in a solvent such as toluene, ethanol, water or mixtures thereof at about 80° C. to about 110° C. over an approximately 2 to 24 hour reaction period. Typical palladium catalysts are $Pd(PPh_3)_4$, $PdCl_2(PPh_3)_2$ or $Pd_2(dba)_3$ and typical bases are $K_2CO_3$, $Cs_2CO_3$ or $Na_2CO_3$.

Radical halogenation of compounds of formula (28) with a halide source such as NBS and an initiator such as AIBN in a solvent such as carbon tetrachloride at a temperature of about 80° C. to about 110° C. over approximately 4 to 24 hours gives compounds of formula (29).

Compounds of formula (29) can be hydrolyzed to give compounds of formula (30) which are then reacted with compounds of formula (3) and an acid such as para-toluene sulfonic acid in a solvent such as toluene, benzene, or xylenes at about 80° C. to about 140° C. to provide the desired compounds of formula (Ig). Alternatively, compounds of formula (29) can be reacted directly with compounds of formula (3) in the presence of a base (such as NaH, KH, and lithium hexamethyldisilazide) to provide compounds of formula (Ig).

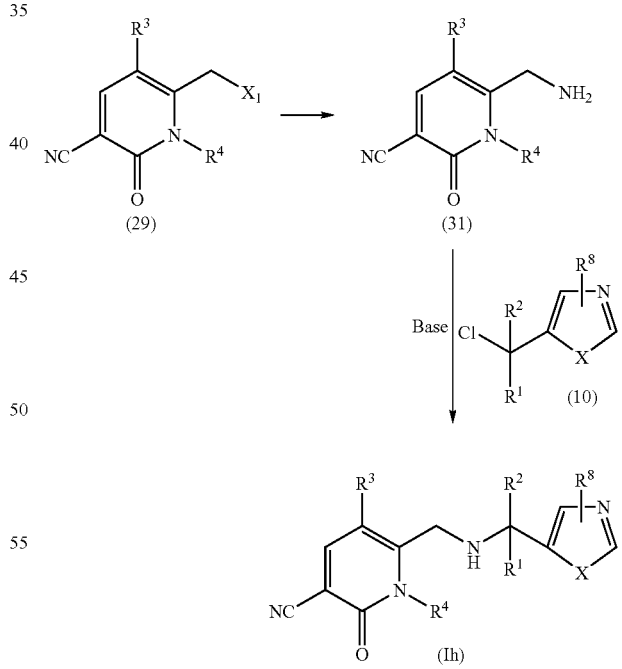

Scheme 8 shows the synthesis of compounds of formula (Ih). Compounds of formula (29) can be converted to compounds of formula (Ih) in two steps using procedures described in Scheme 2.

Scheme 9

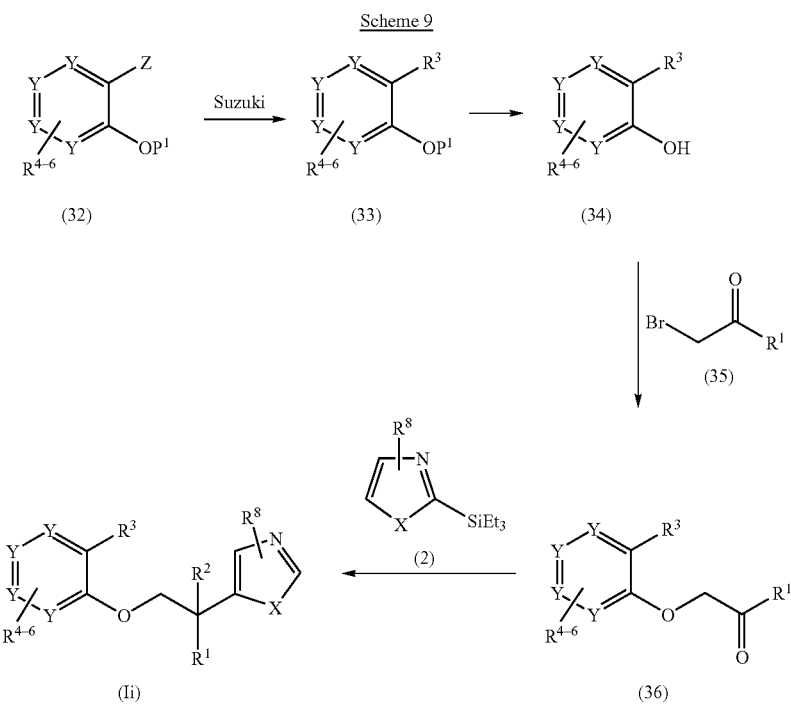

Compounds of formula (Ii) (wherein Y is CH or N) can be prepared as shown in Scheme 9. Compounds of formula (32) (wherein Z is a halogen and $P^1$ is a hydroxy protecting group such as methyl ethyl ether) can be converted to compounds of formula (33) using coupling procedures such as those described in Scheme 1.

Removal of $P^1$ from compounds of formula (33) provides compounds of formula (34). The conditions used for the deprotection are dependent on the nature of the protecting group as well as the other substituents on the molecule, and will generally be known to those of ordinary skill in the art.

Reaction of compounds of formula (34) with base and a compound of formula (35) provides compounds of formula (36). Representative bases include $K_2CO_3$, NaH, and $Na_2CO_3$. Examples of solvents used in these reactions include DMF, NMP, and DME. The reaction is typically run at temperatures between about 20° C. and about 40° C. and reaction times are typically between about 1 and about 6 hours.

Compounds of formula (36) can be reacted with compounds of formula (2) under the conditions described in Scheme 1 to provide compounds of formula (Ii) (wherein $R^2$ is OH).

Compounds of formula (Ii) where $R^2$ is OH can be converted to compounds of formula (Ii) where $R^2$ is F by reaction with (diethylamino)sulfur trifluoride. Representative solvents used in this reaction include dichloromethane, 1,2-dichloroethane, and chloroform. The reaction is typically conducted at temperatures between about −25° C. to about 0° C. for about 1 to about 4 hours.

Compounds of formula (Ii) where $R^2$ is OH can be converted to compounds of formula (Ii) where $R^2$ is $NH_2$ by reaction with ammonium hydroxide and ammonia. Examples of solvents used in these reactions include 1,4-dioxane and DME. The reaction is conducted at about −78° C. to about −45° C. for about 6 to about 24 hours.

Scheme 10

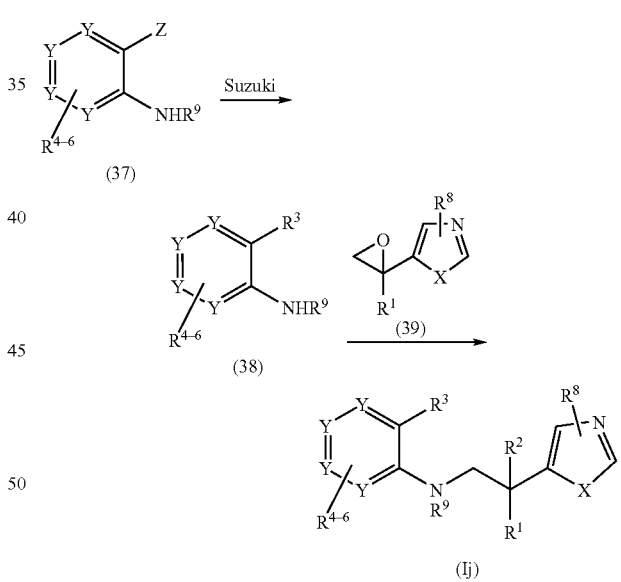

Compounds of formula (Ij) (wherein Y is CH or N) can be prepared as shown in Scheme 10. Compounds of formula (37) (wherein Z is a halogen) can be converted to compounds of formula (38) using coupling procedures such as those described in Scheme 1.

Conversion of compounds of formula (38) to compounds of formula (Ij) (where $R^2$ is OH) can be accomplished by treatment with base and reaction with a compound of formula (39). Representative bases include NaH, LiHMDS, and LDA. Examples of solvents used in these reactions include DMF, DME, and 1,4-dioxane. The reaction is usually conducted at about 20° C. to about 40° C. for about 1 to about 6 hours.

Compounds of formula (Ij) where $R^2$ is OH can be converted to compounds of formula (Ij) where $R^2$ is F or compounds of formula (Ij) where $R^2$ is $NH_2$ by the methods described in Scheme 9.

The present invention will now be described in connection with certain preferred embodiments which are not intended to limit its scope. On the contrary, the present invention covers all alternatives, modifications, and equivalents as can be included within the scope of the claims. Thus, the following examples, which include preferred embodiments, will illustrate the preferred practice of the present invention, it being understood that the examples are for the purposes of illustration of certain preferred embodiments and are presented to provide what is believed to be the most useful and readily understood description of its procedures and conceptual aspects.

Compounds of the invention were named by ACD/ChemSketch version 4.01 (developed by Advanced Chemistry Development, Inc., Toronto, ON, Canada) or were given names which appeared to be consistent with ACD nomenclature.

EXAMPLE 1

4-(((4-chloro-2-iodobenzyl)oxy)(1-methyl-1H-imidazol-5-yl)methyl)benzonitrile

EXAMPLE 1A 1-(bromomethyl)-4-chloro-2-iodobenzene

A mixture of 4-chloro-2-iodo-1-methylbenzene (3.95 g, 15.6 mmol), N-bromosuccinimide (3.10 g, 17.6 mmol), and benzoyl peroxide (0.1 g) in carbon tetrachloride (100 mL) was heated to reflux for 48 hours, filtered, and concentrated. The concentrate was purified by flash column chromatography on silica gel with 4:100 ethyl acetate/hexanes to provide 3.34 g (64%) of the desired product. MS (DCI/$NH_3$) m/z 330, 332 (M+H)$^{30}$; $^1$H NMR (CDCl$_3$) δ 7.85 (d, 1H), 7.40–7.32 (m, 2H), 4.59 (s, 2H).

EXAMPLE 1B 4-(hydroxy(1-methyl-1H-imidazol-5-yl)methyl)benzonitrile

A solution of 1-methyl-2-(triethylsilyl)-1H-imidazole (3.35 g, 17.08 mmol) in THF (50 mL) at –78° C. was treated dropwise with 2.5M tert-butyllithium in pentane (22.4 mL, 17.1 mmol), stirred for 30 minutes, treated dropwise with a solution of 4-cyanobenzaldehyde (2.04 g, 15.56 mmol) in THF (10 mL), and stirred for 1 hour. The mixture was quenched with methanol (4 mL), treated with 1N HCl (40 mL), warmed to room temperature, adjusted to pH 12 with 30% NaOH, and extracted with ethyl acetate. The combined extracts were washed with brine, dried (MgSO$_4$), filtered, and concentrated. The concentrate was triturated with 4:1 hexanes/ethyl acetate to provide 2.95 g (89%) of the desired product. MS (DCI/$NH_3$) m/z 214 (M+H)$^+$; $^1$H NMR (CDCl$_3$) δ 7.67 (d, 2H), 7.53 (d, 2H), 7.40 (s, 1H), 6.67 (s, 1H), 5.95 (s, 1H), 3.53 (s, 3H).

EXAMPLE 1C 4-(((4-chloro-2-iodobenzyl)oxy)(1-methyl-1H-imidazol-5-yl)methyl)benzonitrile A mixture of Example 1B (0.5 g, 2.34 mmol), Example 1A (1.16 g, 3.5 mmol), and silver(I) oxide (1.60 g, 6.9 mmol) in dichloromethane (30 mL) at room temperature was stirred in darkness for 12 hours, filtered through a pad of diatomaceous earth (Celite®), and concentrated. The concentrate was purified by flash column chromatography on silica gel with 100:3:0.3 ethyl acetate/methanol/$NH_4OH$ to provide 0.70 g (70%) of the desired product. MS (ESI) m/z 464 (M+H)$^+$; $^1$H NMR (CDCl$_3$) δ 7.85 (s, 1H), 7.68–7.66 (m, 2H), 7.53 (d, 2H), 7.47 (m, 1H), 7.34–7.32 (m, 2H), 6.95 (s, 1H), 5.65 (s, 1H), 4.52 (m, 2H), 3.41 (s, 3H).

EXAMPLE 2

4-(((5-chloro(1,1'-biphenyl)-2-yl)methoxy)(1-methyl-1H-imidazol-5-yl)methyl)benzonitrile A mixture of Example 1 (0.080 g, 0.177 mmol), phenylboronic acid (0.043 g, 0.035 mmol), sodium carbonate (0.042 g, 0.531 mmol), and tetrakis(triphenylphosphine)palladium (0) (0.01 g, 0.0089 mmol) in a mixture of toluene (3 mL), ethanol (3 mL), and water (1 mL) was heated to reflux for 12 hours, cooled to room temperature, treated with ethyl acetate (10 mL), washed with brine, dried (MgSO$_4$), filtered, and concentrated. The concentrate was purified by flash column chromatography on silica gel with 100:3:0.3 ethyl acetate/methanol/$NH_4OH$ to provide 0.045 g (62%) of the desired product. MS (ESI) m/z 414 (M+H)$^+$; $^1$H NMR (CDCl$_3$) δ 7.60 (d, 2H), 7.49 (s, 1H), 7.40–7.25 (m, 11H), 6.75 (s, 1H), 5.42 (s, 1H), 4.47 (d, 1H), 4.38 (d, 1H), 3.29 (s, 3H); Anal. Calcd for $C_{25}H_{20}ClN_3O \cdot 0.41C_4H_8O_2$: C, 71.10; H, 5.21; N, 9.31. Found: C, 71.04; H, 5.11; N, 9.42.

EXAMPLE 3

4-(((2',5-dichloro(1,1'-biphenyl)-2-yl)methoxy)(1-methyl-1H-imidazol-5-yl)methyl)benzonitrile The desired product was prepared as a mixture of rotamers by substituting 2-chlorophenylboronic acid for phenylboronic acid in Example 2. MS (ESI) m/z 448 (M+H)$^+$; $^1$H NMR (CDCl$_3$) δ 7.62–7.56 (m, 2H), 7.48–7.16 (m, 11H), 6.78 and 6.69 (s, 1H total), 5.38 (s, 1H), 4.40–4.18 (m, 2H total), 3.32 and 3.24 (s, 3H total); Anal. Calcd for $C_{25}H_{19}Cl_2N_3O \cdot 0.35C_4H_8O_2$: C, 66.17; H, 4.59; N, 8.77. Found: C, 66.41; H, 4.88; N, 8.64.

EXAMPLE 4

4-(((5-chloro-2'-methyl(1,1'-biphenyl)-2-yl)methoxy)(1-methyl-1H-imidazol-5-yl)methyl)benzonitrile The desired product was prepared as a mixture of rotamers by substituting 2-methylphenylboronic acid for phenylboronic acid in Example 2. MS (APCI) m/z 428 (M+H)$^+$; $^1$H NMR (CDCl$_3$) δ 7.58 (d, 2H), 7.48–7.00 (m, 11H), 6.72 and 6.69 (s, 1H total), 5.35 (s, 1H), 4.30–4.05 (m, 2H), 3.32 and 3.30 (s, 3H total), 2.01 and 1.98 (s, 3H total): Anal. Calcd for $C_{26}H_{22}ClN_3O \cdot 0.51C_4H_8O_2$: C, 71.22; H, 5.56; N, 8.89. Found: C, 71.31; H, 5.50; N, 8.69.

EXAMPLE 5

4-(((5-chloro-2'-methoxy(1,1'-biphenyl)-2-yl)methoxy)(1-methyl-1H-imidazol-5-yl)methyl)benzonitrile The desired product was prepared as a mixture of rotamers by substituting 2-methoxyphenylboronic acid for phenylboronic acid in Example 2. MS (ESI) m/z 444 (M+H)$^+$; $^1$H NMR (CDCl$_3$) δ 7.60–6.70 (m, 13H), 6.72 and 6.69 (s, 1H total), 5.36 (s, 1H), 4.30–4.05 (m, 2H), 3.63 (s, 3H), 3.31 and 3.17 (s, 3H total); Anal. Calcd for $C_{26}H_{22}ClN_3O_2 \cdot 0.45C_4H_8O_2$: C, 69.05; H, 5.34; N, 8.69. Found: C, 68.89; H, 5.41; N, 9.03.

EXAMPLE 6

4-(((3',5-dichloro(1,1'-biphenyl)-2-yl)methoxy)(1-methyl-1H-imidazol-5-yl)methyl)benzonitrile The desired product was prepared by substituting 3-chlorophenylboronic acid for phenylboronic acid in Example 2. MS (ESI) m/z 448 (M+H)$^+$; $^1$H NMR (CDCl$_3$) δ 7.61 (d, 2H), 7.43 (s, 1H), 7.38–7.27 (m, 8H), 7.16–7.13 (m, 2H), 6.82 (s, 1H), 5.45 (s, 1H), 4.43 (d,1H), 4.33 (d, 1H), 3.30 (s, 3H); Anal. Calcd for $C_{25}H_{19}Cl_2N_3O \cdot 0.45C_4H_8O_2$: C,65.95; H, 4.67; N, 8.61. Found: C, 66.22; H, 4.83; N, 8.34.

EXAMPLE 7

4-(((5-chloro-3'-methyl(1,1'-biphenyl)-2-yl)methoxy)(1-methyl-1H-imidazol-5-yl)methyl)benzonitrile The desired product was prepared by substituting 3-methylphenylboronic acid for phenylboronic acid in Example 2. MS (ESI) m/z 428 (M+H)$^+$; $^1$H NMR (CDCl$_3$) δ 7.61 (d, 2H), 7.40–7.20 (m, 9H), 7.08–7.05 (m, 2H), 6.76 (s, 1H), 5.41 (s, 1H), 4.45 (d, 1H), 4.37 (d, 1H), 3.27 (s, 3H), 2.35 (s, 3H); Anal. Calcd for $C_{26}H_{22}ClN_3O \cdot 0.28C_4H_8O_2$: C, 71.97; H, 5.40; N, 9.28. Found: C, 71.89; H, 5.46; N, 9.28.

EXAMPLE 8

4-(((5-chloro-3'-(trifluoromethyl)(1,1'-biphenyl)-2-yl)methoxy)(1-methyl-1H-imidazol-5-yl)methyl)benzonitrile The desired product was prepared by substituting 3-trifluoromethylphenylboronic acid for phenylboronic acid in Example 2. MS (ESI) m/z 482 (M+H)$^+$; $^1$H NMR (CDCl$_3$) δ 7.67–7.31 (m, 12H), 6.86 (s, 1H), 5.45 (s, 1H), 4.42 (d, 1H), 4.32 (d, 1H), 3.27 (s,3H); Anal. Calcd for $C_{26}H_{19}ClF_3N_3O \cdot 0.52C_4H_8O_2$: C, 63.91; H, 4.42; N, 7.96. Found: C, 63.85; H, 4.42; N, 7.96.

EXAMPLE 9

4-(((5-chloro-3'-methoxy(1,1'-biphenyl)-2-yl)methoxy)(1-methyl-1H-imidazol-5-yl)methyl)benzonitrile The desired product was prepared by substituting 3-methoxyphenylboronic acid for phenylboronic acid in Example 2. MS (ESI) m/z 444 (M+H)$^+$; $^1$H NMR (CDCl$_3$) δ 7.61 (d, 2H), 7.41–7.28 (m, 7H), 6.92 (m, 1H), 6.85–6.80 (m, 2H), 6.76 (s, 1H), 5.43 (s, 1H), 4.46 (d, 1H), 4.39 (d, 1H), 3.79 (s, 3H), 3.30 (s, 3H); Anal. Calcd for $C_{26}H_{22}ClN_3O_2 \cdot 0.35C_4H_8O_2$: C, 69.32; H, 5.27; N, 8.85. Found: C, 69.40; H, 5.47; N, 8.82.

EXAMPLE 10

4-(((5-chloro-3'-fluoro(1,1'-biphenyl)-2-yl)methoxy)(1-methyl-1H-imidazol-5-yl)methyl)benzonitrile The desired product was prepared by substituting 3-fluorophenylboronic acid for phenylboronic acid in Example 2. MS (DCI/NH$_3$) m/z 432 (M+H)$^+$; $^1$H NMR (CDCl$_3$) δ 7.63 (d, 2H), 7.40–7.29 (m, 7H), 7.11–7.00 (m, 4H), 6.80 (s, 1H), 5.46 (s, 1H), 4.43 (d, 1H), 4.35 (d, 1H), 3.30 (s, 3H); Anal. Calcd for $C_{25}H_{19}ClFN_3O \cdot 0.35C_4H_8O_2$: C, 68.53; H, 4.75; N, 9.08. Found: C, 68.55; H, 4.89; N, 9.21.

EXAMPLE 11

4-(((4',5-dichloro(1,1'-biphenyl)-2-yl)methoxy)(1-methyl-1H-imidazol-5-yl)methyl)benzonitrile The desired product was prepared by substituting 4-chlorophenylboronic acid for phenylboronic acid in Example 2. MS (APCI) m/z 448 (M+H)$^+$; $^1$H NMR (CDCl$_3$) δ 7.63 (d, 2H), 7.40–7.18 (m, 11H), 6.81 (s, 1H), 5.45 (s, 1H), 4.45 (d, 1H), 4.33 (d, 1H), 3.27 (s, 3H); Anal. Calcd for $C_{25}H_{19}Cl_2N_3O \cdot 0.34C_4H_8O_2$: C, 66.20; H, 4.58; N, 8.79. Found: C, 66.29; H, 4.72; N, 8.67.

EXAMPLE 12

4-(((4-chloro-2-(1-naphthyl)benzyl)oxy)(1-methyl-1H-imidazol-5-yl)methyl)benzonitrile The desired product was prepared as a mixture of rotamers by substituting 1-naphthylboronic acid for phenylboronic acid in Example 2. MS (APCI) m/z 464 (M+H)$^+$; $^1$H NMR (DMSO-d$_6$) δ 7.94 (m, 2H), 7.51–7.28 (m, 11H), 7.10 and 7.03 (s, 1H total), 5.22 and 5.19 (s, 1H total), 4.26–4.10 (m, 2H), 3.27 and 3.07 (s, 3H total); Anal. Calcd for $C_{29}H_{22}ClN_3O \cdot 0.50C_4H_8O_2$: C, 73.30; H, 5.16; N, 8.27. Found: C, 73.23; H, 5.20; N, 8.35.

EXAMPLE 13

4-(((3'-amino-5-chloro(1,1'-biphenyl)-2-yl)methoxy)(1-methyl-1H-imidazol-5-yl)methyl)benzonitrile The desired product was prepared by substituting 3-aminophenylboronic acid for phenylboronic acid in Example 2. MS (APCI) m/z 429 (M+H)$^+$; $^1$H NMR (DMSO-d$_6$) δ 9.07 (s, 1H), 7.98 (d, 1H), 7.86 (d, 2H), 7.60 (d, 1H), 7.49 (dd, 8.0 Hz, 1H), 7.60 (d, 2H), 7.43 (d, 1H), 7.29 (d, 1H), 7.25 (s, 1H), 7.07–6.95 (m, 3H), 5.95 (s, 1H), 4.54 (d, 1H), 4.40 (d, 1H), 3.63 (s, 3H).

EXAMPLE 14

3'-chloro-6'-(((4-cyanophenyl)(1-methyl-1H-imidazol-5-yl)methoxy)methyl)(1,1'-biphenyl)-3-carbonitrile The desired product was prepared by substituting 3-cyanophenylboronic acid for phenylboronic acid in Example 2. MS (APCI) m/z 439 (M+H)$^+$; $^1$H NMR (DMSO-d$_6$) δ 8.99 (s, 1H), 7.89–7.83 (m, 3H), 7.69–7.52 (m, 5H), 7.43 (d, 2H), 7.40 (d, 1H), 7.38 (d, 1H), 5.88 (s, 1H), 7.22 (s,1H), 4.52 (d, 1H), 4.36 (d, 1H), 3.62 (s, 3H).

EXAMPLE 15

4-(((2'-acetyl-5-chloro(1,1'-biphenyl)-2-yl)methoxy)(1-methyl-1H-imidazol-5-yl)methyl)benzonitrile The desired product was prepared as a mixture of rotamers by substituting 2-acetylphenylboronic acid for phenylboronic acid in Example 2. MS (APCI) m/z 456 (M+H)$^+$; $^1$H NMR (DMSO-d$_6$) δ 9.00 (s, 1H), 7.83 (d, 2H), 7.64–7.54 (m, 5H), 7.46 (m, 1H), 7.37 (d, 2H), 7.22 (m, 1H), 7.16 (m, 1H), 5.83 (s, 1H), 4.37 and 4.26 (2d, 1H total), 4.19 and 4.09 (2d, 1H total), 3.63 and 3.59 (s, 3H total), 2.23 and 2.16 (s, 3H total).

EXAMPLE 16

4-(((4'-acetyl-5-chloro(1,1'-biphenyl)-2-yl)methoxy)(1-methyl-1H-imidazol-5-yl)methyl)benzonitrile The desired product was prepared by substituting 4-acetylphenylboronic acid for phenylboronic acid in Example 2. MS (APCI) m/z 456 (M+H)$^+$; $^1$H NMR (DMSO-d$_6$) δ 9.04 (s, 1H), 7.95 (d, 2H), 7.82 (d, 2H), 7.65–7.52 (m, 2H), 7.46 (t, 4H), 7.36 (d, 1H), 7.24 (s,1H), 5.90 (s, 1H), 4.53 (d, 1H), 4.37 (d, 1H), 3.63 (s, 3H), 2.64 (s, 3H).

EXAMPLE 17

4-(((5-chloro-3',4'-dimethyl(1,1'-biphenyl)-2-yl)methoxy)(1-methyl-1H-imidazol-5-yl)methyl)benzonitrile The desired product was prepared by substituting 3,4-dimethylphenylboronic acid for phenylboronic acid in Example 2. MS (APCI) m/z 442 (M+H)$^+$; $^1$H NMR (DMSO-d$_6$) δ 8.95 (s, 1H), 7.83 (d, 2H), 7.58 (d, 1H), 7.62–7.52 (m, 1H), 7.45 (d, 2H), 7.27 (d, 1H), 7.20 (s, 1H), 7.13 (d, 1H), 7.06 (s, 1H), 7.01–6.99 (m, 1H), 5.87 (s, 1H), 4.52 (d, 1H), 4.38 (d, 1H), 3.60 (s, 3H), 2.27 (s, 3H), 2.21 (s, 3H).

EXAMPLE 18

4-(((4'-tert-butyl-5-chloro(1,1'-biphenyl)-2-yl)methoxy)(1-methyl-1H-imidazol-5-yl)methyl)benzonitrile The desired product was prepared by substituting 4-tert-butylphenylboronic acid for phenylboronic acid in Example 2. MS (APCI) m/z 470 (M+H)$^+$; $^1$H NMR (DMSO-d$_6$) δ 8.87 (s, 1H), 7.85 (d, 2H), 7.60 (d, 1H), 7.50 (d, 2H), 7.48–7.45 (m, 1H), 7.39 (d, 2H), 7.31 (d, 1H), 7.23 (d, 2H), 7.12 (s, 1H), 5.87 (s, 1H), 4.52 (d, 1H), 4.33 (d, 1H), 3.63 (s, 3H), 1.32 (s, 9H).

EXAMPLE 19

4-(((5-chloro-3'-ethoxy(1,1'-biphenyl)-2-yl)methoxy)(1-methyl-1H-imidazol-5-yl)methyl)benzonitrile The desired product was prepared by substituting 3-ethoxyphenylboronic acid for phenylboronic acid in Example 2. MS (APCI) m/z 458 (M+H)$^+$; $^1$H NMR (DMSO-d$_6$) δ 8.94 (s,1H), 7.84 (d, 2H), 7.59(d, 1H), 7.63–7.52 (m, 1H), 7.49–7.46 (m, 1H), 7.45 (d, 2H), 7.32 (d, 1H), 7.29 (d, 1H), 6.95 (m, 1H), 7.19 (s, 1H), 6.86–6.83 (m, 1H), 5.89 (s, 1H), 4.52 (d, 1H), 4.39 (d, 1H), 3.98 (q, 2H), 3.62 (s, 3H), 1.03 (t, 3H).

EXAMPLE 20

4-(((5-chloro-2',5'-dimethoxy(1,1'-biphenyl)-2-yl)methoxy)(1-methyl-1H-imidazol-5-yl)methyl)benzonitrile The desired product was prepared by substituting 2,5-dimethoxyphenylboronic acid for phenylboronic acid in Example 2. MS (APCI) m/z 474 (M+H)$^+$; $^1$H NMR (DMSO-d$_6$) δ 8.95 (s, 1H), 7.83 (m, 1H), 7.64–7.52 (m, 4H), 7.46–7.44 (m, 1H), 7.21 (m, 1H), 7.17 (s, 1H), 6.94 (m, 2H), 6.69 (s, 1H), 5.82 (s, 1H), 4.45–4.15 (m, 2H), 3.70 (s, 6H), 3.53 (s, 3H).

EXAMPLE 21

4-(((5-chloro-3',4'-dimethoxy(1,1'-biphenyl)-2-yl)methoxy)(1-methyl-1H-imidazol-5-yl)methyl)benzonitrile The desired product was prepared by substituting 3,4-dimethoxyphenylboronic acid for phenylboronic acid in Example 2. MS (APCI) m/z: 474 (M+H)$^+$; $^1$H NMR (DMSO-d$_6$) δ 8.99(s, 1H), 7.84 (d, 2H), 7.64–7.42 (m, 2H), 7.47 (d, 2H), 7.33 (d, 1H), 7.25 (s, 1H), 6.94 (d, 1H), 6.88 (d, 1H), 6.80 (dd, 1H), 5.90 (s, 1H), 4.55 (d, 1H), 4.42 (d, 1H), 3.81 (s, 3H), 3.69 (s, 3H), 3.63 (s, 3H).

EXAMPLE 22

N-(5'-chloro-2'-(((4-cyanophenyl)(1-methyl-1H-imidazol-5-yl)methoxy)methyl)(1,1'-biphenyl)-3-yl)acetamide The desired product was prepared by substituting 3-(acetylamino)phenylboronic acid for phenylboronic acid in Example 2. MS (APCI) m/z 471 (M+H)$^+$; $^1$H NMR (DMSO-d$_6$) δ 10.00 (s, 1H), 8.98 (s, 1H), 7.82 (d, 2H), 7.64–7.48 (m, 4H), 7.42 (d, 2H), 7.32 (t, 1H), 7.28 (d, 1H), 7.19 (s, 1H), 6.96 (d, 1H), 5.88 (s, 1H), 4.52 (d, 1H), 4.38 (d, 1H), 3.62 (s, 3H), 2.06 (s, 3H).

EXAMPLE 23

4-(((2-(1,3-benzodioxol-5-yl)-4-chlorobenzyl)oxy)(1-methyl-1H-imidazol-5-yl)methyl)benzonitrile The desired product was prepared by substituting 1,3-benzodioxol-5-ylboronic acid for phenylboronic acid in Example 2. MS (APCI) m/z 458 (M+H)$^+$; $^1$H NMR (DMSO-d$_6$) δ 8.95 (s, 1H), 7.87 (d, 2H), 7.58 (d, 1H), 7.50 (d, 2H), 7.45 (dd, 1H), 7.28 (d, 1H), 7.20 (s, 1H), 6.93 (d, 1H), 6.89 (s, 1H), 6.76 (dd, 1H), 6.07 (d, 2H), 5.91 (s, 1H), 4.52 (d, 1H), 4.38 (d, 1H), 3.64 (s, 3H).

EXAMPLE 24

4-(((5-chloro-3',4',5'-trimethoxy(1,1'-biphenyl)-2-yl)methoxy)(1-methyl-1H-imidazol-5-yl)methyl)benzonitrile The desired product was prepared by substituting 3,4,5-trimethoxyphenylboronic acid for phenylboronic acid in Example 2. MS (APCI) m/z 504 (M+H)$^+$; $^1$H NMR (DMSO-d$_6$) δ 9.02 (s, 1H), 7.83 (d, 1H), 7.64–7.53 (m, 3H), 7.47 (d, 2H), 7.37 (d, 1H), 7.30 (s, 1H), 6.60 (s, 2H), 5.92 (s, 1H), 4.58 (d, 1H), 4.45 (d, 1H), 3.70 (m, 9H), 3.60 (s, 3H).

EXAMPLE 25

4-((1-methyl-1H-imidazol-5-yl)((2',3',5-trichloro(1,1'-biphenyl)-2-yl)methoxy)methyl)benzonitrile The desired product was prepared by substituting 2,3-dichlorophenylboronic acid for phenylboronic acid in Example 2. MS (APCI) m/z 482 (M+H)$^+$; $^1$H NMR (DMSO-d$_6$) δ 9.00 (s, 1H), 7.85–7.82 (m, 2H), 7.72–7.52 (m, 5H), 7.45–7.25 (m, 3H), 7.29 (d, 1H), 5.84 (s, 1H), 4.42 and 4.31 (2d, 1H total), 4.23 and 4.09 (2d, 1H total), 3.64 and 3.61 (2s, 3H total).

EXAMPLE 26

4-(((5-chloro-4'-(trifluoromethyl)(1,1'-biphenyl)-2-yl)methoxy)(1-methyl-1H-imidazol-5-yl)methyl)benzonitrile The desired product was prepared by substituting 4-(trifluoromethyl)phenylboronic acid for phenylboronic acid in Example 2. MS (APCI) m/z 498 (M+H)$^+$; $^1$H NMR (DMSO-d$_6$) δ 8.92 (s, 1H), 7.84 (d, 2H), 7.64–7.37 (m, 9H), 7.17 (s, 1H), 5.88 (s, 1H), 4.50 (d, 1H), 4.32 (d, 1H), 3.64 (s, 3H).

EXAMPLE 27

4-((1-methyl-1H-imidazol-5-yl)((3',5,5'-trichloro(1,1'-biphenyl)-2-yl)methoxy)methyl)benzonitrile The desired product was prepared by substituting 3,5-dichlorophenylboronic acid for phenylboronic acid in Example 2. MS (APCI) m/z 482 (M+H)$^+$; $^1$H NMR (DMSO-d$_6$) δ 8.97 (s, 1H), 7.83 (d, 2H), 7.65 (m, 3H), 7.52 (dd, 1H), 7.44 (d, 2H), 7.39 (d,1H), 7.31 (dd,1H), 7.22 (s, 1H), 5.88 (s, 1H), 4.51 (d, 1H), 4.36 (d, 1H), 3.64 (s, 3H).

EXAMPLE 28

4-((1-methyl-1H-imidazol-5-yl)((3',4',5-trichloro(1,1'-biphenyl)-2-yl)methoxy)methyl)benzonitrile The desired product was prepared by substituting 3,4-dichlorophenylboronic acid for phenylboronic acid in Example 2. MS (APCI) m/z 482 (M+H)$^+$; $^1$H NMR (DMSO-d$_6$) δ 8.98 (s, 1H), 7.86 (d, 2H), 7.73 (d, 1H), 7.65 (m, 1H), 7.61 (d, 1H), 7.52 (dd, 1H), 7.45 (d, 2H), 7.41 (m, 2H), 7.25 (s, 1H), 5.90 (s, 1H), 4.51 (d, 1H), 4.36 (d, 1H), 3.63 (s, 3H).

EXAMPLE 29

4-(((4-chloro-2-(5-formyl-2-thienyl)benzyl)oxy)(1-methyl-1H-imidazol-5-yl)methyl)benzonitrile The desired product was prepared by substituting 5-formyl-2-thienylboronic acid for phenylboronic acid in Example 2. MS (APCI) m/z 448 (M+H)$^+$; $^1$H NMR (DMSO-d$_6$) δ 9.95 (s, 1H), 9.05 (s, 1H), 8.02 (d, 1H), 7.87 (d, 2H), 7.67–7.51 (m, 5H), 7.40 (d, 1H), 7.33 (s, 1H), 6.01 (s, 1H), 4.69 (d, 1H), 4.57 (d, 1H), 3.63 (s, 3H).

EXAMPLE 30

4-(((5-chloro-3'-formyl(1,1'-biphenyl)-2-yl)methoxy)(1-methyl-1H-imidazol-5-yl)methyl)benzonitrile The desired product was prepared by substituting 3-formylphenylboronic acid for phenylboronic acid in Example 2. MS (APCI) m/z 442 (M+H)$^+$; $^1$H NMR (DMSO-d$_6$) δ 10.03 (s, 1H), 9.03 (s, 1H), 7.86 (s, 1H), 7.95 (d, 1H), 7.82 (d, 2H), 7.69–7.52 (m, 4H), 7.43 (d, 2H), 7.41 (d, 1H), 7.24 (s, 1H), 5.89 (s, 1H), 4.53 (d, 1H), 4.37 (d, 1H), 3.61 (s, 3H).

EXAMPLE 31

6-(((4-cyanophenyl)(1-methyl-1H-imidazol-5-yl)methoxy)methyl)-3'-methoxy(1,1'-biphenyl)-3-carbonitrile

EXAMPLE 31A

3'-methoxy-6-methyl(1,1'-biphenyl)-3-carbonitrile

A mixture of 3-chloro-4-methylbenzonitrile (3.30 g, 20 mmol), 3-methoxyphenylboronic acid (4.56 g, 30 mmol), palladium acetate (89.8 mg, 0.4 mmol), 2-dicyclohexylphosphanyl-2'-dimethylaminobiphenyl (0.236 g, 0.6 mmol), and CsF (9.11 g, 60 mmol) in dioxane (60 mL) at room temperature was stirred for 12 hours, and concentrated. The concentrate was dissolved in ethyl acetate (10 mL), washed with brine, dried (MgSO$_4$), filtered, and concentrated. The concentrate was purified by flash column chromatography on silica gel with 4:100 ethyl acetate/hexane to provide 4.38 g (98%) of the desired product. MS (DCI/NH$_3$) m/z 241 (M+NH$_4$)$^+$; $^1$H NMR (CDCl$_3$) δ 7.55–7.52 (m, 2H), 7.38–7.33 (m, 2H), 6.94 (m, 1H), 6.86 (m, 1H), 6.80 (m, 1H), 3.84 (s, 3H), 2.32 (s, 3H).

EXAMPLE 31B 6-(bromomethyl)-3'-methoxy(1,1'-biphenyl)-3-carbonitrile

A mixture of Example 31A (4.38 g, 19.6 mmol), N-bromosuccinimide (3.84 g, 21.5 mmol) and AIBN (0.2 g) in carbon tetrachloride (100 mL) was heated to reflux for 12 hours, filtered, and concentrated. The concentrate was purified by flash column chromatography on silica gel with 4:100 ethyl acetate/hexanes to provide 5.20 g (88%) of the desired product. MS (DCI/NH$_3$) m/z 320 (M+NH$_4$)$^+$; $^1$H NMR (CDCl$_3$) δ 7.66–7.63 (m, 2H), 7.57 (m, 1H), 7.39 (t, 1H), 7.01–6.94 (m, 3H), 4.22 (s, 2H), 3.86 (s, 3H).

EXAMPLE 31C 6-(((4-cyanophenyl)(1-methyl-1H-imidazol-5-yl)methoxy)methyl)-3'-methoxy(1,1'-biphenyl)-3-carbonitrile The desired product was prepared by substituting Example 31B for Example 1A in Example 1C. MS (ESI) m/z 435 (M+H)$^+$; $^1$H NMR (CDCl$_3$) δ 7.69–7.54 (m, 6H), 7.39–7.26 (m, 3H), 6.96 (m, 1H), 6.80–6.75 (m, 3H), 5.47 (s, 1H), 4.53 (d, 1H), 4.46 (d, 1H), 3.81 (s, 3H), 3.34 (s, 3H); Anal. Calcd for C$_{27}$H$_{22}$N$_4$O$_2$·0.50C$_4$H$_8$O$_2$: C, 72.79; H, 5.48; N, 11.71 Found: C, 72.71; H, 5.48; N, 11.79.

EXAMPLE 32

6-(((4-cyanophenyl)(1-methyl-1H-imidazol-5-yl)methoxy)methyl)-3'-ethoxy(1,1'-biphenyl)-3-carbonitrile

EXAMPLE 32A

3'-ethoxy-6-methyl(1,1'-biphenyl)-3-carbonitrile

A mixture of 3-chloro-4-methylbenzonitrile (3.03 g, 20 mmol), 3-ethoxyphenylboronic acid (4.98 g, 30 mmol), palladium acetate (74 mg, 0.4 mmol), 2-dicyclohexylphosphanyl-biphenyl (0.210 g, 0.6 mmol), and KF (3.48 g, 60 mmol) in THF (25 mL) at room temperature was stirred for 12 hours and concentrated. The concentrate was dissolved in ethyl acetate (10 mL), washed with brine, dried (MgSO$_4$), filtered, and concentrated. The concentrate was purified by flash column chromatography on silica gel with 4:100 ethyl acetate/hexanes to provide 4.68 g (99%) of the desired product. MS (DCI/NH$_3$) m/z 255 (M+NH$_4$)$^+$; $^1$H NMR (CDCl$_3$) δ 7.54–7.51 (m, 2H), 7.36–7.31 (m, 2H), 6.93 (m, 1H), 6.85–6.78 (m, 2H), 4.07 (q, 2H), 2.32 (s, 3H), 1.34 (t, 3H).

EXAMPLE 32B 6-(bromomethyl)-3'-ethoxy(1,1'-biphenyl)-3-carbonitrile

The desired product was prepared by substituting Example 32A for Example 31A in Example 31B. MS (DCI/NH$_3$) m/z 334 (M+NH$_4$)$^+$; $^1$H NMR (CDCl$_3$) δ 7.54–7.51 (m, 2H), 7.36–7.31 (m, 2H), 6.93 (m, 1H), 6.85–6.78 (m, 2H), 4.22 (s, 2H), 4.07 (q, 2H), 1.34 (t, 3H).

EXAMPLE 32C 6-(((4-cyanophenyl)(1-methyl-1H-imidazol-5-yl)methoxy)methyl)-3'-ethoxy(1,1'-biphenyl)-3-carbonitrile The desired product was prepared by substituting Example 32B for Example 1A in Example 1C. MS (ESI) m/z 449 (M+H)$^+$; $^1$H NMR (CDCl$_3$) δ 7.69–7.54 (m, 6H), 7.39–7.27 (m, 3H), 6.94 (m, 1H), 6.80–6.75 (m, 3H), 5.47 (s, 1H), 4.53 (d, 1H), 4.46 (d, 1H), 4.02 (q, 2H), 3.36 (s, 3H), 1.42 (t, 3H). Anal. Calcd for C$_{28}$H$_{24}$N$_4$O$_2$.0.27C$_4$H$_8$O$_2$: C, 73.95; H, 5.58; N, 11.86. Found: C, 73.78; H, 5.45; N, 11.86.

EXAMPLE 33

3-(1,3-benzodioxol-5-yl)-4-(((4-cyanophenyl)(1-methyl-1H-imidazol-5-yl)methoxy)methyl)benzonitrile

EXAMPLE 33A 3-(1,3-benzodioxol-5-yl)-4-methylbenzonitrile

The desired product was prepared by substituting 1,3-benzodioxol-5-ylboronic acid for 3-ethoxyphenylboronic acid in Example 32A. MS (DCI/NH$_3$) m/z 255 (M+NH$_4$)$^+$; $^1$H NMR (CDCl$_3$) δ 7.52–7.49 (m, 2H), 7.33 (d, 1H), 6.87 (d, 1H), 6.74–6.70 (m, 2H), 6.02 (s, 2H), 2.32 (s, 3H).

EXAMPLE 33B 3-(1,3-benzodioxol-5-yl)-4-(bromomethyl)benzonitrile

The desired product was prepared by substituting Example 33A for Example 31A in Example 31B. MS (DCI/NH$_3$) m/z 334 (M+NH$_4$)$^+$; $^1$H NMR (CDCl$_3$) δ 7.60 (m, 2H), 7.53 (m, 1H), 6.92–6.82 (m, 3H), 6.05 (s, 2H), 4.23 (s, 2H).

EXAMPLE 33C 3-(1,3-benzodioxol-5-yl)-4-(((4-cyanophenyl)(1-methyl-1H-imidazol-5-yl)methoxy)methyl)benzonitrile The desired product was prepared by substituting Example 33B for Example 1A in Example 1C. MS (DCI/NH$_3$) m/z 449 (M+H)$^+$; $^1$H NMR (CDCl$_3$) δ 7.67–7.55 (m, 6H), 7.41 (d, 2H), 6.83 (m, 2H), 6.70–6.51 (m, 2H), 6.04 (s, 2H), 5.51 (s, 1H), 4.53 (d, 1H), 4.46 (d, 1H), 3.38 (s, 3H); Anal. Calcd for C$_{27}$H$_{20}$N$_4$O$_3$.0.51C$_4$H$_8$O$_2$: C, 70.69; H, 4.92; N, 11.35. Found: C, 70.63; H, 4.87; N, 11.35.

EXAMPLE 34

3'-chloro-6-(((4-cyanophenyl)(1-methyl-1H-imidazol-5-yl)methoxy)methyl)(1,1'-biphenyl)-3-carbonitrile

EXAMPLE 34A

Methyl 3'-chloro-5-nitro(1,1'-biphenyl)-2-carboxylate

A mixture of methyl 2-chloro-4-nitrobenzoate (0.432 g, 2.0 mmol), 3-chlorophenylboronic acid (0.375 g, 2.4 mmol), trans-dichlorobis(tricyclohexylphosphine)-palladium (II) (0.074 g, 0.1 mmol), and sodium carbonate (0.64 g, 6.0 mmol) in a mixture of toluene (10 mL), dioxane (10 mL), and ethanol (2 mL) was heated to reflux for 12 hours, cooled to room temperature, diluted with ethyl acetate (10 mL), washed with brine, dried (MgSO$_4$), filtered, and concentrated. The concentrate was purified by flash column chromatography on silica gel with 1:10 ethyl acetate/hexanes to provide 0.58 g (99%) of the desired product. MS (DCI/NH$_3$) m/z 309 (M+NH$_4$)$^+$; $^1$H NMR (CDCl$_3$) δ 8.27–8.22 (m, 2H), 8.00 (dd, 1H), 7.41–7.34 (m, 3H), 7.23–7.18 (m, 1H), 3.72 (s, 3H).

EXAMPLE 34B

Methyl 5-amino-3'-chloro(1,1'-biphenyl)-2-carboxylate

A solution of Example 34A (0.57 g, 1.96 mmol) and 37% HCl (10 mL) in ethanol (20 mL) at room temperature was treated with tin dichloride dihydrate (1.76 g, 7.82 mmol), stirred for 4 hours, concentrated to remove the ethanol, cooled to 0° C., adjusted to pH 12 with 50% NaOH, and extracted with ethyl acetate. The combined extracts were washed with brine, dried (MgSO$_4$), filtered, and concentrated. The concentrate was purified by flash column chromatography on silica gel with 3:7 ethyl acetate/hexanes to provide 0.48 g (94%) of the desired product. MS (DCI/NH$_3$) m/z 262 (M+H)$^+$; $^1$H NMR (CDCl$_3$) δ 7.83 (m, 1H) 7.30–7.25 (m, 3H), 7.14 (m, 1H), 6.66 (m, 1H), 6.51 (m, 1H), 4.11 (br s, 2H), 3.61 (s, 3H).

EXAMPLE 34C

Methyl 3'-chloro-5-iodo(1,1'-biphenyl)-2-carboxylate

A solution of Example 34B (4.30 g, 16.5 mmol) in acetone (50 mL) at room temperature was treated with concentrated HCl (150 mL), cooled to 0° C., and treated dropwise with a solution of NaNO$_2$ (1.41 g, 20.5 mmol) in water (10 mL). The mixture was stirred at 0° C. for 1 hour, treated portionwise with a solution of KI (8.22 g, 49.5 mmol) in water (20 mL), stirred for 1 hour, and extracted with diethyl ether. The combined extracts were washed with Na$_2$S$_2$O$_5$ and brine, dried (MgSO$_4$), filtered, and concentrated The concentrate was purified by flash column chromatography on silica gel with 1:10 ethyl acetate/hexanes to provide 3.70 g (61%) of the desired product. MS (DCI/NH$_3$) m/z 390 (M+NH$_4$)$^+$; $^1$H NMR (CDCl$_3$) δ 7.81–7.72 (m, 2H), 7.59 (d, 1H), 7.38–7.28 (m, 3H), 7.15 (m, 1H), 3.66 (s, 3H).

EXAMPLE 34D

Methyl 3'-chloro-5-cyano(1,1'-biphenyl)-2-carboxylate

A solution of Example 34C (3.72 g, 10 mmol) in DMF (20 mL) was degassed with bubbling argon for 1 hour, treated with zinc cyanide (0.704 g, 6.0 mmol) and tetrakis (triphenylphosphine)palladium (0) (0.58 g, 0.5 mmol), and heated to 80° C. for 2 hours under a nitrogen atmosphere. The mixture was partitioned between ethyl acetate water, and the organic phase was washed with brine, dried (MgSO$_4$), filtered, and concentrated. The concentrate was purified by flash column chromatography on silica gel with 2:8 ethyl acetate/hexanes to provide 2.5 g (92%) of the desired product. MS (DCI/NH$_3$) m/z 289 (M+NH$_4$)$^+$; $^1$H NMR (CDCl$_3$) δ 7.92 (d, 1H), 7.74–7.66 (m, 2H), 7.39–7.29 (m, 3H), 7.18–7.14 (m, 1H), 3.70 (s, 3H).

EXAMPLE 34E

3'-chloro-6-(hydroxymethyl)(1,1'-biphenyl)-3-carbonitrile

A solution of CaCl$_2$ (2.04 g, 18.4 mmol) in ethanol (50 mL) at room temperature was treated with a solution of Example 34D (2.50 g, 9.2 mmol) in THF (50 mL), treated with NaBH$_4$ (1.39 g, 36.8 mmol), stirred for 24 hours, and concentrated. The concentrate was dissolved in ethyl acetate, washed with 5% HCl and brine, dried (MgSO$_4$), filtered, and concentrated. The concentrate was purified by flash column chromatography on silica gel with 3:7 ethyl acetate/hexanes to provide 2.1 g (90%) of the desired product. MS/(DCI/NH$_3$) m/z 261 (M+NH$_4$)$^+$; $^1$H NMR (CDCl$_3$) δ 7.77–7.67 (m, 3H), 7.53 (d, 1H), 7.43–7.39 (m, 2H), 7.31 (m, 1H), 7.19 (m, 1H), 4.66 (s, 2H).

EXAMPLE 34F 6-(bromomethyl)-3'-chloro(1,1'-biphenyl)-3-carbonitrile

A solution of Example 34E (2.43 g, 10 mmol) in DMF (20 mL) was treated with LiBr (1.0 g, 11.5 mmol), cooled to 0° C., treated with PBr$_3$ (7.85 g, 10.6 mmol), stirred for 1 hour, and warmed to room temperature. The mixture was partitioned between ethyl acetate and water, and the organic phase was washed with brine, dried (MgSO$_4$), filtered, and concentrated. The concentrate was purified by flash column chromatography on silica gel with 1:9 ethyl acetate/hexanes to provide 3.00 g (98%) of the desired product. MS (DCI/NH$_3$) m/z 324 (M+NH$_4$)$^+$; $^1$H NMR (CDCl$_3$) δ 7.68–7.62 (m, 2H), 7.53 (d, 1H), 7.45–7.40 (m, 3H), 7.31 (m, 1H), 4.38 (s, 2H).

EXAMPLE 34G

3'-chloro-6-(((4-cyanophenyl)(1-methyl-1H-imidazol-5-yl)methoxy)methyl)(1,1'-biphenyl)-3-carbonitrile The desired product was prepared by substituting Example 34F for Example 1A in Example 1C. MS (DCI/NH$_3$) m/z 439 (M+H)$^+$; $^1$H NMR (CDCl$_3$) δ 7.96 (br s, 1H), 7.71–7.57 (m, 5H), 7.40–7.35 (m, 4H), 7.27 (m, 1H), 7.10 (d, 1H), 6.89 (s, 1H), 5.50 (s, 1H), 4.48 (d, 1H), 4.43 (d, 1H), 3.43 (s, 3H); Anal. Calcd for C$_{26}$H$_{19}$ClN$_4$O.0.30C$_4$H$_8$O$_2$: C, 70.21; H, 4.64; N, 12.04. Found: C, 70.30; H, 4.60; N, 11.96.

EXAMPLE 35

4-(((6-chloro-2-(3-chlorophenyl)-3-pyridinyl)methoxy)(1-methyl-1H-imidazol-5-yl)methyl)benzonitrile

EXAMPLE 35A (2-chloro-3-pyridinyl)methanol

A solution of 2-chloronicotinic acid (2.0 g, 12.6 mmol) in THF (15 mL) at 0° C. was treated dropwise with 1M LAH in THF (15 mL, 15.0 mmol), warmed to room temperature, stirred for 5 hours, treated sequentially with water (0.5 mL), 40% NaOH solution (0.5 mL) and water (1.5 mL), stirred for 2 hours, filtered through a pad of diatomaceous earth (Celite®), and extracted with dichloromethane. The combined extracts were dried (MgSO$_4$), filtered, and concentrated to provide 1.56 g (87%) of the desired product of sufficient purity for subsequent use. MS (DCI/NH$_3$) m/z 144 (M+H)$^+$; $^1$H NMR (CDCl$_3$) δ 8.34 (dd, 1H), 7.90 (m, 1H), 7.29 (dd, 1H), 4.80 (s, 2H).

EXAMPLE 35B (2-(3-chlorophenyl)-3-pyridinyl)methanol

A suspension of Example 35A (1.56 g, 10.8 mmol) and 3-chlorophenylboronic acid (2.47 g, 15.8 mmol) in a mixture of toluene (10 mL), dioxane (10 mL), and 2N Na$_2$CO$_3$ (10 mL) was treated with tetrakis(triphenylphosphine) palladium (0) (0.61 g, 0.54 mmol), heated to 100° C. for 40 hours, cooled to room temperature, and extracted with ethyl acetate. The combined extracts were dried (MgSO$_4$), filtered, and concentrated. The concentrate was purified by flash column chromatography on silica gel with 1:1 ethyl acetate/hexanes to provide 1.32 g (56%) of the desired product. MS (DCI/NH$_3$) m/z 220 (M+H)$^+$; $^1$H NMR (CDCl$_3$) δ 8.59 (dd, 1H), 7.93 (m, 1H), 7.55 (s, 1H), 7.46–7.30 (m, 4H), 4.66 (s, 2H).

EXAMPLE 35C (2-(3-chlorophenyl)-1-oxido-3-pyridinyl)methanol

A solution of Example 35B (1.5 g, 6.8 mmol) in acetic acid (4 mL) at room temperature was treated with hydrogen peroxide (30% solution, 1.4 mL), heated to 60° C., stirred for 13 hours, adjusted to pH 7 with solid sodium hydroxide, washed with saturated sodium bisulfate, and extracted with dichloromethane. The combined extracts were dried (MgSO$_4$), filtered, and concentrated to provide the desired product of sufficient purity for subsequent use. MS (DCI/NH$_3$) m/z 237.

EXAMPLE 35D (6-chloro-2-(3-chlorophenyl)-3-pyridinyl)methanol

A solution of Example 35C (1.02 g, 4.3 mmol) in phosphorous oxychloride (5 mL) was heated to reflux for 18 hours, cooled to room temperature, treated with water, adjusted to pH>7 with K$_2$CO$_3$, and extracted with dichloromethane. The combined extracts were dried (MgSO$_4$), filtered, and concentrated. The concentrate was purified by flash column chromatography on silica gel with 2:1 hexanes/ethyl acetate to provide 340 mg (20%) of the desired product. MS (DCI/NH$_3$) m/z 255 (M+H)$^+$; $^1$H NMR (CDCl$_3$) δ 7.87 (d, 1H), 7.62 (m, 1H), 7.53–7.37 (m, 4H), 4.55 (s, 2H).

EXAMPLE 35E 3-(bromomethyl)-6-chloro-2-(3-chlorophenyl)pyridine

A solution of Example 35D (160 mg, 0.63 mmol) in DMF (2 mL) at room temperature was treated with PBr$_3$ (72 mL, 0.76 mmol) and lithium bromide (66 mg, 0.76 mmol), stirred for 3 hours, treated with water, adjusted to pH>7 with K$_2$CO$_3$, and extracted with dichloromethane. The combined extracts were dried (MgSO$_4$), filtered, and concentrated to provide 199 mg (quantitative) of the desired product of sufficient purity for subsequent use.

EXAMPLE 35F 4-(((6-chloro-2-(3-chlorophenyl)-3-pyridinyl)methoxy)(1-methyl-1H-imidazol-5-yl)methyl)benzonitrile The desired product was prepared by substituting Example 35E for Example 1A in Example 1C, and purifying the resulting product by flash column chromatography on silica gel with 10:0.4:0.1 ethyl acetate/methanol/ammonium hydroxide. The purified concentrate was dissolved in ethanol and treated with p-toluenesulfonic acid to provide the sulfonate salt. MS (DCI/NH$_3$) m/z 449 (M+H)$^+$; $^1$H NMR (CD$_3$OD) δ 8.88 (s, 1H), 8.01 (d, 1H), 7.75 (d, 2H), 7.69 (d, 2H), 7.51–7.37 (m, 6H), 7.22–7.19 (m, 4H), 5.87 (s, 1H), 4.65 (d, 1H), 4.53 (d, 1H), 3.72 (s, 3H), 2.36 (s, 3H); Anal. Calcd. for C$_{24}$H$_{18}$Cl$_2$N$_4$O.1.1(C$_7$H$_8$O$_3$S.H$_2$O): C, 57.97;H: 4.42; N: 8.53, Found: C: 57.95; H: 4.37; N: 8.22.

EXAMPLE 36

4-(((2-(3-chlorophenyl)-6-methyl-3-pyridinyl)
methoxy)(1-methyl-1H-imidazol-5-yl)methyl)
benzonitrile

EXAMPLE 36A 2-(3-chlorophenyl)-6-methylnicotinonitrile

A suspension of 2-chloro-6-methylnicotinonitrile (2.0 g, 13.1 mmol) and 3-chlorophenylboronic acid (3.0 g, 19.7 mmol) in a mixture of toluene (20 mL), dioxane (20 mL), and 2N $Na_2CO_3$ (20 mL) was treated with tetrakis(triphenylphosphine)-palladium (0) (0.76 g, 0.65 mmol), heated to reflux, stirred for 16 hours, cooled to room temperature, and extracted with dichloromethane. The combined extracts were dried ($MgSO_4$), filtered, and concentrated. The concentrate was purified by flash column chromatography on silica gel with 3:1 hexanes/ethyl acetate to provide 3.2 g (100%) of the desired product. MS (DCI/$NH_3$) m/z 229 (M+H)$^+$; $^1$H NMR (CDCl$_3$) δ 7.96 (d, 1H), 7.89 (m, 1H), 7.82 (m, 1H), 7.68–7.49 (m, 3H), 2.70 (s, 3H).

EXAMPLE 36B 2-(3-chlorophenyl)-6-methylnicotinic acid

A solution of Example 36A (0.5 g, 2.2 mmol) in ethylene glycol (12 mL) was treated with 40% KOH (15 mL), heated to 130° C. for 5 hours, diluted with water, adjusted to pH 5 with citric acid (7.0 g), saturated with NaCl, and extracted with ethyl acetate. The combined extracts were dried ($MgSO_4$), filtered, and concentrated to provide the desired product of sufficient purity for subsequent use. MS (DCI/$NH_3$) m/z 248 (M+H)$^+$; $^1$H NMR (CDCl$_3$) δ 8.13 (d, 1H), 7.54 (m, 1H), 7.41–7.30 (m, 3H), 7.23 (d, 1H), 2.65 (s, 3H).

EXAMPLE 36C (2-(3-chlorophenyl)-6-methyl-3-pyridinyl)methanol

A solution of Example 36B (3.0 g, 12.6 mmol) in THF (24 mL) at 0° C. was treated dropwise with 1M $BH_3$ in THF (24 mL, 24 mmol), heated to reflux for 16 hours, cooled to room temperature, quenched with methanol, stirred for 5 minutes, and concentrated. The concentrate was dissolved in ethanol (17 mL), treated with cesium fluoride (5.7 g, 36.0 mmol), heated to reflux for 14 hours, filtered, and concentrated to provide 732 mg (26%), of sufficient purity for subsequent use. MS (DCI/$NH_3$) m/z 234 (M+H)$^+$; $^1$H NMR (CDCl$_3$) δ 7.80 (d, 1H), 7.70–7.34 (m, 4H), 7.20 (d, 1H), 4.64 (d, 2H), 2.61 (s, 3H).

EXAMPLE 36D 3-(bromomethyl)-2-(3-chlorophenyl)-6-methylpyridine

A solution of Example 36C (230 mg, 1.0 mmol) in DMF (1.5 mL) at 0° C. was treated with $PBr_3$ (114 mL, 1.2 mmol) and lithium bromide (104 mg, 1.2 mmol), stirred for 3 hours, treated with water, adjusted to pH>7 with $K_2CO_3$, and extracted with dichloromethane. The combined extracts were dried ($MgSO_4$), filtered, and concentrated to provide the desired product of sufficient purity for subsequent use.

EXAMPLE 36E 4-(((2-(3-chlorophenyl)-6-methyl-3-pyridinyl)
methoxy)(1-methyl-1H-imidazol-5-yl)methyl)
benzonitrile The desired product was prepared by substituting Example 36D for Example 1A in Example 1C, then purifying the resulting product by flash column chromatography on silica gel with 10:0.4:0.1 ethyl acetate/methanol/ammonium hydroxide. The purified concentrate was dissolved in ethanol and treated with p-toluenesulfonic acid to provide the p-toluenesulfonate salt. MS (DCI/$NH_3$) m/z 429 (M+H)$^+$; $^1$H NMR (CD$_3$OD) δ 8.85 (s, 1H), 8.11 (d, 1H), 7.75 (d, 2H), 7.68 (d, 2H), 7.51–7.38 (m, 7H), 7.21 (d, 2H), 7.17 (m, 1H), 5.85 (s, 1H), 4.62 (d, 1H), 4.49 (d, 1H), 3.69 (s, 3H), 2.63 (s, 3H), 2.36 (s, 3H); Anal. Calcd. for $C_{25}H_{21}ClN_4O.1.6C_7H_8O_3S$: C, 61.72; H: 4.84; N: 7.95. Found:C: 61.50; H: 4.95; N: 8.14.

EXAMPLE 37

4-(3-(3',5-dichloro(1,1'-biphenyl)-2-yl)-1-hydroxy-1-
(1-methyl-1H-imidazol-5-yl)-2-propynyl)
benzonitrile

EXAMPLE 37A

3',5-dichloro(1,1'-biphenyl)-2-yl methyl ether

A suspension of 4-chloro-2-iodo-1-methoxybenzene (2.5 g, 9.3 mmol) and 3-chlorophenylboronic acid (2.2 g, 13.9 mmol) in a mixture of toluene (10 mL), dioxane (10 mL), and 2N $Na_2CO_3$ (10 mL) was treated with tetrakis(triphenylphosphine)-palladium (0) (0.54 g, 0.47 mmol), heated to reflux for 16 hours, cooled to room temperature, and extracted with ethyl acetate. The combined extracts were dried ($MgSO_4$), filtered, and concentrated. The concentrate was purified by flash column chromatography on silica gel with 20:1 hexanes/ethyl acetate to provide 2.5 g (100%) of the desired product. MS (DCI/$NH_3$) m/z 254 (M+H)$^+$; $^1$H NMR (CDCl$_3$) δ 7.75–7.23 (m, 6H), 6.91 (d, 1H), 3.80 (s, 3H).

EXAMPLE 37B

3',5-dichloro(1,1'-biphenyl)-2-ol

A solution of Example 37A (1.5 g, 5.9 mmol) in dichloromethane (925 mL) at room temperature was treated dropwise with 1M $BBr_3$ (17.8 mL, 17.8 mmol), stirred for 18 hours, and concentrated. The concentrate was purified by flash column chromatography on silica gel with 7:1 hexanes/ethyl acetate to provide 1.03 g (73%) of the desired product. MS (DCI/$NH_3$): m/z: 255 (M+$NH_4$)$^+$; $^1$H NMR (CDCl$_3$) δ 7.50–7.33 (m, 4H), 7.33–7.20 (m, 3H), 6.91 (m, 1H), 5.07 (br s, 1H).

EXAMPLE 37C

3',5-dichloro(1,1'-biphenyl)-2-yl trifluoromethanesulfonate

A solution of Example 37B (0.2 g, 0.83 mmol) and diisopropylethylamine (0.44 mL, 2.49 mmol) in dichloromethane (1 mL) at room temperature was treated with N-phenyl bis(trifluoromethanesulfonimide) (0.45 g, 1.25 mmol), stirred for 18 hours, washed with 3N HCl, dried ($MgSO_4$), filtered, and concentrated. The concentrate was purified by flash column chromatography with hexanes to provide 0.3 g (95%) of the desired product. MS (DCI/$NH_3$) m/z 388 (M+$NH_4$)$^+$; $^1$H NMR (CDCl$_3$) δ 7.60–7.19 (m, 7H).

EXAMPLE 37D 3,3'-dichloro-6-((trimethylsilyl)ethynyl)-1,1'-biphenyl

A solution of Example 37C (0.3 g, 0.79 mmol), trimethylsilylacetylene (0.17 mL, 1.2 mmol), and triethylamine (0.5 mL) in DMF (2.5 mL) was treated with tetrakis (triphenylphosphine)-palladium (0) (0.54 g, 0.47 mmol), heated to 70° C. for 2 hours, treated with water, and extracted with dichloromethane. The combined extracts were dried, filtered, and concentrated. The concentrate was purified by flash column chromatography on silica gel with hexanes to provide 115 mg (42%) of the desired product. MS (DCI/NH$_3$) m/z 336 (M+NH$_4$)$^+$; $^1$H NMR (CDCl$_3$) δ 7.63 (m, 1H), 7.52–7.38 (m, 3H), 7.37–7.32 (m, 3H), 0.15 (s, 9H).

EXAMPLE 37E 3,3'-dichloro-6-ethynyl-1,1'-biphenyl

A solution of Example 37D (0.11 g, 0.23 mmol) in methanol (4 mL) at room temperature was treated with 1N K$_2$CO$_3$ (0.5 mL, 0.5 mmol), stirred for 3 hours, and extracted with dichloromethane. The combined extracts were dried (MgSO$_4$), filtered, and concentrated. The concentrate was purified by flash column chromatography on silica gel with hexanes to provide 64 mg (79%) of the desired product. MS (DCI/NH$_3$) m/z 264 (M+NH$_4$)$^+$; $^1$H NMR (CDCl$_3$) δ 7.57–7.52 (m, 2H), 7.45 (m, 1H), 7.39–7.34 (m, 3H), 7.31 (dd, 1H), 3.10 (s, 1H).

EXAMPLE 37F 4-((1-methyl-1H-imidazol-5-yl)carbonyl) benzonitrile

A solution of Example 1B (0.86 g, 4.0 mmol) in dioxane (15 mL) at 45° C. was treated with manganese oxide (0.86 g, 9.9 mmol), heated to reflux for 5 hours, cooled to room temperature, and filtered through a pad of diatomaceous earth (Celite®) with ethyl acetate. The filtrate was concentrated, and the concentrate was purified by flash column chromatography on silica gel with 6:1 hexanes/ethyl acetate to provide 0.52 g (61%) of the desired product. MS (DCI/NH$_3$) m/z 212 (M+H)$^+$; $^1$H NMR (CDCl$_3$) δ 7.42–7.28 (m, 6H), 4.69 (s, 1.5H), 4.67 (s, 1.5H).

EXAMPLE 37G 4-(3-(3',5-dichloro(1,1'-biphenyl)-2-yl)-1-hydroxy-1-(1-methyl-1H-imidazol-5-yl)-2-propynyl) benzonitrile A solution of Example 37E (64 mg, 0.26 mmol) in THF (1 mL) at −78° C. was treated with 1.5M tert-butyllithium in pentane (0.18 mL, 0.26 mmol), stirred for 1 hour, treated dropwise with a solution of Example 37F (58 mg, 0.27 mmol) in THF (1 mL), warmed to room temperature over 16 hours, quenched with water, and extracted with ethyl acetate. The combined extracts were dried (MgSO$_4$), filtered, and concentrated. The concentrate was purified by flash column chromatography on silica gel with 10:0.6:0.1 ethyl acetate/methanol/ammonium hydroxide. The concentrate was dissolved in ethanol and treated with p-toluenesulfonic acid to provide the sulfonate salt. MS (DCI/NH$_3$) m/z 458 (M+H)$^+$; $^1$H NMR (CD$_3$OD) δ 8.86 (s, 1H), 7.77 (d, 2H), 7.69 (d, 2H), 7.64 (d, 2H), 7.51 (s, 1H), 7.48–7.34 (m, 5H), 7.22 (d, 2H), 7.06 (d, 1H), 3.31 (s, 3H), 2.36 (s, 3H); Anal. Calcd for C$_{26}$H$_{17}$N$_3$Cl$_2$O.1.5C$_7$H$_8$O$_3$S: C, 61.17; H, 4.08; N, 5.86, Found: C, 61.30; H, 4.32; N, 5.99.

EXAMPLE 38

4-(((4-(3-chlorophenyl)-6-fluoro-3-pyridinyl) methoxy)(1-methyl-1H-imidazol-5-yl)methyl) benzonitrile

EXAMPLE 38A 2-fluoro-4-iodo-5-methylpyridine

A solution of diisopropylamine (7.0 mL, 50.0 mmol) in THF (100 mL) at −78° C. was treated with 2.5M n-butyllithium in hexanes (20 mL, 50.0 mmol), stirred for 15 minutes, treated dropwise with a solution of 2-fluoro-5-methylpyridine (5.55 g, 50.0 mmol) in THF (20.0 mL), stirred for 4 hours, treated slowly with a solution of iodine (12.7 g. 50.0 mmol) in THF (50 mL), quenched with water, and extracted with diethyl ether. The combined extracts were washed sequentially with Na$_2$S$_2$O$_3$, water, and brine, dried (MgSO$_4$), filtered, and concentrated. The concentrate was purified by flash column chromatography on silica gel with 6:1 hexanes/diethyl ether to provide 7.24 g (61%) of 2-fluoro-3-iodo-5-methylpyridine.

A solution of diisopropylamine (4.3 mL, 30.5 mmol) in THF (50 mL) at −78° C. was treated with 2.5M n-butyllithium in hexanes (12.2 mL, 30.5 mmol), stirred for 30 minutes, treated dropwise with a solution of 2-fluoro-3-iodo-5-methylpyridine (7.24 g, 30.5 mmol) in THF (30 mL), stirred for 4 hours, quenched with water, and extracted with diethyl ether. The combined extracts were washed sequentially with Na$_2$S$_2$O$_3$, water, and brine, dried (MgSO$_4$), filtered, and concentrated to provide 6.3 g (87%) of the desired product. MS (DCI/NH$_3$) m/z 238 (M+H)$^+$; $^1$H NMR (CDCl$_3$) δ 7.99 (s, 1H), 7.43 (d, 1H), 2.38 (m, 3H).

EXAMPLE 38B 4-(3-chlorophenyl)-2-fluoro-5-methylpyridine

A mixture of Example 38A (5.90 g, 24.9 mmol), 3-chlorophenylboronic acid (5.80 g, 37.3 mmol), sodium carbonate (6.60 g, 62.3 mmol), and tetrakis (triphenylphosphine)palladium(0) (1.44 g, 1.25 mmol) in a mixture of ethanol (60 mL), toluene (60 mL), and water (20 mL) was heated to reflux for 1.5 hours, cooled to room temperature, and extracted with diethyl ether. The combined extracts were washed with water and brine, dried (MgSO$_4$), filtered, and concentrated. The concentrate was purified by flash chromatography on silica gel with 6:1 hexanes/diethyl ether to provide 4.41 g (80%) of the desired product. MS (DCI/NH$_3$) m/z 222 (M+H)$^+$; $^1$H NMR (CDCl$_3$) δ 8.01 (s, 1H), 7.32 (m, 2H), 7.32 (m, 1H), 7.20 (m, 1H), 6.80 (d, 1H), 2.23 (s, 3H).

EXAMPLE 38C 5-(bromomethyl)-4-(3-chlorophenyl)-2-fluoropyridine

A mixture of Example 38B (2.00 g, 9.00 mmol), N-bromosuccinimide (1.78 g, 9.90 mmol) and 2.2'-azobisisobutyronitrile (200 mg) in carbon tetrachloride (50 mL) was heated to reflux for 18 hours, cooled to room temperature, filtered, and concentrated. The concentrate was purified by a flash column chromatography on silica gel with 2.5:2 hexanes/ethyl acetate to provide 2.02 g (75%) of the desired product. MS (DCI/NH$_3$) m/z 300 (M+H)$^+$; $^1$H NMR (CDCl$_3$) δ 8.39 (s, 1H), 7.46 (m, 3H), 7.37 (m, 1H), 6.84 (d, 1H), 4.40 (s, 2H).

EXAMPLE 38D 4-(((4-(3-chlorophenyl)-6-fluoro-3-pyridinyl) methoxy)(1-methyl-1H-imidazol-5-yl)methyl) benzonitrile The desired product was prepared by substituting Example 38C for Example 1A in Example 1C. MS (DCI/NH$_3$) m/z 433 (M+H)$^+$; $^1$H NMR (CDCl$_3$) δ 8.27 (s, 1H), 7.62 (d, 2H), 7.38 (m, 6H), 7.20 (m, 1H), 6.89 (m, 2H), 5.50 (s, 1H), 4.48 (d, 1H), 4.40 (d, 1H), 3.29 (s, 3H); Anal. Calcd for C$_{24}$H$_{18}$N$_4$ClFO: C, 66.59; H, 4.19; N, 12.94. Found: C, 66.23; H, 4.20; N, 12.68.

EXAMPLE 39

4-(((4-(3-chlorophenyl)-6-methoxy-3-pyridinyl)methoxy)(1-methyl-1H-imidazol-5-yl)methyl)benzonitrile A solution of Example 38 (60 mg, 0.139 mmol) and 0.5M sodium methoxide in methanol (5.0 mL, 2.5 mmol) was heated to reflux for 4 hours, concentrated, dissolved in dichloromethane, washed with water, dried (MgSO$_4$), filtered, and concentrated. The concentrate was purified by flash column chromatography on silica gel with 20:1 dichloromethane/methanol to provide 27 mg (44%) of the desired product. MS (DCI/NH$_3$) m/z 445 (M+H)$^+$; $^1$H NMR (CDCl$_3$) δ 8.19 (s, 1H), 7.61 (d, 2H), 7.38 (m, 6H), 7.21 (m, 1H), 6.85 (s, 1H), 6.69 (s, 1H), 5.49 (s, 1H), 4.43 (d, 1H), 4.32 (d, 1H), 4.00 (s, 3H), 3.30 (s, 3H); Anal. Calcd for C$_{25}$H$_{21}$N$_4$ClO$_2$: C, 67.54; H, 4.67; N, 12.32. Found: C, 67.49; H, 4.76; N, 12.59.

EXAMPLE 40

4-(3-chlorophenyl)-5-(((4-cyanophenyl)(1-methyl-1H-imidazol-5-yl)methoxy)methyl)-2-pyridinecarbonitrile

EXAMPLE 40A 4-(3-chlorophenyl)-5-methyl-2-pyridinecarbonitrile

A mixture Example 38B (200 mg, 0.90 mmol) and sodium cyanide (44 mg, 1.0 mmol) in DMSO (4 mL) was heated to 80° C., stirred for 12 hours, poured into water, and extracted with diethyl ether. The combined extracts were washed with water and brine, dried (MgSO$_4$), filtered, and concentrated. The concentrate was purified by flash column chromatography on silica gel with 1:2 hexanes/diethyl ether to provide 48 mg (23%) of the desired product. MS (DCI/NH$_3$) m/z 229 (M+H)$^+$.

EXAMPLE 40B 5-(bromomethyl)-4-(3-chlorophenyl)-2-pyridinecarbonitrile

A mixture of Example 40A (48 mg, 0.211 mmol), N-bromosuccinimide (44 mg, 0.247 mmol), and 2,2'-azobisisobutyronitrile (5 mg) in carbon tetrachloride (2 mL) was heated to reflux for 3 hours, cooled to room temperature, filtered, and concentrated. The concentrate was purified by a flash column chromatography on silica gel with 2.5:2 hexanes/ethyl acetate to provide 53 mg (82%) of the desired product.

EXAMPLE 40C 4-(3-chlorophenyl)-5-(((4-cyanophenyl)(1-methyl-1H-imidazol-5-yl)methoxy)methyl)-2-pyridinecarbonitrile The desired product was prepared by substituting Example 40B for Example 1A in Example 1C. MS (ESI) m/z 440 (M+H)$^+$; $^1$H NMR (CDCl$_3$) δ 8.80 (s, 1H), 7.66 (d, 2H), 7.63 (s, 1H), 7.47 (m, 1H), 7.41 (d, 2H), 7.39 (m, 3H), 7.17 (m, 1H), 6.90 (s, 1H), 5.53 (s, 1H), 4.56 (d, 1H), 4.49 (d, 1H), 3.30 (s, 3H).

EXAMPLE 41

4-(3-chlorophenyl)-N-((4-cyanophenyl)(1-methyl-1H-imidazol-5-yl)methyl)-1-methyl-6-oxo-1,6-dihydro-3-pyridinecarboxamide

EXAMPLE 41A

Diethyl (2E)-3-(3-chlorophenyl)-2-pentenedioate

A mixture of diethyl glutaconate (10.0 g. 53.7 mmol), 3-chloroiodobenzene (11.5 g, 48.2 mmol), sodium acetate (4.40 g, 53.7 mmol) and palladium acetate (1.1 g, 4.9 mmol) in DMF (30 mL) was heated to 100° C., stirred for 21 hours, cooled to room temperature, poured into water, filtered, and extracted with ethyl acetate. The combined extracts were washed with water and brine, dried (MgSO$_4$), filtered, and concentrated. The concentrate was purified by flash column chromatography on silica gel 8:1 hexanes/ethyl acetate to provide 2.88 g (20%) of the desired product. MS (DCI/NH$_3$) m/z 297 (M+H)$^+$; $^1$H NMR (CDCl$_3$) δ 7.43 (m, 2H), 7.32 (m, 3H), 6.26 (s, 2H), 4.19 (m, 4H), 1.21 (t, 3H), 1.31 (t, 3H).

EXAMPLE 41B

Diethyl 3-(3-chlorophenyl)-4-(hydroxymethylene)-2-pentenedioate

A suspension of 60% NaH in oil (1.16 g, 29.0 mmol) in diethyl ether (15 mL) at room temperature was treated with ethyl formate (4.70 mL, 58.2 mmol), stirred for 2 hours, treated with a solution of Example 41A (2.88 g, 9.70 mmol) in diethyl ether (10 mL) over 40 minutes, stirred for 1 hour, pouted into ice cold 1N HCl, and extracted with diethyl ether. The combined extracts were washed with water and brine, dried (MgSO$_4$), filtered, and concentrated to provide 3.0 g (96%) of the desired product of sufficient purity for subsequent use.

EXAMPLE 41C

Ethyl 4-(3-chlorophenyl)-1-methyl-6-oxo-1,6-dihydro-3-pyridinecarboxylate

A mixture of Example 41B (1.50 g, 4.62 mmol), 2M methylamine in THF (3.5 mL, 7.0 mmol), and acetic acid (1.5 mL) in ethanol (20 mL) was heated to reflux for 30 minutes, cooled to room temperature, and concentrated. The concentrate was dissolved in acetonitrile (15 mL), treated with K$_2$CO$_3$ (3.2 g, 23.0 mmol), stirred for 18 hours, and concentrated. The concentrate was dissolved in dichloromethane, washed with water, dried (MgSO$_4$), filtered, and concentrated. The concentrate was purified by flash column chromatography on silica gel with 19:1 dichloromethane/acetone to provide 586 mg (41%) of the desired product. MS (DCI/NH$_3$) m/z 292 (M+H)$^+$; $^1$H NMR (CDCl$_3$) δ 8.22 (s, 1H), 7.35 (m, 2H), 7.23 (m, 1H), 7.12 (m, 1H), 6.43 (s, 1H), 4.09 (q, 2H), 3.65 (s, 3H), 1.04 (t, 3H).

EXAMPLE 41D 4-(3-chlorophenyl)-1-methyl-6-oxo-1,6-dihydro-3-pyridinecarboxylic acid A mixture of Example 41C (150 mg, 0.514 mmol) and LiOH.H$_2$O (180 mg, 4.29 mmol) in a mixture of THF (4 mL) and water (2 mL) was heated to 60° C., stirred for 8 hours, and concentrated to remove the THF. The remaining aqueous suspension was treated with water, filtered, and dried under vacuum to provide 105 mg (77%) of the desired product. MS (DCI/NH$_3$) m/z 264 (M+H)$^+$; $^1$H NMR (DMSO-d$_6$) δ 8.50 (s, 1H), 7.41 (m., 2H), 7.33 (m, 1H), 7.23 (m, 1H), 6.26 (s, 1H), 3.53 (s, 3H).

EXAMPLE 41E 4-(chloro(1-methyl-1H-imidazol-5-yl)methyl)benzonitrile

A solution of Example 1B (1.42 g, 6.66 mmol) in dichloromethane (40 mL) at 0° C. was treated with SOCl$_2$ (2.8 mL, 38.4 mmol), warmed to room temperature, stirred for 4 hours, and concentrated. The concentrate was azeotropically distilled with toluene to provide 2.0 g (quantitative) of the desired product of sufficient purity for subsequent use. $^1$H NMR (DMSO-d$_6$) δ 9.20 (s, 1H), 8.00 (d, 2H), 7.80 (d, 2H), 7.47 (s, 1H), 6.97 (s, 1H), 3.86 (s, 3H).

EXAMPLE 41F 4-(amino(1-methyl-1H-imidazol-5-yl)methyl) benzonitrile

A suspension of Example 41E (200 mg, 0.746 mmol) in THF (5 mL) at room temperature was treated dropwise with concentrated NH$_4$OH (2.0 mL), stirred for 2 hours, diluted with dichloromethane, washed with water, dried (MgSO$_4$), filtered, and concentrated to provide 123 mg (77%) of the desired product. MS (ESI) m/z 213 (M+H)$^+$; $^1$H NMR (CDCl$_3$) δ 7.65 (m, 2H), 7.48 (m, 2H), 7.39 (s, 1H), 6.84 (s, 1H), 5.26 (s, 1H), 3.49 (s, 3H).

EXAMPLE 41G 4-(3-chlorophenyl)-N-((4-cyanophenyl)(1-methyl-1H-imidazol-5-yl)methyl)-1-methyl-6-oxo-1,6-dihydro-3-pyridinecarboxamide A solution of Example 41D (50 mg, 0.190 mmol) in dichloromethane (2.0 mL) at 0° C. was treated with oxalyl chloride (50 mL, 0.573 mmol) and DMF (2 drops), stirred for 1 hour, warmed to room temperature, concentrated, and azeotropically distilled with toluene. The concentrate was dissolved in THF (2.0 mL), cooled to 0° C., treated with a solution of Example 41F (61 mg, 0.193 mmol) in THF (1.5 mL), warmed to room temperature over 18 hours, diluted with dichloromethane, washed with water, dried (MgSO$_4$), filtered, and concentrated. The concentrate was purified by flash column chromatography on silica gel with methyle 100:10:1 dichloromethane/methanol/acetic acid to provide 66 mg (67%) of the desired product. MS (ESI) m/z 458 (M+H)$^+$; $^1$H NMR (DMSO-d$_6$) δ 9.20 (d, 1H), 8.09 (s, 1H), 7.81 (d, 2H), 7.62 (s, 1H), 7.50 (d, 2H), 7.40 (m, 1H), 7.30 (t, 1H), 7.20 (m, 4H), 6.34 (s, 1H), 6.25 (s, 1H), 6.21 (d, 1H), 3.54 (s, 3H), 3.51 (s, 3H), 1.89 (s, 3H).

EXAMPLE 42

1-(3-chlorophenyl)-6-(((4-cyanophenyl)(1-methyl-1H-imidazol-5-yl)methoxy)methyl)-4-oxo-1,4-dihydro-3-pyridinecarbonitrile

EXAMPLE 42A 3-((dimethylamino)methylene)-6-methyl-2H-pyran-2,4(3H)-dione

A suspension of 2-hydroxy-6-methyl-4H-pyran-4-one (23.92 g, 0.189 mmol) and dimethylformamide dimethyl acetal (45.2 mL, 0.34 mmol) in toluene (100 mL) was stirred at room temperature for 4 hours and concentrated to provide 25.8 g (75%) of the desired product of sufficient purity for subsequent use. MS (DCI/NH$_3$) m/z 182 (M+H)$^+$; $^1$H NMR (CDCl$_3$) δ 8.22 (s, 1H), 5.67 (s, 1H), 3.47 (s, 3H), 3.39 (s, 3H), 2.13 (s, 3H).

EXAMPLE 42B 1-(3-chlorophenyl)-6-methyl-4-oxo-1,4-dihydro-3-pyridinecarboxylic acid A suspension of Example 42A (10.0 g, 55.2 mmol) in ethanol (500 mL) at room temperature was treated with 3-chloroaniline (7.34 mL, 69.4 mmol) and sodium tert-butoxide (16.0 g, 167 mmol), heated to 90° C., stirred for 18 hours, cooled to room temperature, and concentrated. The concentrate was treated with water (600 mL) and 3N HCl (57 mL), filtered, and dried under vacuum to provide 11.38 g (78%) of the desired product of sufficient purity for subsequent use. MS (DCI/NH$_3$) m/z 264 (M+H)$^+$; $^1$H NMR (DMSO-d$_6$) δ 16.19 (s, 1H), 8.48 (s, 1H), 7.86 (m, 1H), 7.69 (m, 1H), 7.52 (m, 2H), 6.87 (s, 1H), 2.12 (s, 3H).

EXAMPLE 42C 1-(3-chlorophenyl)-6-methyl-4-oxo-1,4-dihydro-3-pyridinecarboxamide A mixture of Example 42B (5.00 g, 19.0 mmol) and 1,1-carbonyldiimidazole (7.70 g, 43.1 mmol) in DMF (70 mL) was heated to 110° C., stirred for 18 hours, cooled to 0° C., treated with bubbling NH$_3$ for 15 minutes, cooled to 4° C. for 18 hours, and filtered. The solid was washed with dichloromethane and hexanes, then dried under vacuum to provide 4.5 g (91%) of the desired product. MS (DCI/NH$_3$) m/z 263 (M+H)$^+$; $^1$H NMR (DMSO-d$_6$) δ 8.9.44 (br d, 1H), (s, 1H), 8.22 (s, 1H), 7.82 (m, 1H), 7.60 (m, 3H), 7.55 (br d, 1H), 6.49 (d, 1H), 2.04 (d, 3H).

EXAMPLE 42D 1-(3-chlorophenyl)-6-methyl-4-oxo-1,4-dihydro-3-pyridinecarbonitrile A solution of Example 42C (600 mg, 2.23 mmol) in NMP (10.0 mL) at room temperature was slowly treated with POCl$_3$ (2.0 mL, 21.5 mmol), stirred for 3 hours, quenched with water, adjusted to pH>7 with saturated K$_2$CO$_3$, and extracted with ethyl acetate. The combined extracts were washed with water and brine, dried (MgSO$_4$), filtered, and concentrated. The concentrate was purified by flash column chromatography on silica gel with 55:45 ethyl acetate/dichloromethane to provide 210 mg (38%) of the desired product. MS (DCI/NH$_3$) m/z 245 (M+H)$^+$; $^1$H NMR (CDCl$_3$) δ 7.81 (s, 1H), 7.58 (m, 1H), 7.52 (d, 1H), 7.37 (m, 1H), 7.24 (m, 1H), 6.43 (s, 1H), 2.07 (s, 3H).

EXAMPLE 42E 6-(bromomethyl)-1-(3-chlorophenyl)-4-oxo-1,4-dihydro-3-pyridinecarbonitrile A suspension of Example 42D (210 mg, 0.858 mmol) and N-bromosuccinimide (150 mg, 0.843 mmol) in carbon tetrachloride (5 mL) was treated with benzoyl peroxide (110 mg, 0.454 mmol), heated to reflux, stirred for 18 hours, and concentrated. The concentrate was purified by flash column chromatography on silica gel 75:25/dichloromethane/ethyl acetate to provide 13 mg (5%) of the desired product. MS (DCI/NH$_3$) m/z 323 (M+H)$^+$; $^1$H NMR (CDCl$_3$) δ 7.83 (s, 1H), 7.63 (m, 1H), 7.56 (m, 1H), 7.49 (m, 1H), 7.38 (m, 1H), 6.67 (s, 1H), 4.00 (s, 2H).

EXAMPLE 42F 1-(3-chlorophenyl)-6-(((4-cyanophenyl)(1-methyl-1H-imidazol-5-yl)methoxy)methyl)-4-oxo-1,4-dihydro-3-pyridinecarbonitrile A mixture of Example 42E (13 mg, 0.04 mmol), Example 1B (20 mg, 0.09 mmol), and silver(I) oxide (43 mg, 0.18 mmol) in dichloromethane (2 mL) at room temperature was stirred for 18 hours, filtered and concentrated. The concentrate was purified by flash column chromatography on silica gel with 93:1:1 dichloromethane/methanol/NH$_4$OH to provide 8 mg (44%) of the desired product. MS (ESI) m/z 456 (M+H)$^+$; $^1$H NMR (CDCl$_3$) δ 7.82 (s, 1H), 7.64 (d, 2H), 7.58 (d. 1H), 7.50 (t, 1H), 7.43 (br s 1H), 7.37 (m, 1H), 7.31 (d, 2H), 7.23 (m, 1H), 6.94 (br s, 1H), 6.67 (s, 1H), 5.43 (br s, 1H), 4.14 (d, 1H), 4.07 (d1H), 3.25 (s, 3H).

EXAMPLE 43

5-(3-chlorophenyl)-6-(((4-chlorophenyl)(1-methyl-1H-imidazol-5-yl)methoxy)methyl)-1methyl-2-oxo-1,2-dihydro-3-pyridinecarbonitrile

EXAMPLE 43A 5-bromo-6-methyl-2-oxo-1,2-dihydro-3-pyridinecarbonitrile

A mixture of 6-methyl-2-oxo-1,2-dihydro-3-pyridinecarbonitrile (26.23 g, 95.5 mmol) and N-bromosuccinimide (36.54 g, 205 mmol) in 1,2-dichloroethane (500 mL) heated to reflux for 18 hours, cooled to room temperature, and filtered. The solid was treated with water (1 L), stirred for 2 hours, filtered, washed with water, and dried under vacuum to provide 36.85 g (88%) of the desired product of sufficient purity for subsequent use. MS (DCI/NH$_3$) m/z 230 (M+NH$_4$)$^+$; $^1$H NMR (DMSO-d$_6$) δ 12.96 (br s, 1H), 8.34 (s, 1H),2.36 (s, 3H).

EXAMPLE 43B 5-bromo-1,6-dimethyl-2-oxo-1,2-dihydro-3-pyridinecarbonitrile

A mixture of Example 43A (10.0 g, 46.9 mmol), cesium carbonate (15.3 g, 79.3 mmol) and methyl iodide (3.2 mL, 51.4 mmol) in DMF (100 mL) was heated to 70° C. for 1 hour, diluted with dichloromethane, washed with water, dried (MgSO$_4$), filtered, and concentrated. The concentrate was purified by flash column chromatography on silica gel with 98:2 dichloromethane/ethyl acetate to provide 5.10 g (48%) of the desired product. MS (DCI/NH$_3$) m/z: 244 (M+NH$_4$)$^+$; $^1$H NMR (DMSO-d$_6$) δ 8.40 (s, 1H), 3.57 (s, 3H), 2.60 (s, 3H).

EXAMPLE 43C 5-(3-chlorophenyl)-1,6-dimethyl-2-oxo-1,2-dihydro-3-pyridinecarbonitrile A mixture of Example 43B (2.90 g, 12.8 mmol), 3-chlorophenylboronic acid (3.99 g, 25.54 mmol), tetrakis(triphenylphosphine)palladium (0) (0.738 g, 0.639 mmol), lithium chloride (1.62 g, 38.2 mmol), and Na$_2$CO$_3$ (4.06 g, 38.3 mmol) in a mixture of water (20 ml), toluene (20 ml), and ethanol (20 ml) was heated to reflux for 24 hours, cooled to room temperature, diluted with ethyl acetate (10 mL), washed with brine, dried (MgSO$_4$), filtered, and concentrated. The concentrate was purified by flash column chromatography on silica gel with 1:1 ethyl acetate/hexanes to provide 3.1 g (94%) of the desired product. MS (DCI/NH$_3$) m/z 259 (M+H)$^+$; $^1$H NMR (CDCl$_3$) δ 7.68 (s, 1H), 7.40–7.38 (m, 2H), 7.22–7.20 (m, 1H), 7.11–7.08 (m, 1H), 3.77 (s, 3H), 2.38 (s, 3H).

EXAMPLE 43D 6-(bromomethyl)-5-(3-chlorophenyl)-1-methyl-2-oxo-1,2-dihydro-3-pyridinecarbonitrile A mixture of Example 43C (3.20 g, 12.4 mmol), N-bromosuccinimide (4.44 g, 24.8 mmol), and benzoyl peroxide (0.1 g, 0.41 mmol) in carbon tetrachloride (100 mL) was heated to reflux for 24 hours, filtered, and concentrated. The concentrate was purified by flash column chromatography on silica gel with 93:7 ethyl acetate/hexanes to provide 3.80 g (80%) of the desired product. MS (DCI/NH$_3$) m/z 355 (M+NH$_4$)$^+$; $^1$H NMR (CDCl$_3$) δ 7.70 (s, 1H), 7.46–7.32 (m, 2H), 7.38–7.37 (m, 1H), 7.29–7.25 (m, 1H), 4.26 (s, 2H), 3.76 (s, 3H).

EXAMPLE 43E 5-(3-chlorophenyl)-6-(hydroxymethyl)-1-methyl-2-oxo-1,2-dihydro-3-pyridinecarbonitrile A mixture of Example 43D (2.30 g, 6.7 mmol) and CaCO$_3$ (3.4 g, 33.8 mmol) in a mixture of water (50 mL) and dioxane (100 mL) was heated to reflux for 12 hours, cooled to room temperature, and concentrated. The concentrate was partitioned between water and ethyl acetate, and adjusted to pH 4 with 1N HCl. The aqueous phase was extracted with ethyl acetate and the combined organic phases were washed with brine, dried (MgSO$_4$), filtered, and concentrated. The concentrate was purified by flash column chromatography on silica gel with 1:1 ethyl acetate/hexanes to provide 1.25 g (67%) of the desired product. MS (DCI/NH$_3$) m/z 292 (M+NH$_4$)$^+$; $^1$H NMR (DMSO-d$_6$) δ 7.75 (s, 1H), 7.42–7.40 (m, 2H), 7.32–7.31 (m, 1H), 7.21–7.18 (m, 1H), 4.59 (d, 2H), 3.83 (s, 3H), 2.45 (t, 1H).

EXAMPLE 43F (4-chlorophenyl)(1-methyl-1H-imidazol-5-yl)methanol

The desired product was prepared by substituting 4-chlorobenzaldehyde for 4-cyanobenzaldehyde in Example 1B.

EXAMPLE 43G 5-(3-chlorophenyl)-6-(((4-chlorophenyl)(1-methyl-1H-imidazol-5-yl)methoxy)methyl)-1-methyl-2-oxo-1,2-dihydro-3-pyridinecarbonitrile A mixture Example 43F (100 mg, 0.45 mmol), Example 43E (0.1 mg, 0.37 mmol), and p-toluenesulfonic acid (0.1 g) in benzene (20 mL) was heated to reflux for 10 hours under Dean-Stark conditions, diluted with ethyl acetate (10 mL), washed with 2M Na$_2$CO$_3$ and brine, dried (MgSO$_4$), filtered, and concentrated. The concentrate was purified by preparative HPLC with 0.1:100 trifluoroacetic acid/acetonitrile to provide 30 mg (17%) of the desired product. MS (ESI) m/z 479 (M+H)$^+$; $^1$H NMR (CD$_3$OD) δ 8.75 (s, 1H), 8.01 (s, 1H), 7.41–7.26 (m, 8H), 7.15–7.10 (m, 1H), 5.77 (s, 1H), 4.64–4.47 (m, 2H), 3.76 (s, 3H), 3.66 (s, 3H).

EXAMPLE 44

4-(((4-(3-chlorophenyl)-6-oxo-1,6-dihydro-3-pyridinyl)methoxy)(1-methyl-1H-imidazol-5-yl)methyl)benzonitrile Example 38D (156 mg, 0.36 mmol) was treated with acetic acid (20 mL) and water (5 mL), heated to 90° C. for 12 hours, cooled to room temperature, and concentrated. The concentrate was treated with 2M Na$_2$CO$_3$ and extracted with ethyl acetate. The combined extracts were dried over (MgSO$_4$), filtered, and concentrated to provide the desired product as the acetic acid salt. MS (APCI) m/z 431 (M+H)$^+$; $^1$H NMR (MeOH-d$_4$): δ 7.88 (s, 1H), 7.67–7.69 (dd, 2H), 7.57 (s, 1H), 7.47–7.39 (m, 3H), 7.34 (d, 2H), 7.28 (dt, 1H), 6.79(s, 1H), 6.40 (s, 1H), 5.62 (s, 1H), 4.35 (d, 1H), 4.25 (d, 1H), 3.41 (s, 3H), 3.66 (s, 3H).

EXAMPLE 45

4-(((4-(3-chlorophenyl)-1-methyl-6-oxo-1,6-dihydro-3-pyridinyl)methoxy)(1-methyl-1H-imidazol-5-yl)methyl)benzonitrile A solution of Example 44 (0.041 g, 0.1 mmol) in DMF (1.0 mL) at 0° C. was treated with 60% NaH in mineral oil (4 mg, 0.1 mmol), stirred for 15 minutes, treated with a 0° C. solution of iodomethane (15.6 mg, 0.11 mmol) in DMF (0.5 mL), stirred for 30 minutes, diluted with ethyl acetate, washed with water and brine, dried ($MgSO_4$), filtered, and concentrated. The concentrate was purified by flash column chromatography on silica gel with 10:1:0.1 EtOAc:MeOH:$NH_4OH$ to provide the desired product. MS (APCI) m/z 431 (M+H)$^+$; $^1$H NMR(MeOH-$d_4$) δ 8.92 (s, 1H), 8.19 (s, 1H), 7.73 (d, 2H), 7.50–7.41 (m, 5H), 7.32 (d, 1H), 7.24 (s, 1H), 6.67 (s, 1H), 5.86 (s, 1H), 4.52 (d, 1H), 4.40 (d, 1H), 3.79 (s, 3H), 3.67 (s, 3H).

EXAMPLE 46

N-(5-cyano-2-(((4-cyanophenyl)(1-methyl-1H-imidazol-5-yl)methoxy)methyl)phenyl)-2-thiophenesulfonamide

EXAMPLE 46A 1-(bromomethyl)-4-iodo-2-nitrobenzene

The desired product was prepared by substituting 4-iodo-1-methyl-2-nitrobenzene for Example 31A in Example 31B.

EXAMPLE 46B 4-(((4-iodo-2-nitrobenzyl)oxy)(1-methyl-1H-imidazol-5-yl)methyl)benzonitrile The desired product was prepared by substituting Example 46A for Example 1A in Example 1C.

EXAMPLE 46C 4-(((2-amino-4-iodobenzyl)oxy)(1-methyl-1H-imidazol-5-yl)methyl)benzonitrile A solution of Example 46B (0.8 g, 2.1 mmol) in methanol (50 mL) at room temperature was treated with $SnCl_2 \cdot 2H_2O$ (1.41 g, 6.3 mmol) and concentrated HCl (20 mL), stirred for 12 hours, and concentrated. The concentrate was treated with aqueous NaOH and extracted with ethyl acetate. The combined extracts were washed with brine, dried ($MgSO_4$), filtered, and concentrated. The concentrate was purified by flash column chromatography on silica gel with $CH_2Cl_2$:$CH_3OH$:$NH_4OH$ (100:3:3, v/v) to provide the desired product. MS (DCI/$NH_3$) m/z 445 (M+H)$^+$.

EXAMPLE 46D

N-(2-(((4-cyanophenyl)(1-methyl-1H-imidazol-5-yl)methoxy)methyl)-5-iodophenyl)-2-thiophenesulfonamide A solution of Example 46C (0.1 g, 0.23 mmol) in dichloromethane (5 mL) at room temperature was treated with 2-thiophenesulfonyl chloride (0.043 g, 0.24 mmol) and pyridine (0.2 mL), stirred for 2 days, and purified by flash column chromatography on silica gel with $CH_2Cl_2$:$CH_3OH$:$NH_4OH$ (100:3:3, v/v) to provide the desired product. MS (DCI/$NH_3$) m/z 590 (M+H)$^+$.

EXAMPLE 46E

N-(5-cyano-2-(((4-cyanophenyl)(1-methyl-1H-imidazol-5-yl)methoxy)methyl)phenyl)-2-thiophenesulfonamide A solution of Example 46D (0.10 g, 0.17 mmol) in DMF (2 mL) was treated with Zn(CN)$_2$ (11 mg, 0.093 mmol), Pd(PPh$_3$)$_4$ (10.8 mg, 0.00935 mmol), flushed with nitrogen, heated at 80° C. for 5 hours, cooled to room temperature, diluted with ethyl acetate, washed with water and brine, dried ($MgSO_4$), filtered, and concentrated. The concentrate was purified by flash column chromatography on silica gel with $CH_2Cl_2$:$CH_3OH$:$NH_4OH$ (100:3:3, v/v) to provide the desired product.MS (ESI) m/z 490 (M+H)$^+$; $^1$H NMR (CDCl$_3$) δ 7.72–7.69 (m, 3H), 7.60–7.57 (m, 2H), 7.47–7.42 (m, 4H), 7.30 (d, 1H), 7.06–7.01 (m, 2H), 5.79 (s, 1H), 4.45(d, 1H), 4.43 (d, 1H), 3.37 (s, 3H).

EXAMPLE 47

N-(5-cyano-2-(((4-cyanophenyl)(1-methyl-1H-imidazol-5-yl)methoxy)methyl)phenyl)-4-methylbenzenesulfonamide The desired compound was prepared by substituting 4-toulenesulfonyl chloride for 2-thiophenesulfonyl chloride in Example 46. MS (ESI) m/z 498 (M+H)$^+$; $^1$H NMR (CDCl$_3$) δ 7.72–7.69 (m, 3H), 7.53–7.47 (m, 6H), 7.38 (dd, 1H), 7.24–7.19 (m, 3H), 7.00 (s, 1H), 5.55 (s,1H), 4.48 (d, 1H), 4.37 (d, 1H), 3.36 (s, 3H), 2.40 (s, 3H).

EXAMPLE 48

5-(3-chlorophenyl)-6-(((4-cyanophenyl)(1-methyl-1H-imidazol-5-yl)methoxy)methyl)-1-methyl-2-oxo-1,2-dihydro-3-pyridinecarbonitrile A solution of Example 43E (1.0 g, 3.64 mmol) and Example 1B (776 mg, 3.64 mmol) in toluene (20 mL) was treated with p-toluenesulfonic acid (1.04 g, 5.46 mmol), heated to reflux for 5 hours under Dean-Stark conditions, and cooled to room temperature. The remaining toluene was decanted leaving a thick oil which was dissolved in ethyl acetate with a minimal amount of methanol. The resulting solution was washed sequentially with saturated NaHCO$_3$, water, and brine, dried (MgSO$_4$), filtered, and concentrated. The concentrate was purified by flash column chromatography on silica gel with dichloromethane then 99:1 to 49:1 dichloromethane/methanol to provide the desired product. MS (ESI) m/z 470 (M+H)$^+$; $^1$H NMR (300 MHz, CD$_3$OD) δ 8.01 (s, 1H), 7.70 (d, 2H), 7.56 (s, 1H), 7.44 (d, 2H), 7.36–7.30 (m, 3H), 7.16–7.13 (s, 1H), 6.71 (s, 1H), 5.69 (s, 1H), 4.53 (q, 2H), 3.78 (s, 3H), 3.37 (s, 3H).

EXAMPLE 49

6-(((4-cyanophenyl)(1-methyl-1H-imidazol-5-yl)methoxy)methyl)-5-(3,5-difluorophenyl)-1-methyl-2-oxo-1,2-dihydro-3-pyridinecarbonitrile

EXAMPLE 49A 5-bromo-6-(bromomethyl)-1-methyl-2-oxo-1,2-dihydro-3-pyridinecarbonitrile The desired product was prepared by substituting Example 43B for Example 43C in Example 43D. MS (ESI)

m/z 305 (M+H)$^+$; $^1$H NMR (300 MHz, CD$_3$OD) δ 8.27 (s, 1H), 4.81 (s, 2H), 3.76 (s, 3H).

EXAMPLE 49B 5-bromo-6-(hydroxymethyl)-1-methyl-2-oxo-1,2-dihydro-3-pyridinecarbonitrile The desired product was prepared by substituting Example 49A for Example 43D in Example 43E. MS (ESI) m/z 243 (M+H)$^+$; $^1$H NMR (500 MHz, DMSO-d$_6$) δ 8.43 (s, 1H), 5.86 (t, 1H), 4.65 (d, 2H), 3.63 (s, 3H).

EXAMPLE 49C 5-(3,5-difluorophenyl)-6-(hydroxymethyl)-1-methyl-2-oxo-1,2-dihydro-3-pyridinecarbonitrile The desired product was prepared by substituting Example 49B and 3,5-difluorphenylboronic acid for Example 43B and 3-chlorophenylboronic acid, respectively, in Example 43C.

EXAMPLE 49D 6-(4-cyanophenyl)(1-methyl-1H-imidazol-5-yl)methoxy)methyl)-5-(3,5-difluorophenyl)-1-methyl-2-oxo-1,2-dihydro-3-pyridinecarbonitrile The desired product was prepared by substituting Example 49C for Example 43E in Example 48. A solution of the purified product in 4M HCl in dioxane (2 mL) was stirred for 1 hour and concentrated. The concentrate was treated with water (2 mL) and lyophilized to provide the hydrochloride salt. MS (ESI) m/z 472 (M+H)$^+$; $^1$H NMR (300 MHz, DMSO-d$_6$) δ 8.97 (s, 1H), 8.20 (s, 1H), 7.84 (d, 2H), 7.48 (d, 2H), 7.35–7.23 (m, 2H), 7.15–6.95 (m, 2H), 5.96 (s, 1H), 4.52 (dd, 2H), 3.65 (s, 3H), 3.59 (s, 3H).

EXAMPLE 50

6-(((4-cyanophenyl)(1-methyl-1H-imidazol-5-yl)methoxy)methyl)-1-methyl-2-oxo-5-(3-(trifluoromethoxy)phenyl)-1,2-dihydro-3-pyridinecarbonitrile

EXAMPLE 50A 1,6-dimethyl-2-oxo-5-(3-(trifluoromethoxy)phenyl)-1,2-dihydro-3-pyridinecarbonitrile The desired product was prepared by substituting 3-trifluoromethoxyphenylboronic acid for 3-chlorophenylboronic acid in Example 43C. $^1$H NMR (500 MHz, CDCl$_3$) δ 7.70 (s, 1H), 7.51–7.47 (m, 1H), 7.29–7.25 (m, 1H), 7.17–7.14 (m, 1H), 7.08–7.07 (m, 1H), 3.68 (s, 3H), 2.38 (s, 3H).

EXAMPLE 50B 6-(bromomethyl)-1-methyl-2-oxo-5-(3-(trifluoromethoxy)phenyl)-1,2-dihydro-3-pyridinecarbonitrile The desired product was prepared by substituting Example 50A for Example 43C in Example 43D. $^1$H NMR (500 MHz, CDCl$_3$) δ 7.71 (s, 1H), 7.54 (t, 1H), 7.35–7.31 (m, 2H), 7.28–7.26 (m, 1H), 4.24 (2H), 3.79 (s, 3H).

EXAMPLE 50C 6-(hydroxymethyl)-1-methyl-2-oxo-5-(3-(trifluoromethoxy)phenyl)-1,2-dihydro-3-pyridinecarbonitrile The desired product was prepared by substituting Example 50B for Example 43D in Example 43E. MS (ESI) m/z 325 (M+H)$^+$; $^1$H NMR (400 MHz, CDCl$_3$) δ 7.70 (s, 1H), 7.46–7.41 (m, 1H), 7.25–7.21 (m, 1H), 7.19–7.16 (m, 1H), 7.13–7.11 (m, 1H), 4.51 (s, 2H), 3.77(s, 3H).

EXAMPLE 50D 6-(((4-cyanophenyl)(1-methyl-1H-imidazol-5-yl)methoxy)methyl)-1-methyl-2-oxo-5-(3-(trifluoromethoxy)phenyl)-1,2-dihydro-3-pyridinecarbonitrile The desired product was prepared by substituting Example 50C for Example 43E in Example 48. MS (ESI) m/z 520 (M+H)$^+$; $^1$H NMR (300 MHz, CD$_3$OD) δ 8.04 (s, 1H), 7.70–7.66 (m, 2H), 7.55–7.41 (m, 4H), 7.36–7.31 (m, 1H), 7.27–7.24 (m, 1H), 7.18–7.15 (m, 1H), 6.69–6.68 (m, 1H), 5.68 (s, 1H), 4.55 (abq, 2H), 3.78 (3H), 3.35 (s, 3H).

EXAMPLE 51

6-(((4-cyanophenyl)(1-methyl-1H-imidazol-5-yl)methoxy)methyl)-5-(3,5-dichlorophenyl)-1-methyl-2-oxo-1,2-dihydro-3-pyridinecarbonitrile

EXAMPLE 51A 5-(3,5-dichlorophenyl)-6-(hydroxymethyl)-1-methyl-2-oxo-1,2-dihydro-3-pyridinecarbonitrile The desired product was prepared by substituting 3,5-dichlorophenylboronic acid and Example 49B for 3-chlorophenylboronic acid and Example 43B, respectively, in Example 43C.

EXAMPLE 51B 6-(((4-cyanophenyl)(1-methyl-1H-imidazol-5-yl)methoxy)methyl)-5-(3,5-dichlorophenyl)-1-methyl-2-oxo-1,2-dihydro-3-pyridinecarbonitrile The desired product was prepared by substituting Example 51A for Example 43E in Example 48. MS (ESI) m/z 504 (M+H)$^+$; $^1$H NMR (300 MHz, DMSO-d$_6$) δ 8.20 (s, 1H), 7.78 (d, 2H), 7.63 (dd, 1H), 7.56 (dd, 1H), 7.41 (d, 2H), 7.45 (d, 2H), 6.49 (d, 1H), 5.77 (s,1H), 4.42 (q, 2H), 3.64 (s, 3H), 3.38 (s, 3H); Anal. calcd for C$_{26}$H$_{19}$Cl$_2$N$_5$O$_2$ 0.45CH$_2$Cl$_2$: C, 58.55; H, 3.70; N, 12.91. Found: C, 58.55; H, 3.57; N, 12.72.

EXAMPLE 52

5-(3-chlorophenyl)-6-(((4-cyano-3-fluorophenyl)(1-methyl-1H-imidazol-5-yl)methoxy)methyl)-1-methyl-2-oxo-1,2-dihydro-3-pyridinecarbonitrile

EXAMPLE 52A

Methyl 4-cyano-3-fluorobenzoate

A solution of 4-bromo-2-fluorobenzonitrile (10.0 g, 0.05 mol) in methanol (150 mL) was treated with (1,1'-bis(diphenylphosphino)ferrocene)dichloropalladium(II) complex with dichloromethane (1:1) (0.408 g, 0.5 mmol) and triethylamine (13.9 mL), heated to 115° C. under 450 psi CO pressure for 24 hours, cooled to room temperature, filtered, and concentrated to provide the desired product of sufficient purity for subsequent use without further purification.

EXAMPLE 52B 2-fluoro-4-(hydroxymethyl)benzonitrile

A solution of Example 52A (1.0 g, 5.58 mmol) in THF (20 mL) at room temperature was treated with a solution of CaCl$_2$ (1.24 g, 11.16 mmol) in ethanol (20 mL). The resulting solution was treated with NaBH$_4$ (845 mg, 22.33 mmol) over 20 minutes, stirred for 1.25 hours, then slowly quenched with saturated ammonium chloride (100 mL), and concentrated. The remaining aqueous portion was extracted with ethyl acetate (3×100 mL) and the combined extracts were dried (MgSO$_4$), filtered, and concentrated to provide the desired product. MS (APCI) m/z 169 (M+NH$_4$)$^+$; $^1$H NMR (300 MHz, CDCl$_3$) δ 7.60 (t, 1H), 7.29–7.23 (m, 2H), 4.80 (s, 2H).

EXAMPLE 52C 2-fluoro-4-formylbenzonitrile

A solution of Example 52B (1.23 g, 8.17 mmol) in 1,4-dioxane (30 mL) was treated with MnO$_2$, heated to 100° C. for 1 hour, and cooled to room temperature. The cooled solution was filtered through diatomaceous earth (Celite®) on a fritted funnel rinsing with 1:1 dichloromethane/methanol (200 mL). The filtrate was concentrated and the concentrate was purified by flash column chromatography on silica gel with a solvent gradient of 19:1 to 4:1 hexanes/ethyl acetate to provide the desired product. MS (APCI) m/z 149 (M+H)$^+$; $^1$H NMR (300 MHz, CDCl$_3$) δ 10.06 (s, 1H), 7.88–7.71 (m, 3H).

EXAMPLE 52D 2-fluoro-4-(hydroxy(1-methyl-1H-imidazol-5-yl)methyl)benzonitrile A solution of 5-iodo-1-methyl-1H-imidazole (250 mg, 1.2 mmol) in dichloromethane (2 mL) at 0° C. was treated with 3M phenylmagnesium bromide in diethyl ether (0.4 mL, 1.2 mmol), stirred for 30 minutes, warmed to room temperature, stirred for 30 minutes, cooled to 0° C. and treated with a solution of Example 52C (150 mg, 1.0 mmol) in dichloromethane (1 mL). The mixture was warmed to room temperature, stirred for 2 days, and quenched with ethyl acetate and saturated ammonium chloride. The aqueous phase was extracted with ethyl acetate (2×100 mL), and the combined organic layers were dried (MgSO$_4$), filtered, and concentrated. The concentrate was dissolved in 1:1 ethyl acetate/diethyl ether, filtered, rinsed with 1:1 ethyl acetate/diethyl ether and dried to provide the desired product. $^1$H NMR (400 MHz, CD$_3$OD) δ 7.91 (dd, 1H), 7.56 (s, 1H), 7.51 (d, 1H), 7.42–7.38 (m, 1H), 6.42 (s, 1H), 6.28–6.24 (m, 1H), 5.93–5.91 (m, 1H), 3.52 (s, 3H).

EXAMPLE 52E 5-(3-chlorophenyl)-6-(((4-cyano-3-fluorophenyl)(1-methyl-1H-imidazol-5-yl)methoxy)methyl)-1-methyl-2-oxo-1,2-dihydro-3-pyridinecarbonitrile The desired product was prepared by substituting Example 52D for Example 1B in Example 48. MS (ESI) m/z 488 (M+H)$^+$; $^1$H NMR (500 MHz, CD$_3$OD) δ 8.01 (s, 1H), 7.74–7.71 (m, 1H), 7.57 (s, 1H), 7.42–7.35 (m, 2H), 7.31–7.24 (m, 3H), 7.17–7.15 (m, 1H), 6.75 (s, 1H), 5.72 (s, 1H), 4.55 (q, 2H), 3.78 (s, 3H), 3.38 (s, 3H).

EXAMPLE 53

5-(3-chlorophenyl)-6-(((4-cyano-2-fluorophenyl)(1-methyl-1H-imidazol-5-yl)methoxy)methyl)-1-methyl-2-oxo-1,2-dihydro-3-pyridinecarbonitrile

EXAMPLE 53A 4-(bromomethyl)-3-fluorobenzonitrile

The desired product was prepared by substituting 3-fluoro-4-methylbenzonitrile for Example 43C in Example 43D. $^1$H NMR (300 MHz, CDCl$_3$) δ 7.56–7.36 (m, 3H), 4.50–4.49 (m, 2H).

EXAMPLE 53B 3-fluoro-4-(hydroxymethyl)benzonitrile

The desired product was prepared by substituting Example 53A for Example 43D in Example 43E. MS (APCI) m/z 169 (M+NH$_4$)$^+$; $^1$H NMR (300 MHz, CDCl$_3$) δ 7.64–7.58 (m, 1H), 7.29–7.22 (m, 2H), 4.79 (s, 2H).

EXAMPLE 53C 3-fluoro-4-formylbenzonitrile

A solution of Example 53B (340 mg, 2.25 mmol) in dichloromethane (10 mL) at room temperature was treated with Dess-Martin periodinane (1.9 g, 4.5 mmol), stirred for 5 minutes, and concentrated. The concentrate was dissolved in ethyl acetate, washed with saturated sodium bicarbonate, dried (MgSO$_4$), filtered, and concentrated. The concentrate was purified by flash column chromatography on silica gel with 10:1 hexanes/ethyl acetate to provide the desired product. $^1$H NMR (500 MHz, CDCl$_3$) δ 10.42 (s, 1H), 8.01 (dd, 1H), 7.62–7.58 (m, 1H), 7.54 (dd, 1H);

EXAMPLE 53D 3-fluoro-4-(hydroxy(1-methyl-1H-imidazol-5-yl)methyl)benzonitrile The desired product was prepared by substituting Example 53C for Example 52C in Example 52D. $^1$H NMR (400 MHz, CDCl$_3$) δ 8.44 (s, 1H), 7.93 (t, 1H), 7.61 (dd, 1H), 7.42 (dd, 1H), 6.69 (s, 1H), 6.15 (s, 1H), 4.89 (s, 3H).

EXAMPLE 53E 5-(3-chlorophenyl)-6-(((4-cyano-2-fluorophenyl)(1-methyl-1H-imidazol-5-yl)methoxy)methyl)-1-methyl-2-oxo-1,2-dihydro-3-pyridinecarbonitrile The desired product was prepared by substituting Example 53D for Example 1B in Example 48MS (ESI) m/z 488 (M+H)$^+$; $^1$H NMR (300 MHz, CD$_3$OD) δ 8.02 (s, 1H), 7.64–7.51 (m, 4H), 7.43–7.29 (m, 3H), 7.17–7.13 (m, 1H), 6.63 (s, 1H), 5.88 (s, 1H), 4.59 (q, 2H), 3.77 (s, 3H), 3.51 (s, 3H).

EXAMPLE 54

6-(((3-chloro-4-cyanophenyl)(1-methyl-1H-imidazol-5-yl)methoxy)methyl)-5-(3-chlorophenyl)-1-methyl-2-oxo-1,2-dihydro-3-pyridinecarbonitrile

EXAMPLE 54A 2-chloro-4-iodobenzonitrile

A solution of 4-amino-2-chlorobenzonitrile (30.5 g, 0.2 mol) in 1:1 diethyl ether/3M HCl (600 mL) at 0° C. was treated dropwise over 15 minutes with a solution of sodium nitrite (18 g, 0.26 mol) in water (100 mL), stirred 15 minutes, then treated with a solution of potassium iodide (50 g, 0.3 mol) in water (50 mL) dropwise over 45 minutes, warmed to room temperature, and stirred for 1.5 hours. The organic phase was washed with water (3×100 mL) and the combined aqueous layers were extracted with diethyl ether. The combined organic layers were combined, washed sequentially with saturated NaHCO$_3$, 25% Na$_2$S$_2$O$_3$, and

EXAMPLE 54B

Methyl 3-chloro-4-cyanobenzoate

The desired product was prepared by substituting Example 54A for 4-bromo-2-fluorobenzonitrile in Example 52A.

EXAMPLE 54C 2-chloro-4-(hydroxymethyl)benzonitrile

The desired product was prepared by substituting Example 54B for Example 52A in Example 52B.

EXAMPLE 54D 2-chloro-4-formylbenzonitrile

The desired product was prepared by substituting Example 54C for Example 52B in Example 52C.

EXAMPLE 54E 2-chloro-4-(hydroxy(1-methyl-1H-imidazol-5-yl)methyl)benzonitrile The desired product was prepared by substituting Example 54D for 4-cyanobenzaldehyde in Example 1B. MS (ESI) m/z 248 (M+H)$^+$.

EXAMPLE 54F 6-(((3-chloro-4-cyanophenyl)(1-methyl-1H-imidazol-5-yl)methoxy)methyl)-5-(3-chlorophenyl)-1-methyl-2-oxo-1,2-dihydro-3-pyridinecarbonitrile The desired product was prepared by substituting Example 54E for Example 43E in Example 48. The crude product was purified by preparative HPLC with 0.1:100 trifluoroacetic acid/acetonitrile to provide the desired product. MS (ESI) m/z 504 (M+H)$^+$; $^1$H NMR (500 MHz, CD$_3$OD) δ 8.88 (s, 1H), 8.01 (s, 1H), 7.81 (d, 1H), 7.57 (d, 1H), 7.46–7.35 (m, 4H), 7.28–7.27 (m, 1H), 7.16–7.14 (m, 1H), 5.82 (s, 1H), 4.65 (dd, 2H), 3.78 (s, 3H), 3.67 (s, 3H).

EXAMPLE 55

3-(1,3-benzodioxol-5-yl)-4-(2-(4-cyanophenyl)-2-hydroxy-2-(1-methyl-1H-imidazol-5-yl)ethoxy)benzonitrile

EXAMPLE 55A 3-bromo-4-(ethoxymethoxy)benzonitrile

A solution of 3-bromo-4-hydroxybenzonitrile (25 g, 125 mmol) in THF (375 mL) at room temperature was treated with 95% NaH (4.3 g, 170 mmol) in a few portions. The resulting slurry was heated to 60° C. for 30 minutes, treated with chloromethyl ethyl ether (25 g, 260 mmol), and the mixture was stirred at 60° C. for another 2 hours. The reaction was cooled to room temperature, concentrated to a slush, treated with water (200 mL), and filtered. The solid was dried for about 16 hours under vacuum in the presence of P$_2$O$_5$ to provide 30 g (95%) of the desired product. MS (DCI/NH$_3$) m/z 273, 275 (M+H+NH$_3$)$^+$; $^1$H NMR (CDCl$_3$) δ 7.84 (d, 1H), 7.56 (dd, 1H), 7.25 (d, 1H), 5.35 (s, 2H), 3.76 (q, 2H), 1.23 (t, 3H).

EXAMPLE 55B 3-(1,3-benzodioxol-5-yl)-4-(ethoxymethoxy)benzonitrile

A mixture of Example 55A (2.6 g, 10 mmol), 3,4-(methylenedioxy)phenylboronic acid, toluene (40 mL), and 2M aqueous Na$_2$CO$_3$ (40 mL) was purged with nitrogen, treated with tetrakis(triphenylphosphine)palladium(0) (0.45 g, 0.39 mmol), heated to reflux for about 16 hours, cooled to room temperature, then partitioned between water and ethyl acetate. The organic phase was washed with 2M Na$_2$CO$_3$, and brine, dried (Na$_2$SO$_4$), filtered, and concentrated. The concentrate was purified by flash column chromatography on silica gel with 85:15 hexanes/ethyl acetate to provide 2.8 g (95%) of the desired product. MS (DCI/NH$_3$) m/z 315 (M+H+NH$_3$)$^+$; $^1$H NMR (CDCl$_3$) δ 7.56 (m, 2H), 7.30 (d, 1H), 6.97 (d, 1H), 6.90 (d, 1H), 6.88 (s, 1H), 6.01 (s, 2H), 5.25 (s, 2H), 3.68 (q, 2H), 1.20 (t, 3H).

EXAMPLE 55C 3-(1,3-benzodioxol-5-yl)-4-hydroxybenzonitrile

A solution of Example 55B (2.8 g, 9.5 mmol) in THF (35 mL), water (7 mL), MeOH (3 mL), and 37% HCl (2 mL) was heated to reflux for 75 minutes, cooled to room temperature, concentrated, and partitioned between water and ethyl acetate. The organic phase was washed with brine, dried (Na$_2$SO$_4$), filtered, and concentrated to provide 2.2 g (97%) of the desired product. MS (DCI/NH$_3$) m/z 257 (M+H+NH$_3$)$^+$; $^1$H NMR (CDCl$_3$) δ 7.53 (dd, 1H), 7.51 (s, 1H), 7.03 (d, 1H), 6.95 (d, 1H), 6.87 (m, 2H), 6.04 (s, 2H).

EXAMPLE 55D 3-(1,3-benzodioxol-5-yl)-4-(2-(4-cyanophenyl)-2-oxoethoxy)benzonitrile A mixture of 4-cyanophenacyl bromide (2.7 g, 12 mmol), Example 55C (2.2 g, 9.2 mmol), and K$_2$CO$_3$ (1.8 g, 13 mmol) in DMF (20 mL) was stirred at room temperature under a drying tube for 2.5 hours, and partitioned between water and ethyl acetate. The organic phase was washed with brine and the combined aqueous phases were extracted with ethyl acetate. The combined organic phases were dried (Na$_2$SO$_4$), filtered, and concentrated. The concentrate was purified by flash column chromatography on silica gel with 70:30 hexanes/ethyl acetate to provide 2.9 g (86%) of the desired product. MS (DCI/NH$_3$) m/z 400 (M+H+NH$_3$)$^+$; $^1$H NMR (CDCl$_3$) δ 7.98 (m, 2H), 7.75 (m, 2H), 7.60 (d, 1H), 7.55 (dd, 1H), 6.98 (m, 1H), 6.90 (dd, 1H), 6.87 (d, 1H), 6.84 (d, 1H), 6.01 (s, 2H), 5.32 (s, 2H).

EXAMPLE 55E 3-(1,3-benzodioxol-5-yl)-4-(2-(4-cyanophenyl)-2-hydroxy-2-(1-methyl-1H-imidazol-5-yl)ethoxy)benzonitrile A solution of 1-methyl-2-(triethylsilyl)-1H-imidazole (2.0 g, 10 mmol) in THF (25 mL) at −78° C. was treated dropwise with 1.7M tert-butyllithium in pentane (6.0 mL, 10.2 mmol), stirred for 30 minutes, then added (all at once) to a solution of Example 55D (2.9 g, 7.6 mmol) in THF (25 mL), and stirred for 1 hour. The mixture was quenched with methanol (2 mL), treated with 1.0M tetrabutylammonium fluoride in THF (10 mL), and warmed to room temperature. After 1 hour the reaction was partitioned between water and ethyl acetate. The organic phase was washed with brine, dried ($Na_2SO_4$), filtered, and concentrated. The concentrate was purified by trituration with ethyl acetate to provide 1.5 g (42%) of the free base. The solid was slurried in $CH_3CN$ (20 mL), treated with 2N HCl (3 mL), concentrated, dissolved in water (50 mL), cooled to freezing, and lyophilized to provide the hydrochloride salt. MS (ESI) m/z 465 $(M+H)^+$; $^1H$ NMR (DMSO-$d_6$) δ 9.05 (s, 1H), 7.99 (d, 1H), 7.80 (dd, 1H), 7.75 (d, 2H), 7.67 (d, 1H), 7.46 (d, 2H), 7.44 (d, 1H), 7.11(s, 1H), 6.90 (d,1H), 6.83 (d, 1H), 6.79 (dd, 1H), 6.10 (d, 2H), 4.75 (d, 1H), 4.60 (d, 1H), 3.40 (s, 3H-under water peak); Anal. Calcd. for $C_{27}H_{21}ClN_4O_4$.1.00$H_2O$: C, 62.49; H, 4.47; N, 10.80. Found: C, 62.31; H, 4.28; N, 10.75.

EXAMPLE 56

3-(1,3-benzodioxol-5-yl)-4-(2-(4-cyanophenyl)-2-fluoro-2-(1-methyl-1H-imidazol-5-yl)ethoxy)benzonitrile A solution of (diethylamino)sulfur trifluoride (1.8 mL, 2.4 g, 14.8 mmol) in dichloromethane (160 mL) at −10° C. was treated with Example 55E (1.1 g, 2.4 mmol), stirred for 1 hour, poured onto ice, then partitioned between 2M $Na_2CO_3$, isopropanol, and dichloromethane. The organic phase was washed with brine, dried ($Na_2SO_4$), filtered, and concentrated. The concentrate was purified by flash column chromatography on silica gel with 98.5:1.5:0.25 ethyl acetate/ethyl acetate/conc. $NH_4OH$ to provide 0.94 g (85%) of the free base. The solid was slurried in $CH_3CN$ (20 mL), treated with 2N HCl (3 mL), concentrated, dissolved in water (50 mL), cooled to freezing, and lyophilized to provide the hydrochloride salt. MS (ESI) m/z 467 $(M+H)^+$; $^1H$ NMR (DMSO-$d_6$) δ 9.12 (s, 1H), 8.11 (m, 1H), 7.90 (d, 2H), 7.85 (dd, 1H), 7.70 (d, 1H), 7.49 (d, 3H), 6.90 (d,1H), 6.72 (dd, 1H), 6.68 (d, 1H), 6.10 (m, 2H), 5.08, 5.00 (both m, total 2H), 3.45 (s, 3H); Anal. Calcd. for $C_{27}H_{20}ClFN_4O_3$.0.90$H_2O$: C, 62.47; H, 4.23; N, 10.79. Found: C, 62.50; H, 4.48; N, 10.76.

EXAMPLE 57

6-(2-(4-cyanophenyl)-2-hydroxy-2-(1-methyl-1H-imidazol-5-yl)ethoxy)-3'-methoxy-1,1'-biphenyl-3-carbonitrile

EXAMPLE 57A 6-(ethoxymethoxy)-3'-methoxy-1,1'-biphenyl-3-carbonitrile

The desired product was prepared by substituting 3-methoxyphenylboronic acid for 3,4-(methylenedioxy)phenylboronic acid in Example 55B. MS (DCI/$NH_3$) m/z 301 $(M+H+NH_3)^+$; $^1H$ NMR (CDCl$_3$) δ 7.61 (d, 1H), 7.60 (dd, 1H), 7.36 (d, 1H), 7.32 (m, 1H), 7.03 (m, 1H), 7.00 (m, 1H), 6.92 (m, 1H), 5.25 (s, 2H), 3.85 (s, 3H), 3.68 (q, 2H), 1.20 (t, 3H).

EXAMPLE 57B 6-hydroxy-3'-methoxy-1,1'-biphenyl-3-carbonitrile

The desired product was prepared by substituting Example 57A for Example 55B in Example 55C. MS (DCI/$NH_3$) m/z 243 $(M+H+NH_3)^+$; $^1H$ NMR (CDCl$_3$) δ 7.57 (m, 2H), 7.45 (dd, 1H), 7.06 (d, 1H), 7.00 (m, 2H), 6.92 (m, 1H), 5.81 (s, 1H), 3.87 (s, 3H).

EXAMPLE 57C 6-(2-(4-cyanophenyl)-2-oxoethoxy)-3'-methoxy-1,1'-biphenyl-3-carbonitrile The desired product was prepared by substituting Example 57B for Example 55C in Example 55D. MS (DCI/$NH_3$) m/z 386 $(M+H+NH_3)^+$; $^1H$ NMR (CDCl$_3$) δ 7.95 (m, 2H), 7.72 (m, 2H), 7.63 (d, 1H), 7.58 (dd, 1H), 7.32 (dd, 1H), 7.03 (m, 2H), 6.94 (m, 1H), 6.90 (d, 1H), 5.30 (s, 2H), 3.83 (s, 3H).

EXAMPLE 57D 6-(2-(4-cyanophenyl)-2-hydroxy-2-(1-methyl-1H-imidazol-5-yl)ethoxy)-3'-methoxy-1,1'-biphenyl-3-carbonitrile The desired product was prepared by substituting Example 57C for Example 55D in Example 55E. MS (APCI) m/z 451 $(M+H)^+$; $^1H$ NMR (DMSO-$d_6$) δ 9.03 (s, 1H), 7.96 (d, 1H), 7.83 (dd, 1H), 7.72 (d, 1H), 7.64 (d, 2H), 7.41 (d, 1H), 7.33 (d, 2H), 7.28 (dd, 1H), 7.11 (s, 1H), 6.96 (dd, 1H), 6.92 (dd, 1H), 6.82 (d, 1H), 4.71 (d, 1H), 4.54 (d, 1H), 3.79 (s, 3H), 3.35 (s, 3H-under water peak); Anal. Calcd. for $C_{27}H_{23}ClN_4O_3$.0.95$H_2O$: C, 64.34; H, 4.98; N, 11.11. Found: C, 64.27; H, 4.83; N, 11.12.

EXAMPLE 58

6-(2-(4-cyanophenyl)-2-fluoro-2-(1-methyl-1H-imidazol-5-yl)ethoxy)-3'-methoxy-1,1'-biphenyl-3-carbonitrile The desired product was prepared by substituting Example 57D for Example 55E in Example 56. MS (ESI) m/z 453 $(M+H)^+$; $^1H$ NMR (DMSO-$d_6$) δ 8.99 (s, 1H), 8.02 (d, 1H), 7.87 (dd, 1H), 7.82 (d, 2H), 7.74 (d, 1H), 7.48 (d, 1H), 7.40 (d, 2H), 7.25 (dd, 1H), 6.94 (dd, 1H), 6.82 (dd, 1H), 6.78 (d, 1H), 5.03 (s, 1H), 4.96 (s, 1H), 3.77 (s, 3H), 3.40 (s, 3H-under water peak); Anal. Calcd. for $C_{27}H_{22}ClFN_4O_2$.1.65$H_2O$: C, 62.52; H, 4.92; N, 10.80. Found: C, 62.49; H, 4.72; N, 10.64.

EXAMPLE 59

4-(2-(4-cyanophenyl)-2-hydroxy-2-(1-methyl-1H-imidazol-5-yl)ethoxy)-3-quinolin-8-ylbenzonitrile

EXAMPLE 59A 4-(ethoxymethoxy)-3-quinolin-8-ylbenzonitrile

The desired product was prepared by substituting 8-quinolineboronic acid for 3,4-(methylenedioxy)phenylboronic acid and adding ethanol (25 mL) and LiCl (1.0 g, 23 mmol) to the reaction in Example 55B. Purification by flash column chromatography on silica gel with 2:1 hexanes/ethyl acetate provided the desired product. MS (DCI/$NH_3$) m/z 305 $(M+H)^+$; $^1H$ NMR (CDCl$_3$) δ 8.86 (dd, 1H), 8.20 (dd, 1H), 7.88 (dd, 1H), 7.70 (m, 2H), 7.63 (m, 2H), 7.43 (m, 1H), 7.38 (m, 1H), 5.10 (s, 2H), 3.52 (q, 2H), 1.12 (t, 3H).

EXAMPLE 59B 4-hydroxy-3-quinolin-8-ylbenzonitrile

The desired product was prepared by substituting Example 59A for Example 55B in Example 55C. MS (DCI/NH$_3$) m/z 247 (M+H)$^+$; $^1$H NMR (CDCl$_3$) δ 8.93 (dd, 1H), 8.40 (dd, 1H), 7.98 (dd, 1H), 7.88 (dd, 1H), 7.75 (m, 2H), 7.65 (dd, 1H), 7.60 (dd, 1H), 7.20 (d, 1H).

EXAMPLE 59C 4-(2-(4-cyanophenyl)-2-oxoethoxy)-3-quinolin-8-ylbenzonitrile

The desired product was prepared by substituting Example 59B for Example 55C in Example 55D. Purification by flash column chromatography on silica gel with 1:1 hexanes/ethyl acetate provided the desired product. MS (DCI/NH$_3$) m/z 390 (M+H)$^+$; $^1$H NMR (CDCl$_3$) δ 8.80 (dd, 1H), 8.20 (dd, 1H), 7.87 (dd, 1H), 7.68 (m, 4H), 7.48 (m, 2H), 7.45 (d, 2H), 7.40 (dd, 1H), 7.03 (d, 1H), 5.11 (s, 2H).

EXAMPLE 59D 4-(2-(4-cyanophenyl)-2-hydroxy-2-(1-methyl-1H-imidazol-5-yl)ethoxy)-3-quinolin-8-ylbenzonitrile The desired product was prepared by substituting Example 59C for Example 55D in Example 55E. MS (APCI) m/z 472 (M+H)$^+$; $^1$H NMR (DMSO-d$_6$) δ 8.99 (s, 1H), 8.85 (dd, 1H), 8.70 (br d, 1H), 8.20 (d, 1H), 7.96 (dd, 1H), 7.74 (m, 3H), 7.65 (m, 2H), 7.44 (d, 1H), 7.27 (d, 2H), 7.00 (br s, 1H), 6.69 (d, 2H), 4.65 (d, 1H), 4.38 (d, 1H), 3.18 (s, 3H); Anal. Calcd. for C$_{29}$H$_{23}$Cl$_2$N$_5$O$_2$.2.30H$_2$O: C, 59.45; H, 4.75; N, 11.95. Found: C, 59.47; H, 4.76; N, 11.78.

EXAMPLE 60

4-(2-(4-cyanophenyl)-2-fluoro-2-(1-methyl-1H-imidazol-5-yl)ethoxy)-3-quinolin-8-ylbenzonitrile The desired product was prepared by substituting Example 59D for Example 55E in Example 56. MS (APCI) m/z 474 (M+H)$^+$; $^1$H NMR (DMSO-d$_6$) δ 9.12 (s, 1H), 8.86 (d, 1H), 8.78 (m, 1H), 8.21 (d, 1H), 8.00 (m, 2H), 7.75 (m, 3H), 7.63 (d, 1H), 7.54 (d, 1H), 7.47 (d, 2H), 6.83 (d, 2H), 4.90 (m, 2H), 3.20 (s, 3H); Anal. Calcd. for C$_{29}$H$_{22}$Cl$_2$FN$_5$O.1.85H$_2$O: C, 60.08; H, 4.47; N, 12.08. Found: C, 60.07; H, 4.42; N, 12.13.

EXAMPLE 61

6-(2-(4-cyanophenyl)-2-hydroxy-2-(1-methyl-1H-imidazol-5-yl)ethoxy)-3',4'-difluoro-1,1'-biphenyl-3-carbonitrile

EXAMPLE 61A 6-(ethoxymethoxy)-3',4'-difluoro-1,1'-biphenyl-3-carbonitrile

The desired product was prepared by substituting 3,4-difluorophenylboronic acid for 3,4-(methylenedioxy)phenylboronic acid in Example 55B. MS (DCI/NH$_3$) m/z 307 (M+H+NH$_3$)$^+$; $^1$H NMR (CDCl$_3$) δ 7.62 (dd, 1H), 7.56 (d, 1H), 7.33 (m, 1H), 7.32 (d, 1H), 7.27 (m 1H), 7.18 (m, 1H), 5.28 (s, 2H), 3.68 (q, 2H), 1.20 (t, 3H).

EXAMPLE 61B

3',4'-difluoro-6-hydroxy-1,1'-biphenyl-3-carbonitrile

The desired product was prepared by substituting Example 61A for Example 55B in Example 55C. MS (DCI/NH$_3$) m/z 249 (M+H+NH$_3$)$^+$; $^1$H NMR (CDCl$_3$) δ 7.57 (m, 2H), 7.32 (m, 2H), 7.20 (m, 1H), 7.03 (d, 1H), 5.68 (s, 1H).

EXAMPLE 61C 6-(2-(4-cyanophenyl)-2-oxoethoxy)-3',4'-difluoro-1,1'-biphenyl-3-carbonitrile The desired product was prepared by substituting Example 61B for Example 55C in Example 55D. MS (DCI/NH$_3$) m/z 392 (M+H+NH$_3$)$^+$; $^1$H NMR (CDCl$_3$) δ 8.00 (m, 2H), 7.80 (m, 2H), 7.60 (m, 2H), 7.39 (m, 1H), 7.22 (m, 2H), 6.87 (d, 1H), 5.40 (s, 2H).

EXAMPLE 61D 6-(2-(4-cyanophenyl)-2-hydroxy-2-(1-methyl-1H-imidazol-5-yl)ethoxy)-3',4'-difluoro-1,1'-biphenyl-3-carbonitrile The desired product was prepared by substituting Example 61C for Example 55D in Example 55E. MS (ESI) m/z 457 (M+H)$^+$; $^1$H NMR (DMSO-d$_6$) δ 9.07 (s, 1H), 8.00 (d, 1H), 7.88 (dd, 1H), 7.78 (d, 1H), 7.73 (d, 2H), 7.45 (m, 5H), 7.18 (m, 2H), 4.78 (d, 1H), 4.64 (d, 1H), 3.40 (s, 3H-under water peak); Anal. Calcd. for C$_{26}$H$_{19}$ClF$_2$N$_4$O$_2$.0.50H$_2$O: C, 62.22; H, 4.02; N, 11.16. Found: C, 62.20; H, 3.78; N, 11.10.

EXAMPLE 62

6-(2-(4-cyanophenyl)-2-fluoro-2-(1-methyl-1H-imidazol-5-yl)ethoxy)-3',4'-difluoro-1,1'-biphenyl-3-carbonitrile The desired product was prepared by substituting Example 61D for Example 55E in Example 56. MS (ESI) m/z 459 (M+H)$^+$; $^1$H NMR (DMSO-d$_6$) δ 9.06 (s, 1H), 8.07 (d, 1H), 7.92 (dd, 1H), 7.88 (d, 2H), 7.80 (d, 1H), 7.53 (d, 1H), 7.47 (d, 2H), 7.41 (ddd, 1H), 7.27 (ddd, 1H), 7.10 (m, 1H), 5.09 (s, 1H), 5.02 (s, 1H), 3.43 (s, 3H); Anal. Calcd. for C$_{26}$H$_{18}$ClF$_3$N$_4$O.0.90H$_2$O: C, 61.10; H, 3.90; N, 10.96. Found: C, 61.14; H, 4.06; N, 10.86.

EXAMPLE 63

6-(2-(4-cyanophenyl)-2-hydroxy-2-(1-methyl-1H-imidazol-5-yl)ethoxy)-4'-(trifluoromethoxy)-1,1'-biphenyl-3-carbonitrile

EXAMPLE 63A 6-(ethoxymethoxy)-4'-(trifluoromethoxy)-1,1'-biphenyl-3-carbonitrile The desired product was prepared by substituting 4-(trifluoromethoxy)phenylboronic acid for 3,4-(methylenedioxy)phenylboronic acid in Example 55B. MS (DCI/NH$_3$) m/z 355 (M+H+NH$_3$)$^+$; $^1$H NMR (CDCl$_3$) δ 7.62 (dd, 1H), 7.58 (d, 1H), 7.48 (m, 2H), 7.32 (d,1H), 7.28 (m 2H), 5.26 (s, 2H), 3.65 (q, 2H), 1.20 (t, 3H).

EXAMPLE 63B 6-hydroxy-4'-(trifluoromethoxy)-1,1'-biphenyl-3-carbonitrile

The desired product was prepared by substituting Example 63A for Example 55B in Example 55C. MS (DCI/NH$_3$) m/z 297 (M+H+NH$_3$)$^+$; $^1$H NMR (CDCl$_3$) δ 7.57 (m, 2H), 7.50 (m, 2H), 7.36 (m, 2H), 7.03 (d, 1H), 5.73 (s, 1H).

EXAMPLE 63C 6-(2-(4-cyanophenyl)-2-oxoethoxy)-4'-(trifluoromethoxy)-1,1'-biphenyl-3-carbonitrile The desired product was prepared by substituting Example 63B for Example 55C in Example 55D. MS (DCI/NH$_3$) m/z 440 (M+H+NH$_3$)$^+$; $^1$H NMR (CDCl$_3$) δ 7.98 (m, 2H), 7.78 (m, 2H), 7.60 (m, 2H), 7.54 (m, 2H), 7.27 (m, 2H), 6.89 (d, 1H), 5.36 (s, 2H).

EXAMPLE 63D 6-(2-(4-cyanophenyl)-2-hydroxy-2-(1-methyl-1H-imidazol-5-yl)ethoxy)-4'-(trifluoromethoxy)-1,1'-biphenyl-3-carbonitrile The desired product was prepared by substituting Example 63C for Example 55D in Example 55E. MS (ESI) m/z 505 (M+H)$^+$; $^1$H NMR (DMSO-d$_6$) δ 9.03 (s, 1H), 7.98 (s, 1H), 7.88 (dd, 1H), 7.78 (d, 1H), 7.69 (d, 2H), 7.43 (m, 4H), 7.34 (m, 3H), 7.10 (s, 1H), 4.76 (d, 1H), 4.60 (d, 1H), 3.40 (s, 3H-under water peak); Anal. Calcd. for C$_{27}$H$_{20}$ClF$_3$N$_4$O$_3$.0.50H$_2$O: C, 58.97; H, 3.85; N, 10.19. Found: C, 59.09; H, 3.97; N, 10.26.

EXAMPLE 64

6-(2-(4-cyanophenyl)-2-fluoro-2-(1-methyl-1H-imidazol-5-yl)ethoxy)-4'-(trifluoromethoxy)-1,1'-biphenyl-3-carbonitrile The desired product was prepared by substituting Example 63D for Example 55E in Example 56. MS (ESI) m/z 507 (M+H)$^+$; $^1$H NMR (DMSO-d$_6$) δ 9.14 (s, 1H), 8.13 (d, 1H), 7.92 (dd, 1H), 7.84 (d, 2H), 7.79 (d, 1H), 7.53 (d, 1H), 7.45 (d, 2H), 7.33 (m, 4H), 5.09 (s, 1H), 5.02 (s, 1H), 3.41 (s, 3H); Anal. Calcd. for C$_{27}$H$_{19}$ClF$_4$N$_4$O$_2$.1.15H$_2$O: C, 57.54; H, 3.81; N, 9.94. Found: C, 57.52; H, 3.78; N, 9.90.

EXAMPLE 65

3'-chloro-6-(2-(4-cyanophenyl)-2-hydroxy-2-(1-methyl-1H-imidazol-5-yl)ethoxy)-4'-fluoro-1,1'-biphenyl-3-carbonitrile

EXAMPLE 65A

3'-chloro-6-(ethoxymethoxy)-4'-fluoro-1,1'-biphenyl-3-carbonitrile

The desired product was prepared by substituting 3-chloro-4-fluorophenylboronic acid for 3,4-(methylenedioxy)phenylboronic acid in Example 55B. MS (DCI/NH$_3$) m/z 323, 325 (M+H+NH$_3$)$^+$; $^1$H NMR (CDCl$_3$) δ 7.62 (dd, 1H), 7.56 (d, 1H), 7.51 (dd, 1H), 7.30 (m, 2H), 7.20 (dd, 1H), 5.27 (s, 2H), 3.67 (q, 2H), 1.20 (t, 3H).

EXAMPLE 65B

3',4'-difluoro-6-hydroxy-1,1'-biphenyl-3-carbonitrile

The desired product was prepared by substituting Example 65A for Example 55B in Example 55C. MS (DCI/NH$_3$) m/z 265, 267 (M+H+NH$_3$)$^+$; $^1$H NMR (CDCl$_3$) δ 7.55 (m, 3H), 7.33 (m, 1H), 7.30 (d, 1H), 7.02 (d, 1H), 5.59 (s, 1H).

EXAMPLE 65C

3'-chloro-6-(2-(4-cyanophenyl)-2-oxoethoxy)-4'-fluoro-1,1'-biphenyl-3-carbonitrile The desired product was prepared by substituting Example 65B for Example 55C in Example 55D. Purification by trituration with ethyl acetate provided the desired product. MS (DCI/NH$_3$) m/z 408, 410 (M+H+NH$_3$)$^+$; $^1$H NMR (DMSO-d$_6$) δ 8.15 (d, 2H), 8.07 (d, 2H), 7.89 (m, 2H), 7.84 (dd, 1H), 7.65 (m, 1H), 7.50 (dd, 1H), 7.36 (m, 1H), 5.85 (s, 2H).

EXAMPLE 65D

3'-chloro-6-(2-(4-cyanophenyl)-2-hydroxy-2-(1-methyl-1H-imidazol-5-yl)ethoxy)-4'-fluoro-1,1'-biphenyl-3-carbonitrile The desired product was prepared by substituting Example 65C for Example 55D in Example 55E. MS (ESI) m/z 473, 475 (M+H)$^+$; $^1$H NMR (DMSO-d$_6$) δ 9.05 (s, 1H), 8.00 (s,1H), 7.88 (dd, 1H), 7.80 (d, 1H), 7.72 (d, 2H), 7.64 (dd, 1H),7.42 (m, 4H), 7.32 (1H), 7.11 (s, 1H), 4.73 (d, 1H), 4.60 (d, 1H), 3.40 (s, 3H-under water peak); Anal. Calcd. for C$_{26}$H$_{19}$Cl$_2$FN$_4$O$_2$.0.65H$_2$O: C, 59.93; H, 3.93; N, 10.75. Found: C, 59.89; H, 3.97; N, 10.85.

EXAMPLE 66

3'-chloro-6-(2-(4-cyanophenyl)-2-fluoro-2-(1-methyl-1H-imidazol-5-yl)ethoxy)-4'-fluoro-1,1'-biphenyl-3-carbonitrile The desired product was prepared by substituting Example 65D for Example 55E in Example 56. MS (ESI) m/z 475, 477 (M+H)$^+$; $^1$H NMR (DMSO-d$_6$) δ 9.07 (s, 1H), 8.09 (d, 1H), 7.91 (dd, 1H), 7.87 (d, 2H), 7.82 (d, 1H), 7.51 (m, 2H), 7.45 (m, 2H), 7.40 (d, 1H), 7.28 (ddd, 1H), 5.07 (s, 1H), 5.00 (d, 1H), 3.42 (s, 3H); Anal. Calcd. for C$_{26}$H$_{18}$Cl$_2$F$_2$N$_4$O.1.30H$_2$O: C, 58.40; H, 3.88; N, 10.48. Found: C, 58.44; H, 3.95; N, 10.41.

EXAMPLE 67

6-(2-(4-cyanophenyl)-2-hydroxy-2-(1-methyl-1H-imidazol-5-yl)ethoxy)-3',5'-difluoro-1,1'-biphenyl-3-carbonitrile

EXAMPLE 67A 6-(ethoxymethoxy)-3',5'-difluoro-1,1'-biphenyl-3-carbonitrile

The desired product was prepared by substituting 3,5-difluorophenylboronic acid for 3,4-(methylenedioxy)phenylboronic acid in Example 55B. MS (DCI/NH$_3$) m/z 307 (M+H+NH$_3$)$^+$; $^1$H NMR (CDCl$_3$) δ 7.63 (dd, 1H), 7.58 (d, 1H), 7.33 (d, 1H), 7.00 (m, 2H), 6.83 (m, 1H), 5.28 (s, 2H), 3.68 (q, 2H), 1.20 (t, 3H).

EXAMPLE 67B

3',5'-difluoro-6-hydroxy-1,1'-biphenyl-3-carbonitrile

The desired product was prepared by substituting Example 67A for Example 55B in Example 55C. MS (DCI/NH$_3$) m/z 249 (M+H+NH$_3$)$^+$.

EXAMPLE 67C 6-(2-(4-cyanophenyl)-2-oxoethoxy)-3',5'-difluoro-1,1'-biphenyl-3-carbonitrile The desired product was prepared by substituting Example 67B for Example 55C in Example 55D. Purification by trituration with ethyl acetate provided the desired product. MS (DCI/NH$_3$) m/z 392 (M+H+NH$_3$)$^+$; $^1$H NMR (DMSO-d$_6$) δ 8.16 (d, 2H), 8.07 (d, 2H), 7.93 (d, 1H), 7.84 (dd, 1H), 7.43 (m, 3H), 7.27 (m, 1H), 5.87 (s, 2H).

EXAMPLE 67D 6-(2-(4-cyanophenyl)-2-hydroxy-2-(1-methyl-1H-imidazol-5-yl)ethoxy)-3',5'-difluoro-1,1'-biphenyl-3-carbonitrile The desired product was prepared by substituting Example 67C for Example 55D in Example 55E. MS (ESI)

m/z 457 (M+H)$^+$; $^1$H NMR (DMSO-d$_6$) δ 9.07 (s, 1H), 8.03 (d, 1H), 7.90 (dd, 1H), 7.81 (d, 1H), 7.70 (d, 2H), 7.50 (d, 1H), 7.42 (d, 2H), 7.25 (m, 1H), 7.17 (s, 1H), 7.08 (m, 2H), 4.78 (d, 1H), 4.64 (d, 1H), 3.40 (s, 3H-under water peak); Anal. Calcd. for C$_{26}$H$_{19}$ClF$_2$N$_4$O$_2$.1.00H$_2$O: C, 61.12; H, 4.14; N, 10.97. Found: C, 60.92; H, 3.85; N, 11.01.

EXAMPLE 68

6-(2-(4-cyanophenyl)-2-fluoro-2-(1-methyl-1H-imidazol-5-yl)ethoxy)-3',5'-difluoro-1,1'-biphenyl-3-carbonitrile The desired product was prepared by substituting Example 67D for Example 55E in Example 56. MS (ESI) m/z 459 (M+H)$^+$; $^1$H NMR (DMSO-d$_6$) δ 9.06 (s, 1H), 8.10 (d, 1H), 7.94 (dd, 1H), 7.85 (m, 3H), 7.53 (d, 1H), 7.46 (d, 2H), 7.24 (m, 1H), 6.95 (m, 2H), 5.10 (s, 1H), 5.02 (s, 1H), 3.43 (s, 3H); Anal. Calcd. for C$_{26}$H$_{18}$ClF$_3$N$_4$O.0.50H$_2$O: C, 61.97; H, 3.80; N, 11.12. Found: C, 61.91; H, 3.93; N, 10.79.

EXAMPLE 69

6-(2-(4-cyanophenyl)-2-hydroxy-2-(1-methyl-1H-imidazol-5-yl)ethoxy)-3'-(trifluoromethoxy)-1,1'-biphenyl-3-carbonitrile

EXAMPLE 69A 6-(ethoxymethoxy)-3'-(trifluoromethoxy)-1,1'-biphenyl-3-carbonitrile The desired product was prepared by substituting 3-(trifluoromethoxy)phenylboronic acid for 3,4-(methylenedioxy)phenylboronic acid in Example 55B. MS (DCI/NH$_3$) m/z 355 (M+H+NH$_3$)$^+$; $^1$H NMR (CDCl$_3$) δ 7.62 (dd, 1H), 7.60 (d, 1H), 7.45 (d, 1H), 7.37 (m, 2H), 7.32 (d, 1H), 7.24 (m, 1H), 5.26 (s, 2H), 3.67 (q, 2H), 1.20 (t, 3H).

EXAMPLE 69B 6-hydroxy-3'-(trifluoromethoxy)-1,1'-biphenyl-3-carbonitrile

The desired product was prepared by substituting Example 69A for Example 55B in Example 55C. MS (DCI/NH$_3$) m/z 297 (M+H+NH$_3$)$^+$; $^1$H NMR (CDCl$_3$) δ 7.58 (m, 3H), 7.40 (m, 1H), 7.35 (m, 2H), 7.06 (d, 1H), 5.89 (s, 1H).

EXAMPLE 69C 6-(2-(4-cyanophenyl)-2-oxoethoxy)-3'-(trifluoromethoxy)-1,1'-biphenyl-3-carbonitrile The desired product was prepared by substituting Example 69B for Example 55C in Example 55D. MS (DCI/NH$_3$) m/z 440 (M+H+NH$_3$)$^+$; $^1$H NMR (CDCl$_3$) δ 7.98 (m, 2H), 7.75 (m, 2H), 7.61 (m, 2H), 7.45 (m, 2H), 7.39 (m, 1H), 7.26 (m, 1H), 6.90 (d, 1H), 5.33 (s, 2H).

EXAMPLE 69D 6-(2-(4-cyanophenyl)-2-hydroxy-2-(1-methyl-1H-imidazol-5-yl)ethoxy)-3'-(trifluoromethoxy)-1,1'-biphenyl-3-carbonitrile The desired product was prepared by substituting Example 69C for Example 55D in Example 55E. MS (ESI) m/z 505 (M+H)$^+$; $^1$H NMR (DMSO-d$_6$) δ 9.08 (s, 1H), 8.02 (s, 1H), 7.90 (dd, 1H), 7.80 (d, 1H), 7.64 (d, 2H), 7.50 (m, 2H), 7.40 (m, 5H), 7.13 (s, 1H), 4.76 (d, 1H), 4.60 (d, 1H), 3.40 (s, 3H-under water peak); Anal. Calcd. for C$_{27}$H$_{20}$ClF$_3$N$_4$O$_3$.0.40H$_2$O: C, 59.16; H, 3.82; N, 10.22. Found: C, 59.18; H, 3.73; N, 10.31.

EXAMPLE 70

6-(2-(4-cyanophenyl)-2-fluoro-2-(1-methyl-1H-imidazol-5-yl)ethoxy)-3'-(trifluoromethoxy)-1,1'-biphenyl-3-carbonitrile The desired product was prepared by substituting Example 69D for Example 55E in Example 56. MS (ESI) m/z 507 (M+H)$^+$; $^1$H NMR (DMSO-d$_6$) δ 9.08 (s, 1H), 8.09 (d, 1H), 7.92 (dd, 1H), 7.81 (m, 3H), 7.50 (m, 2H), 7.40 (m, 3H), 7.30 (d, 1H), 7.25 (s, 1H), 5.06 (s, 1H), 5.00 (m, 1H), 3.41 (s, 3H); Anal. Calcd. for C$_{27}$H$_{19}$ClF$_4$N$_4$O$_2$.0.60H$_2$O: C, 58.57; H, 3.68; N, 10.12. Found: C, 58.59; H, 3.96; N, 9.97.

EXAMPLE 71

3',4'-dichloro-6-(2-(4-cyanophenyl)-2-hydroxy-2-(1-methyl-1H-imidazol-5-yl)ethoxy)-1,1'-biphenyl-3-carbonitrile

EXAMPLE 71A

3',4'-dichloro-6-(ethoxymethoxy)-1,1'-biphenyl-3-carbonitrile

The desired product was prepared by substituting 3,4-dichlorophenylboronic acid for 3,4-(methylenedioxy)phenylboronic acid in Example 55B. MS (DCI/NH$_3$) m/z 339, 341 (M+H+NH$_3$)$^+$; $^1$H NMR (CDCl$_3$) δ 7.62 (dd, 1H), 7.56 (m, 2H), 7.50 (d, 1H), 7.30 (m, 2H), 5.27 (s, 2H), 3.68 (q, 2H), 1.20 (t, 3H).

EXAMPLE 71B

3',4'-dichloro-6-hydroxy-1,1'-biphenyl-3-carbonitrile

The desired product was prepared by substituting Example 71A for Example 55B in Example 55C. MS (DCI/NH$_3$) m/z 281, 283 (M+H+NH$_3$)$^+$.

EXAMPLE 71C

3',4'-dichloro-6-(2-(4-cyanophenyl)-2-oxoethoxy)-1,1'-biphenyl-3-carbonitrile

The desired product was prepared by substituting Example 71B for Example 55C in Example 55D. MS (DCI/NH$_3$) m/z 424, 426 (M+H+NH$_3$)$^+$; $^1$H NMR (DMSO-d$_6$) δ 8.15 (m, 2H), 8.05 (m, 2H), 7.92 (d, 1H), 7.88 (d, 1H), 7.82 (dd, 1H), 7.67 (d, 1H), 7.63 (dd, 1H), 7.38 (d, 1H), 5.83 (s, 2H).

EXAMPLE 71D

3',4'-dichloro-6-(2-(4-cyanophenyl)-2-hydroxy-2-(1-methyl-1H-imidazol-5-yl)ethoxy)-1,1'-biphenyl-3-carbonitrile The desired product was prepared by substituting Example 71C for Example 55D in Example 55E. MS (ESI) m/z 489, 491 (M+H)$^+$; $^1$H NMR (DMSO-d$_6$) δ 9.07 (s, 1H), 8.01 (s, 1H), 7.90 (dd, 1H), 7.81 (d, 1H), 7.68 (m, 3H), 7.63 (d, 1H), 7.46 (d, 1H), 7.40 (d, 2H), 7.30 (dd, 1H), 7.15 (s, 1H), 4.74 (d, 1H), 4.62 (d, 1H), 3.40 (s, 3H-under water peak); Anal. Calcd. for C$_{26}$H$_{19}$Cl$_3$N$_4$O$_2$.0.80H$_2$O: C, 57.81; H, 3.84; N, 10.37. Found: C, 57.82; H, 3.64; N, 10.02.

EXAMPLE 72

3',4'-dichloro-6-(2-(4-cyanophenyl)-2-fluoro-2-(1-methyl-1H-imidazol-5-yl)ethoxy)-1,1'-biphenyl-3-carbonitrile The desired product was prepared by substituting Example 71D for Example 55E in Example 56. MS (ESI) m/z 491, 493 (M+H)$^+$; $^1$H NMR (DMSO-d$_6$) δ 9.09 (s, 1H), 8.10 (d, 1H), 7.92 (dd, 1H), 7.83 (m, 3H), 7.60 (d, 1H), 7.56 (d, 1H), 7.52 (d, 1H), 7.45 (d, 2H), 7.24 (dd, 1H), 5.07 (m, 1H), 5.00 (m, 1H), 3.43 (s, 3H); Anal. Calcd. for C$_{26}$H$_{18}$Cl$_2$FN$_4$O.1.45H$_2$O: C, 56.38; H, 3.80; N, 10.11. Found: C, 56.43; H, 3.78; N, 9.76.

EXAMPLE 73

3',5'-dichloro-6-(2-(4-cyanophenyl)-2-hydroxy-2-(1-methyl-1H-imidazol-5-yl)ethoxy)-1,1'-biphenyl-3-carbonitrile

EXAMPLE 73A

3',5'-dichloro-6-(ethoxymethoxy)-1,1'-biphenyl-3-carbonitrile

The desired product was prepared by substituting 3,5-dichlorophenylboronic acid for 3,4-(methylenedioxy)phenylboronic acid in Example 55B. MS (DCI/NH$_3$) m/z 339, 341(M+H+NH$_3$)$^+$; $^1$H NMR (CDCl$_3$) δ 7.63 (dd, 1H), 7.57 (d, 1H), 7.38 (m, 1H), 7.32 (m, 3H), 5.28 (s, 2H), 3.68 (q, 2H), 1.20 (t, 3H).

EXAMPLE 73B

3',5'-dichloro-6-hydroxy-1,1'-biphenyl-3-carbonitrile

The desired product was prepared by substituting Example 73A for Example 55B in Example 55C. MS (DCI/NH$_3$) m/z 281, 283 (M+H+NH$_3$)$^+$.

EXAMPLE 73C

3',5'-dichloro-6-(2-(4-cyanophenyl)-2-oxoethoxy)-1,1'-biphenyl-3-carbonitrile

The desired product was prepared by substituting Example 73B for Example 55C in Example 55D. Purification by trituration with chloroform provided the desired product. MS (DCI/NH$_3$) m/z 424, 426(M+H+NH$_3$)$^+$; $^1$H NMR (DMSO-d$_6$) δ 8.16 (d, 2H), 8.05 (d, 2H), 7.93 (d, 1H), 7.84 (dd, 1H), 7.70 (d, 2H), 7.60 (dd, 1H), 7.39 (d, 1H), 5.85 (s, 2H).

EXAMPLE 73D

3',5'-dichloro-6-(2-(4-cyanophenyl)-2-hydroxy-2-(1-methyl-1H-imidazol-5-yl)ethoxy)-1,1'-biphenyl-3-carbonitrile The desired product was prepared by substituting Example 73C for Example 55D in Example 55E. MS (ESI) m/z 489, 491 (M+H)$^+$; $^1$H NMR (DMSO-d$_6$) δ 9.07 (s, 1H), 8.05 (s, 1H), 7.90 (dd, 1H), 7.84 (d, 1H), 7.68 (d, 2H), 7.64 (dd, 1H), 7.47 (m, 3H), 7.38 (d, 2H), 7.16 (s, 1H), 4.73 (d, 1H), 4.59 (d, 1H), 3.40 (s, 3H-under water peak); Anal. Calcd. for C$_{26}$H$_{19}$Cl$_3$N$_4$O$_2$.0.80H$_2$O: C, 57.81; H, 3.84; N, 10.37. Found: C, 57.81; H, 3.85; N, 10.18.

EXAMPLE 74

3',5'-dichloro-6-(2-(4-cyanophenyl)-2-fluoro-2-(1-methyl-1H-imidazol-5-yl)ethoxy)-1,1'-biphenyl-3-carbonitrile The desired product was prepared by substituting Example 73D for Example 55E in Example 56. MS (ESI) m/z 491, 493 (M+H)$^+$; $^1$H NMR (DMSO-d$_6$) δ 9.12 (s, 1H), 8.14 (m, 1H), 7.94 (d, 1H), 7.86 (d, 2H), 7.83 (s, 1H), 7.60 (d, 1H), 7.51 (d, 1H), 7.44 (d, 2H), 7.37 (s, 2H), 5.07 (m, 1H), 5.00 (m, 1H), 3.43 (s, 3H); Anal. Calcd. for C$_{26}$H$_{18}$Cl$_2$FN$_4$O.0.85H$_2$O: C, 57.50; H, 3.66; N, 10.32. Found: C, 57.55; H, 3.84; N, 10.01.

EXAMPLE 75

6-(2-(4-cyanophenyl)-2-hydroxy-2-(1-methyl-1H-imidazol-5-yl)ethoxy)-3'-fluoro-1,1'-biphenyl-3-carbonitrile

EXAMPLE 75A 6-(ethoxymethoxy)-3'-fluoro-1,1'-biphenyl-3-carbonitrile

The desired product was prepared by substituting 3-fluorophenylboronic acid for 3,4-(methylenedioxy)phenylboronic acid in Example 55B. MS (DCI/NH$_3$) m/z 289 (M+H+NH$_3$)$^+$; $^1$H NMR (CDCl$_3$) δ 7.60 (m, 2H), (m, 1H), 7.33 (m, 1H), 7.20 (m, 2H), 7.08 (m, 1H), 5.26 (s, 2H), 3.68 (q, 2H), 1.20 (t, 3H).

EXAMPLE 75B

3'-fluoro-6-hydroxy-1,1'-biphenyl-3-carbonitrile

The desired product was prepared by substituting Example 75A for Example 55B in Example 55C. MS (DCI/NH$_3$) m/z 231 (M+H+NH$_3$)$^+$; $^1$H NMR (DMSO-d$_6$) δ 10.92 (br s, 1H), 7.78 (d, 1H), 7.66 (dd, 1H), 7.45 (m, 3H), 7.19 (m, 1H), 7.10 (d, 1H).

EXAMPLE 75C 6-(2-(4-cyanophenyl)-2-oxoethoxy)-3'-fluoro-1,1'-biphenyl-3-carbonitrile The desired product was prepared by substituting Example 75B for Example 55C in Example 55D. MS (DCI/NH$_3$) m/z 374 (M+H+NH$_3$)$^+$; $^1$H NMR (DMSO-d$_6$) δ 8.15 (d, 2H), 8.07 (d, 2H), 7.85 (d, 1H), 7.81 (dd, 1H), 7.50 (m, 3H), 7.35 (d, 1H), 7.22 (m, 1H), 5.86 (s, 2H).

EXAMPLE 75D 6-(2-(4-cyanophenyl)-2-hydroxy-2-(1-methyl-1H-imidazol-5-yl)ethoxy)-3'-fluoro-1,1'-biphenyl-3-carbonitrile The desired product was prepared by substituting Example 75C for Example 55D in Example 55E. MS (ESI) m/z 439 (M+H)$^+$; $^1$H NMR (DMSO-d$_6$) δ 9.07 (s, 1H), 8.00 (d, 1H), 7.88 (dd, 1H), 7.78 (d, 1H), 7.70 (d, 2H), 7.47 (d, 1H), 7.40 (m, 3H), 7.17 (m, 4H), 4.77 (d, 1H), 4.60 (d, 1H), 3.40 (s, 3H-under water peak); Anal. Calcd. for C$_{26}$H$_{20}$ClFN$_4$O$_2$.1.00H$_2$O: C, 63.35; H, 4.50; N, 11.37. Found: C, 63.39; H, 4.36; N, 11.35.

EXAMPLE 76

6-(2-(4-cyanophenyl)-2-fluoro-2-(1-methyl-1H-imidazol-5-yl)ethoxy)-3'-fluoro-1,1'-biphenyl-3-carbonitrile The desired product was prepared by substituting Example 75D for Example 55E in Example 56. MS (ESI) m/z 441 (M+H)$^+$; $^1$H NMR (DMSO-d$_6$) δ 9.10 (s, 1H), 8.11 (m, 1H), 7.92 (dd, 1H), 7.85 (d, 2H), 7.78 (d, 1H), 7.53 (d, 1H), 7.45 (d, 2H), 7.38 (m, 1H), 7.20 (m, 1H), 7.08 (m, 1H), 7.02 (m, 1H), 5.09 (d, 1H), 5.02 (s, 1H), 3.43 (s, 3H); Anal. Calcd. for $C_{26}H_{19}ClF_2N_4O\cdot 0.90H_2O$: C, 63.33; H, 4.25; N, 11.36. Found: C, 63.38; H, 4.42; N, 11.19.

EXAMPLE 77

3'-chloro-6-(2-(4-cyanophenyl)-2-hydroxy-2-(1-methyl-1H-imidazol-5-yl)ethoxy)-1,1'-biphenyl-3-carbonitrile

EXAMPLE 77A

3'-chloro-6-(ethoxymethoxy)-1,1'-biphenyl-3-carbonitrile

The desired product was prepared by substituting 3-chlorophenylboronic acid for 3,4-(methylenedioxy)phenylboronic acid in Example 55B. MS (DCI/NH$_3$) m/z 305, 307 (M+H+NH$_3$)$^+$; $^1$H NMR (CDCl$_3$) δ 7.61 (dd, 1H), 7.59 (d, 1H), 7.46 (m, 1H), 7.34 (m, 4H), 5.26 (s, 2H), 3.68 (q, 2H), 1.20 (t, 3H).

EXAMPLE 77B

3'-chloro-6-hydroxy-1,1'-biphenyl-3-carbonitrile

The desired product was prepared by substituting Example 77A for Example 55B in Example 55C. MS (DCI/NH$_3$) m/z 247, 249 (M+H+NH$_3$)$^+$; $^1$H NMR (DMSO-d$_6$) δ 10.92 (br s, 1H), 7.78 (d, 1H), 7.66 (dd, 1H), 7.64 (m, 1H), 7.45 (m 3H), 7.10 (d, 1H).

EXAMPLE 77C

3'-chloro-6-(2-(4-cyanophenyl)-2-oxoethoxy)-1,1'-biphenyl-3-carbonitrile

The desired product was prepared by substituting Example 77B for Example 55C in Example 55D. MS (DCI/NH$_3$) m/z 390, 392 (M+H+NH$_3$)$^+$; $^1$H NMR (DMSO-d$_6$) δ 8.15 (d, 2H), 8.07 (d, 2H), 7.86 (d, 1H), 7.81 (dd, 1H), 7.70 (m, 1H), 7.60 (m, 1H), (7.47 (m, 2H), 7.34 (d, 1H), 5.86 (s, 2H).

EXAMPLE 77D

3'-chloro-6-(2-(4-cyanophenyl)-2-hydroxy-2-(1-methyl-1H-imidazol-5-yl)ethoxy)-1,1'-biphenyl-3-carbonitrile The desired product was prepared by substituting Example 77C for Example 55D in Example 55E. MS (ESI) m/z 455, 457 (M+H)$^+$; $^1$H NMR (DMSO-d$_6$) δ 9.11 (s, 1H), 8.05 (d, 1H), 7.88 (dd, 1H), 7.77 (d, 1H), 7.67 (d, 2H), 7.45 (m, 4H), 7.36 (d, 2H), 7.25 (m, 1H), 7.20 (s, 1H), 4.75 (d, 1H), 4.58 (d, 1H), 3.40 (s, 3H-under water peak); Anal. Calcd. for $C_{26}H_{20}Cl_2N_4O_2\cdot 1.20H_2O$: C, 60.88; H, 4.40; N, 10.92. Found: C, 60.87; H, 4.28; N, 10.71.

EXAMPLE 78

3'-chloro-6-(2-(4-cyanophenyl)-2-fluoro-2-(1-methyl-1H-imidazol-5-yl)ethoxy)-1,1'-biphenyl-3-carbonitrile The desired product was prepared by substituting Example 77D for Example 55E in Example 56. MS (ESI) m/z 457, 459 (M+H)$^+$; $^1$H NMR (DMSO-d$_6$) δ 9.12 (s, 1H), 8.13 (m, 1H), 7.92 (dd, 1H), 7.84 (d, 2H), 7.80 (d, 1H), 7.51 (d, 1H), 7.45 (m, 3H), 7.40 (d, 1H), 7.36 (m, 1H), 7.20 (m, 1H), 5.07 (s, 1H), 5.00 (d, 1H), 3.43 (s, 3H); Anal. Calcd. for $C_{26}H_{19}Cl_2FN_4O\cdot 0.85H_2O$: C, 61.39; H, 4.10; N, 11.01. Found: C, 61.44; H, 3.94; N, 10.81.

EXAMPLE 79

4-(2-(4-cyanophenyl)-2-hydroxy-2-(1-methyl-1H-imidazol-5-yl)ethoxy)-3-(2,2-difluoro-1,3-benzodioxol-5-yl)benzonitrile

EXAMPLE 79A 2,2-difluoro-1,3-benzodioxol-5-ylboronic acid

A solution of 1.5M tert-butyllithium in pentane (130 mL, 195 mmol) in diethyl ether (500 mL) at −78° C. was treated with 5-bromo-2,2-difluoro-1,3-benzodioxole (18 g, 76 mmol) in diethyl ether (80 mL), stirred for 1 hour, treated with triisopropylborate (37 mL, 160 mmol), warmed to room temperature over 1 hour, poured into 4M NaOH (700 mL), stirred for 15 minutes, cooled, adjusted to pH 1 with concentrated HCl, and extracted with ethyl acetate. The extract was washed with brine, dried (Na$_2$SO$_4$), filtered, and concentrated to provide 14.7 g (95%) of the desired product. $^1$H NMR (DMSO-d$_6$) δ 7.75 (m, 1H), 7.66 (m, 1H), 7.51 (m, 1H), 7.39 (m, 1H), 7.30 (m, 1H).

EXAMPLE 79B 3-(2,2-difluoro-1,3-benzodioxol-5-yl)-4-(ethoxymethoxy)benzonitrile The desired product was prepared by substituting Example 79A for 3,4-(methylenedioxy)phenylboronic acid in Example 55B. MS (DCI/NH$_3$) m/z 351 (M+H+NH$_3$)$^+$; $^1$H NMR (CDCl$_3$) δ 7.61 (dd, 1H), 7.55 (d, 1H), 7.33 (d, 1H), 7.20 (s, 1H), 7.12 (s, 2H), 5.28 (s, 2H), 3.68 (q, 2H), 1.20 (t, 3H).

EXAMPLE 79C 3-(2,2-difluoro-1,3-benzodioxol-5-yl)-4-hydroxybenzonitrile

The desired product was prepared by substituting Example 79B for Example 55B in Example 55C. MS (DCI/NH$_3$) m/z 293 (M+H+NH$_3$)$^+$; $^1$H NMR (CDCl$_3$) δ 7.57 (dd, 1H), 7.53 (d, 1H), 7.19 (m, 3H), 7.04 (d, 1H), 5.55 (s, 1H).

EXAMPLE 79D 4-(2-(4-cyanophenyl)-2-oxoethoxy)-3-(2,2-difluoro-1,3-benzodioxol-5-yl)benzonitrile The desired product was prepared by substituting Example 79C for Example 55C in Example 55D. MS (DCI/NH$_3$) m/z 436 (M+H+NH$_3$)$^+$; $^1$H NMR (CDCl$_3$) δ 8.00 (m, 2H), 7.79 (m, 2H), 7.60 (m, 2H), 7.30 (d, 1H), 7.19 (dd, 1H), 7.13 (d, 1H), 6.88 (d, 1H), 5.40 (s, 2H).

EXAMPLE 79E 4-(2-(4-cyanophenyl)-2-hydroxy-2-(1-methyl-1H-imidazol-5-yl)ethoxy)-3-(2,2-difluoro-1,3-benzodioxol-5-yl)benzonitrile The desired product was prepared by substituting Example 79D for Example 55D in Example 55E. MS (ESI) m/z 501 (M+H)$^+$; $^1$H NMR (DMSO-d$_6$) δ 9.09 (s, 1H), 8.02 (d, 1H), 7.88 (dd, 1H), 7.75 (d, 1H), 7.70 (d, 2H), 7.50 (d, 1H), 7.43 (m, 3H), 7.25 (d, 1H), 7.15 (m, 2H), 4.80 (d, 1H), 4.66 (d, 1H), 3.40 (s, 3H-under water peak); Anal. Calcd. for C$_{27}$H$_{19}$F$_{2}$ClN$_{4}$O$_{4}$.1.60H$_{2}$O: C, 57.32; H, 3.96; N, 9.90. Found: C, 57.51; H, 4.38; N, 10.04.

EXAMPLE 80

4-(2-(4-cyanophenyl)-2-fluoro-2-(1-methyl-1H-imidazol-5-yl)ethoxy)-3-(2,2-difluoro-1,3-benzodioxol-5-yl)benzonitrile The desired product was prepared by substituting Example 79E for Example 55E in Example 56. MS (ESI) m/z 503 (M+H)$^+$; $^1$H NMR (DMSO-d$_6$) δ 9.03 (s, 1H), 8.05 (d, 1H), 7.91 (dd, 1H), 7.84 (d, 2H), 7.78 (d, 1H), 7.52 (d, 1H), 7.47 (d, 2H), 7.39 (d, 1H), 6.90 (m, 2H), 5.10 (s, 1H), 5.03 (s, 1H), 3.42 (s, 3H); Anal. Calcd. for C$_{27}$H$_{18}$F$_3$ClN$_4$O$_3$.0.65H$_2$O: C, 58.90; H, 3.53; N, 10.35. Found: C, 58.93; H, 3.60; N, 9.81.

EXAMPLE 81

4-(2-(4-cyanophenyl)-2-hydroxy-2-(1-methyl-1H-imidazol-5-yl)ethoxy)-3-(1-naphthyl)benzonitrile

EXAMPLE 81A 4-(ethoxymethoxy)-3-(1-naphthyl)benzonitrile

The desired product was prepared by substituting 1-naphthaleneboronic acid for 3,4-(methylenedioxy)phenylboronic acid in Example 55B. MS (DCI/NH$_3$) m/z 321 (M+H+NH$_3$)$^+$; $^1$H NMR (CDCl$_3$) δ 7.90 (d, 2H), 7.71 (dd, 1H), 7.60 (d, 1H), 7.50 (m, 3H), 7.38 (m, 3H), 5.10 (m, 2H), 3.48 (m, 2H), 1.10 (t, 3H).

EXAMPLE 81B 4-hydroxy-3-(1-naphthyl)benzonitrile

The desired product was prepared by substituting Example 81A for Example 55B in Example 55C. MS (DCI/NH$_3$) m/z 263 (M+H+NH$_3$)$^+$; $^1$H NMR (CDCl$_3$) δ 7.98 (m, 2H), 7.67 (dd, 1H), 7.58 (m, 2H), 7.53 (m, 3H), 7.46 (dd, 1H), 7.13 (d, 1H), 5.33 (s, 1H).

EXAMPLE 81C 4-(2-(4-cyanophenyl)-2-oxoethoxy)-3-(1-naphthyl)benzonitrile

The desired product was prepared by substituting Example 81B for Example 55C in Example 55D. MS (DCI/NH$_3$) m/z 406 (M+H+NH$_3$)$^+$; $^1$H NMR (CDCl$_3$) δ 7.90 (d, 2H), 7.72 (dd, 1H), 7.65 (m, 3H), 7.50 (m, 2H), 7.40 (m, 4H), 7.34 (m, 1H), 7.00 (d, 1H), 5.11 (s, 2H).

EXAMPLE 81D 4-(2-(4-cyanophenyl)-2-hydroxy-2-(1-methyl-1H-imidazol-5-yl)ethoxy)-3-(1-naphthyl)benzonitrile The desired product was prepared by substituting Example 81C for Example 55D in Example 55E. MS (ESI) m/z 471 (M+H)$^+$; $^1$H NMR (DMSO-d$_6$) δ 8.91, 8.89 (both s, total 1H), 8.00 (m, 3H), 7.70 (dd, 1H), 7.65 (m, 1H), 7.60 (m, 1H), 7.50 (m, 1H), 7.42 (m, 1H), 7.35 (m, 1H), 7.30 (m, 1H), 7.20, 7.14 (both d, total 2H), 7.04 (d, 1H), 6.93 (d, 1H), 6.60 (m, 2H), 4.68, 4.57 (both d, total 1H), 4.30, 4.25 (both d, total 1H), 3.12, 3.10 (both s, total 3H); Anal. Calcd. for C$_{30}$H$_{23}$ClN$_4$O$_2$.0.80H$_2$O: C, 69.17; H, 4.95; N, 10.54. Found: C, 69.17; H, 4.95; N, 10.54.

EXAMPLE 82

6-(2-(4-cyanophenyl)-2-hydroxy-2-(1,3-thiazol-5-yl)ethoxy)-4'-(trifluoromethoxy)-1,1'-biphenyl-3-carbonitrile The desired product was prepared by substituting 1-(trimethylsilyl)thiazole for 1-methyl-2-(triethylsilyl)-1H-imidazole in Example 63D. The free base was purified by flash column chromatography using 3:7 hexanes/ethyl acetate to provide the desired product. MS (ESI) m/z 508 (M+H)$^+$; $^1$H NMR (DMSO-d$_6$) δ 9.01 (s, 1H), 7.91 (s, 1H), 7.85 (dd, 1H), 7.77 (d, 1H), 7.74 (m, 2H), 7.63 (m, 2H), 7.46 (d, 1H), 7.33 (m, 2H), 7.19 (d, 2H), 4.88 (d, 1H), 4.74 (d, 1H); Anal. Calcd. for C$_{26}$H$_{17}$ClF$_3$N$_3$O$_3$S: C, 57.41; H, 3.15; N, 7.72. Found: C, 57.09; H, 3.24; N, 7.71.

EXAMPLE 83

6-(2-amino-2-(4-cyanophenyl)-2-(1-methyl-1H-imidazol-5-yl)ethoxy)-4'-(trifluoromethoxy)-1,1'-biphenyl-3-carbonitrile A mixture of Example 64 (0.9 g, 1.64 mmol) in NH$_4$OH (15 mL) and 1,4-dioxane (6 mL) at –70° C. in a tube was treated with ammonia gas to form liquid ammonia (1 mL). The tube was sealed, heated at 90° C. overnight, cooled to –70° C., carefully opened and warmed to room temperature. The mixture was extracted with ethyl acetate (1×150 mL) and the organic layer was washed with brine, dried (MgSO$_4$), filtered and concentrated. The concentrate was purified by flash column chromatography on silica gel with a solvent gradient of 0–3% methanol in dichloromethane to provide 234 mg (28%) of the desired product. MS (ESI) m/z 504 (M+H)$^+$; $^1$H NMR (CD$_3$OD), δ 7.73 (dd, 1H), 7.62 (d, 1H), 7.56–7.52 (m, 3H), 7.38–7.25 (m, 7H), 7.10 (d, 1H), 4.56 (dd, 2H), 3.24 (s, 3H).

EXAMPLE 84

6-((2-(4-cyanophenyl)-2-hydroxy-2-(1-methyl-1H-imidazol-5-yl)ethyl)(methyl)amino)-3'-methoxy-1,1'-biphenyl-3-carbonitrile

EXAMPLE 84A 4-(2-(1-methyl-1H-imidazol-5-yl)oxiran-2-yl)benzonitrile

A slurry of 95% NaH (1.0 g, 39.6 mmol) in DMSO (23 mL) was heated to 75° C. for 45 minutes. The heating bath was removed, THF (28 mL) was added, and the solution was cooled to –7° C. The mixture was treated with a –10° C. solution of trimethylsulfonium methyl sulfate (7.2 g, 38.3 mmol) in DMSO (15 mL) and THF (10 mL) was added, followed by a slurry of Example 37F (5.7 g, 27.0 mmol) in DMSO (15 mL) and THF (15 mL). After 10 minutes the cooling bath was removed, the reaction was stirred at room temperature for 70 minutes, and partitioned between water and ethyl acetate. The organic layer was washed with brine, dried (Na$_2$SO$_4$), filtered, and concentrated. The concentrate was purified by flash column chromatography on silica gel with 97.5:2.5 dichloromethane/ethanol to provide 3.9 g (64%) of the desired product. MS (DCI/NH$_3$) m/z 226 (M+H)$^+$; $^1$H NMR (DMSO-d$_6$) δ 7.77 (m, 2H), 7.68 (s, 1H), 7.32 (m, 2H), 7.13 (d, 1H), 3.60 (d, 1H), 3.20 (d, 1H).

EXAMPLE 84B 3-chloro-4-(methylamino)benzonitrile

A mixture of 3-chloro-4-fluorobenzonitrile (5.2 g, 33 mmol), THF (55 mL), and 40% methylamine in water (25 mL, 290 mmol) in a sealed tube was heated to 65° C. for 1.5 hours, cooled to room temperature. The organic phase was washed with brine, dried (Na$_2$SO$_4$), filtered, and concentrated. The resulting solid was dried for about 16 hours under high vacuum in the presence of P$_2$O$_5$ to provide 6.3 g (95%) of the desired product. MS (DCI/NH$_3$) m/z 184, 186 (M+H+NH$_3$)$^+$; $^1$H NMR (DMSO-d$_6$) δ 7.72 (d, 1H), 7.55 (dd, 1H), 6.70 (d, 1H), 6.52 (br q, 1H), 2.80 (d, 3H).

EXAMPLE 84C

3'-methoxy-6-(methylamino)-1,1'-biphenyl-3-carbonitrile

The desired product was prepared by substituting Example 84B for 3-chloro-4-methylbenzonitrile in Example 31A and heating the reaction to 55° C. for 16 hours. Purification by flash chromatography on silica gel with 4:1 hexanes/ethyl acetate provided the desired product. MS (DCI/NH$_3$) m/z 256 (M+H+NH$_3$)$^+$; $^1$H NMR (DMSO-d$_6$) δ 7.57 (dd, 1H), 7.39 (dd, 1H), 7.30 (d, 1H), 6.96 (m, 1H), 6.92 (m, 1H), 6.90 (m, 1H), 6.67 (d, 1H), 5.74 (br q, 1H), 3.80 (s, 3H), 2.73 (d, 3H).

EXAMPLE 84D 6-((2-(4-cyanophenyl)-2-hydroxy-2-(1-methyl-1H-imidazol-5-yl)ethyl)(methyl)amino)-3'-methoxy-1,1'-biphenyl-3-carbonitrile A solution of Example 84C (3.5 g, 14.9 mmol) in DMF (35 mL) was treated with 95% NaH (0.42 g, 16.7 mmol), stirred at room temperature for 1.5 hours, treated with a solution of Example 84A (2.8 g, 12.6 mmol) in DMF (10 mL), and stirred at room temperature for 2 hours. The reaction was poured into water and filtered. The solid was dried for 16 hours under high vacuum in the presence of P$_2$O$_5$, then purified by flash column chromatography on silica gel with 97:3:0.5 then 93:7:1 ethyl acetate/ethanol/conc. NH$_4$OH to provide 2.1 g (36%) of the free base. The hydrochloride salt was prepared as described in Example 55E. MS (APCI) m/z 464 (M+H)$^+$; $^1$H NMR (DMSO-d$_6$) δ 9.01 (s, 1H), 7.76 (d, 2H), 7.54 (d, 1H), 7.46 (m, 3H), 7.34 (d, 1H), 7.25 (dd, 1H), 7.10 (d, 1H), 6.93 (dd, 1H), 6.83 (m, 2H), 6.58 (d, 1H), 4.05 (m, 1H), 3.81 (s, 3H), 3.79 (m, 1H), 3.35 (s, 3H), 2.58 (s, 3H); Anal. Calcd. for C$_{28}$H$_{26}$ClN$_5$O$_2$.1.85H$_2$O: C, 63.06; H, 5.61; N, 13.13. Found: C, 62.99; H, 5.47; N, 13.45.

EXAMPLE 85

6-((2-(4-cyanophenyl)-2-fluoro-2-(1-methyl-1H-imidazol-5-yl)ethyl)(methyl)amino)-3'-methoxy-1,1'-biphenyl-3-carbonitrile The desired product was prepared by substituting Example 84D for Example 55E in Example 56. MS (ESI) m/z 466 (M+H)$^+$; $^1$H NMR (DMSO-d$_6$) δ 8.91 (s, 1H), 7.89 (d, 2H), 7.63 (d, 1H), 7.58 (dd, 1H), 7.45 (d, 2H), 7.41 (d, 1H), 7.22 (m, 2H), 6.92 (dd, 1H), 6.73 (m, 1H), 6.54 (d, 1H), 4.20 (m, 1H), 4.10 (m, 1H), 3.78 (s, 3H), 3.40 (s, 3H), 2.60 (d, 3H); Anal. Calcd. for C$_{28}$H$_{25}$ClFN$_5$O.1.00H$_2$O: C, 64.67; H, 5.23; N, 13.47. Found: C, 64.64; H, 5.00; N, 13.30.

EXAMPLE 86

6-((2-(4-cyanophenyl)-2-hydroxy-2-(1-methyl-1H-imidazol-5-yl)ethyl)(methyl)amino)-4'-(trifluoromethoxy)-1,1'-biphenyl-3-carbonitrile

EXAMPLE 86A 6-(methylamino)-4'-(trifluoromethoxy)-1,1'-biphenyl-3-carbonitrile The desired product was prepared by substituting Example 84B for 3-chloro-4-methylbenzonitrile and 4-(trifluoromethoxy)phenylboronic acid for 3-methoxyphenylboronic acid in Example 31A and heating the reaction to 55° C. for 16 hours. Purification by flash column chromatography on silica gel with 4:1 hexanes/ethyl acetate provided the desired product. MS (DCI/NH$_3$) m/z 310 (M+H+NH$_3$)$^+$; $^1$H NMR (DMSO-d$_6$) δ 7.54 (dd, 1H), 7.39 (m, 2H), 7.32 (m, 2H), 7.29 (d, 1H), 6.64 (d, 1H), 4.39 (br s, 1H), 2.86 (s, 3H).

EXAMPLE 86B 6-((2-(4-cyanophenyl)-2-hydroxy-2-(1-methyl-1H-imidazol-5-yl)ethyl)(methyl)amino)-4'-(trifluoromethoxy)-1,1'-biphenyl-3-carbonitrile The desired product was prepared by substituting Example 86A for Example 84C in Example 84D. MS (ESI) m/z 518 (M+H)$^+$; $^1$H NMR (DMSO-d$_6$) δ 9.02 (s, 1H), 7.82 (d, 2H), 7.70 (d, 1H), 7.55 (dd, 1H), 7.53 (d, 2H), 7.40 (d, 1H), 7.33 (d, 2H), 7.27 (d, 1H), 7.20 (d, 2H), 6.89 (s, 1H), 4.08 (d, 1H), 3.90 (d, 1H), 3.35 (s, 3H), 2.44 (s, 3H); Anal. Calcd. for C$_{28}$H$_{23}$ClF$_3$N$_5$O$_2$.0.90H$_2$O: C, 58.98; H, 4.38; N, 12.28. Found: C, 58.99; H, 4.36; N, 12.40.

EXAMPLE 87

5-cyano-2-(((4-cyanophenyl)(1-methyl-1H-imidazol-5-yl)methoxy)methyl)-N-(4-methylpyridin-2-yl)benzamide

EXAMPLE 87A

Methyl 5-cyano-2-methylbenzoate

A solution of 3-chloro-4-methylbenzonitrile (25.0 g, 0.165 mol) in methanol (250 mL) in a steel reaction vessel was treated with lithium carbonate (13.4 g, 0.182 mol) and PdCl$_2$.dppf (6.75 g). The vessel was purged with nitrogen, sealed, and heated to 140° C. at 400 psi for 17 hours, filtered and concentrated. The concentrate was treated with ethyl acetate, washed with saturated NaHCO$_3$, dried (MgSO$_4$), filtered, and concentrated. The concentrate was purified by flash chromatography on silica gel with 95:5 to 85:15 hexanes/ethyl acetate to provide 14.4 g (50%) of the desired product. MS (DCI/NH$_3$) m/z 193.0 (M+NH$_4$)$^+$; $^1$H NMR (CDCl$_3$) δ 8.22 (d, 1H), 7.67 (dd, 1H), 7.37 (d, 1H), 3.93 (s, 3H), 2.68 (s, 3H).

EXAMPLE 87B

Methyl 2-(bromomethyl)-5-cyanobenzoate

The desired product was prepared by substituting Example 87A for Example 31A in Example 31B. $^1$H NMR (CDCl$_3$) δ 8.27 (d, 1H), 7.77 (dd, 1H), 7.61 (d, 1H), 4.96 (s, 2H), 3.99 (s, 3H).

EXAMPLE 87C

Methyl 5-cyano-2-(((4-cyanophenyl)(1-methyl-1H-imidazol-5-yl)methoxy)methyl)benzoate A mixture of Example 87B (0.100 g, 0.394 mmol) and Example 1B (0.101 g, 0.472 mmol) in dichloromethane (3 mL) was warmed with a heat gun until a clear solution resulted, treated with silver (I) oxide (0.365 g, 1.58 mmol), wrapped in aluminum foil, and stirred at room temperature for two days. The solid was filtered through diatomaceous earth (Celite®), concentrated, and purified by flash column chromatography on silica gel with 10:0.2:0.02 to 10:1:0.1 ethyl acetate/methanol/NH$_4$OH to provide 78.5 mg (52%) of the desired product as a pink form. MS (DCI/NH$_3$) m/z 387.1 (M+H)$^+$; $^1$H NMR (CDCl$_3$) δ 8.28 (s, 1H), 7.89 (d, 1H), 7.83 (d, 1H), 7.69 (d, 2H), 7.54 (d, 2H), 7.48 (s, 1H), 6.89 (s, 1H), 5.72 (s, 1H), 5.01 (q, 2H), 3.89 (s, 3H), 3.45 (s, 3H).

EXAMPLE 87D 5-cyano-2-(((4-cyanophenyl)(1-methyl-1H-imidazol-5-yl)methoxy)methyl)-N-(4-methylpyridin-2-yl)benzamide A solution of 2-amino-4-picoline (112 mg, 1.04 mmol) in 1,2-dichloroethane (1.5 mL) at 0° C. was treated with 1M (CH$_3$)$_2$AlCl in hexanes (1.0 mL, 1.04 mmol), stirred at room temperature for 15 minutes, treated with a solution of Example 87C (40.0 mg, 0.104 mmol) in 1,2-dichloroethane (1.5 mL), heated to 75° C. for about 18 hours, cooled, diluted with dichloromethane and water, and stirred for 30 minutes. The organic phase was filtered through diatomaceous earth (Celite®), washed with saturated NaHCO$_3$ and brine, dried (MgSO$_4$), filtered, and concentrated. The concentrate was purified using flash column chromatography on silica gel with 10:0.2:0.02 to 10:1:0.1 ethyl acetate/methanol/NH$_4$OH to provide 38 mg (79%) of the desired product. MS (HR-FAB): calculated: 463.1882 (M+H)$^+$; observed: 463.1883 (M+H)$^+$; $^1$H NMR (CDCl$_3$) δ 8.53 (br s, 1H), 8.12 (d, 1H), 8.01 (s, 1H), 7.94 (d, 1H), 7.79 (dd, 1H), 7.63 (d, 1H), 7.54–7.45 (m, 4H), 7.41 (s, 1H), 6.97–6.94 (m, 2H), 5.69 (s, 1H), 4.84 (q, 2H), 3.35 (s, 3H), 2.39 (s, 3H).

EXAMPLE 88

N-(3-chlorophenyl)-5-cyano-2-(((4-cyanophenyl)(1-methyl-1H-imidazol-5-yl)methoxy)methyl)benzamide

EXAMPLE 88A 5-cyano-2-(((4-cyanophenyl)(1-methyl-1H-imidazol-5-yl)methoxy)methyl)benzoic acid A solution of Example 87C (0.426 g, 1.10 mmol) in THF/methanol (12 mL/4 mL) at 0° C. was treated with a solution of LiOH.H$_2$O (0.139 g, 3.30 mmol) in water (1 mL), warmed to room temperature, stirred for about 18 hours, and concentrated. The concentrate was dissolved in water and ethyl acetate and the aqueous layer was adjusted to pH 5 with 1N HCl and extracted twice with dichloromethane. The combined organic phases were dried (MgSO$_4$), filtered, and concentrated to provide the hydrochloride salt. The concentrate (0.349 g, 78%) was used directly without further purification. $^1$H NMR (CDCl$_3$) δ 9.11 (br s, 1H), 7.87 (d, 1H), 7.81–7.79 (m, 2H), 7.70 (d, 2H), 7.54 (d, 2H), 7.35 (s, 1H), 5.77 (s, 1H), 5.07 (q, 2H), 3.37 (s, 3H).

EXAMPLE 88B

N-(3-chlorophenyl)-5-cyano-2-(((4-cyanophenyl)(1-methyl-1H-imidazol-5-yl)methoxy)methyl)benzamide A solution of Example 88A (25.0 mg, 0.0611 mmol) in DMF (1.5 mL) was treated with 3-chloroaniline (9.7 μL, 0.0917 mmol), EDC (17.6 mg, 0.0917 mmol), HOBT (12.4 mg, 0.0917), and diisopropylethylamine (31.9 μL, 0.183 mmol), stirred at room temperature for about 24 hours, and diluted with ethyl acetate and saturated NH$_4$Cl. After separation, the organic phase was washed with saturated NaHCO$_3$ and brine, dried (MgSO$_4$), filtered, and concentrated. The residue was purified using flash chromatography eluted with ethyl acetate/methanol/NH$_4$OH (10:0.2:0.02 to 10:1:0.1) to provide 14.0 mg (48%) of the desired product as an off-white solid. MS (ESI) m/z 482.0 (M+H)$^+$; $^1$H NMR (CDCl$_3$) δ 8.70 (s, 1H), 7.81 (s, 1H), 7.66 (d, 1H), 7.57 (s, 1H), 7.54 (d, 1H), 7.50 (d, 2H), 7.36 (d, 2H), 7.29–7.26 (m, 1H), 7.21–7.18 (m, 2H), 7.09–7.08 (m, 1H), 6.69 (s, 1H), 5.55 (s, 1H), 4.76 (q, 2H), 3.28 (s, 3H).

EXAMPLE 89

5-(((4-cyanophenyl)(1-methyl-1H-imidazol-5-yl)methoxy)methyl)-6-(2,2-difluoro-1,3-benzodioxol-5-yl)pyridine-2-carbonitrile

EXAMPLE 89A 2-bromo-3-methylpyridine 1-oxide

A solution of 2-bromo-3-methylpyridine (10.0 mL, 0.0898 mol) in dichloromethane (150 mL) at 0° C. was treated with mCPBA (~77%, 22.1 g, 0.0987 mol) in three equivalent portions. The mixture was warmed to room temperature, stirred for 18 hours, cooled to 0° C., and treated with 1N NaOH (50 mL). The organic phase was washed with 1N NaOH and saturated NaHCO$_3$, dried (MgSO$_4$), filtered, and concentrated. The concentrate was purified by flash column chromatography on silica gel with ethyl acetate and 9:1 ethyl acetate/methanol to provide 7.83 g (47%) of the desired product. MS (DCI/NH$_3$) m/z 187.9 (M+H)$^+$; $^1$H NMR (CDCl$_3$) δ 8.28–8.26 (m, 1H), 7.15–7.09 (m, 2H), 2.46 (s, 3H).

EXAMPLE 89B 6-bromo-5-methylpyridine-2-carbonitrile

A solution of Example 89A (36.4 g, 0.194 mol) in 1,2-dichloroethane (480 mL) was treated with trimethylsilyl cyanide (31.4 mL, 0.252 mol) and dimethylcarbamyl chloride (23.4 mL, 0.252 mol). The reaction mixture was heated to 80° C. for 5 hours, cooled to room temperature, and stirred for about 18 hours. The mixture was treated with 10% NaHCO$_3$ solution, stirred for 10 minutes, and extracted twice with dichloromethane. The combined extracts were dried (MgSO$_4$), filtered, and concentrated. The concentrate was recrystallized from ethyl acetate three times to provide 17.7 g of the desired product mixed with the biscyano byproduct in a 2.7:1 ratio. The mixture was used directly without purification.

EXAMPLE 89C 6-bromo-5-(bromomethyl)pyridine-2-carbonitrile

The desired product was prepared as a mixture with the biscyano byproduct described in Example 89B by substituting Example 89B for Example 31A in Example 31B. The mixture was used directly without purification.

EXAMPLE 89D 6-bromo-5-(((4-cyanophenyl)(1-methyl-1H-imidazol-5-yl)methoxy)methyl)pyridine-2-carbonitrile The desired product was prepared as a mixture with the biscyano byproduct described in Example 89B by substituting Example 89C for Example 87B in Example 87C. The mixture was used directly without purification.

EXAMPLE 89E

2,2-difluoro-1,3-benzodioxol-5-ylboronic acid

A solution of 5-bromo-2,2-difluorobenzodioxole (1.18 g, 4.97 mmol) in anhydrous diethyl ether (8 mL) at −78° C. was treated with 2.5M n-BuLi in hexane (2.4 mL, 5.97 mmol), stirred for 1 hour, and treated with triisopropyl borate (1.5 mL, 6.46 mmol). The mixture was slowly warmed to room temperature and stirred for about 18 hours. The reaction was quenched with saturated $NH_4Cl/10\%$ HCl and extracted with ethyl acetate. The combined extracts were dried ($MgSO_4$), filtered, and concentrated. The concentrate was used directly without further purification. $^1H$ NMR ($CD_3OD$) δ 7.26–7.11 (m, 3H).

EXAMPLE 89F

5-(((4-cyanophenyl)(1-methyl-1H-imidazol-5-yl) methoxy)methyl)-6-(2,2-difluoro-1,3-benzodioxol-5-yl)pyridine-2-carbonitrile A solution of Example 89D (45.0 mg) in toluene (1.8 mL) and ethanol (1.8 mL) was treated with Example 89E (44.4 mg, 2 equivalents), $Na_2CO_3$ (25.6 mg, 2.2 eq.), and $Pd(PPh_3)_4$ (6.4 mg, 0.05 eq.). The mixture was heated to 50° C. in a capped vial for about 18 hours and concentrated. The concentrate was partitioned between ethyl acetate and saturated $NaHCO_3$. The organic phase was dried ($MgSO_4$), filtered, and concentrated. The concentrate was purified by preparative HPLC to provide 23 mg of the desired product as the bis-trifluoroacetate salt(Dynamx C18 (5 µm, 21.4×250 mm) column was used containing a Rainin Dynamax solvent delivery system with a Dynamax UV-D II detector. The solvent system used was a 20% to 100% acetonitrile/water containing 0.1% TFA linear gradient. The elution rate was 10 mL/min and the UV detection wavelength was set at 254 nm). MS (HR-FAB) m/z calculated: 486.1378 $(M+H)^+$; observed: 486.1395 $(M+H)^+$; $^1H$ NMR ($CD_3OD$) δ 8.87 (s, 1H), 8.24 (d, 1H), 7.91 (d, 1H), 7.78 (d, 2H), 7.55 (d, 2H), 7.39 (s, 1H), 7.29 (s, 2H), 7.23 (s, 1H), 5.91 (s, 1H), 4.71 (q, 2H), 3.74 (s, 3H).

EXAMPLE 90

5-(((4-cyanophenyl)(1-methyl-1H-imidazol-5-yl) methoxy)methyl)-6-(3,5-difluorophenyl)pyridine-2-carbonitrile The desired product was prepared as the bis-trifluoroacetate salt by substituting 3,5-difluorophenylboronic acid for Example 89E in Example 89F. MS (HR-FAB) m/z calculated: 442.1479 $(M+H)^+$; observed: 442.1471 $(M+H)^+$; $^1H$ NMR ($CD_3OD$) δ 8.90 (s, 1H), 8.24 (d, 1H), 7.94 (d, 1H), 7.79 (d, 2H), 7.57 (d, 2H), 7.27 (s, 1H), 7.14–7.08 (m, 3H), 5.95 (s, 1H), 4.71 (q, 2H), 3.74 (s, 3H); Anal. cald. C, 52.03; H, 2.86; N, 10.46; observed: C, 52.82; H, 2.98; N, 10.60.

EXAMPLE 91

4-(((4-cyanophenyl)(1-methyl-1H-imidazol-5-yl) methoxy)methyl)-3-(6-oxo-1-propyl-1,6-dihydropyridin-3-yl)benzonitrile

EXAMPLE 91A

3-iodo-4-methylbenzonitrile

The desired product was prepared by substituting 4-amino-2-chlorobenzonitrile with 2-amino-3-methylbenzonitrile following the procedure in Example 54A. MS ($DCI/NH_3$) m/z 261 $(M+NH_4)^+$; $^1H$ NMR ($CDCl_3$) δ 8.80 (d, 1H), 7.54 (dd, 1H), 7.32 (d, Hz), 2.50 (s, 3H).

EXAMPLE 91B

4-(bromomethyl)-3-iodobenzonitrile

The desired product was prepared by substituting Example 91A for Example 31A in Example 31B. MS ($DCI/NH_3$) m/z 338.8 $(M+NH_4)^+$; $^1H$ NMR ($CDCl_3$) δ 8.143 (d, 1H), 7.63 (dd, 1H), 7.56 (d, 1H), 4.57 (s, 2H).

EXAMPLE 91C

4-(((4-cyanophenyl)(1-methyl-1H-imidazol-5-yl) methoxy)methyl)-3-iodobenzonitrile The desired product was prepared by substituting Example 91B for Example 87B in Example 87C. MS ($DCI/NH_3$) m/z 455.0 $(M+H)^+$; $^1H$ NMR ($CDCl_3$) δ 8.11 (d, 1H), 7.71–7.67 (m, 3H), 7.56 (t, 3H), 7.48 (s, 1H), 6.99 (s, 1H), 5.70 (s, 1H), 6.55 (q, 2H), 3.41 (s, 3H).

EXAMPLE 91D

6-fluoropyridin-3-ylboronic acid

The desired product was prepared by substituting 5-bromo-2-fluoropyridine for 5-bromo-2,2-difluorobenzodioxole in Example 89E. The crude product was used directly without further purification.

EXAMPLE 91E

4-(((4-cyanophenyl)(1-methyl-1H-imidazol-5-yl) methoxy)methyl)-3-(6-fluoropyridin-3-yl) benzonitrile A solution of Example 91C (0.385 g, 0.848 mmol) in toluene (7.5 mL) and ethanol (7.5 mL) was treated with Example 91D (0.239 g, 1.70 mmol), $Na_2CO_3$ (0.198 g, 1.87 mmol), and $Pd(PPh_3)_4$ (49.0 mg). The reaction mixture was heated to 80° C. in a pressure vessel for about 18 hours. The mixture was concentrated and the concentrate was partitioned between ethyl acetate and saturated $NaHCO_3$. The organic phase was dried ($MgSO_4$), filtered, and concentrated. The concentrate was purified by flash column chromatography with 10:0.2:0.02 to 10:1:0.1 ethyl acetate/methanol/$NH_4OH$ to provide 0.246 g (69%) of the desired product. MS ($DCI/NH_3$) m/z 424.1 $(M+H)^+$; $^1H$ NMR ($CDCl_3$) δ 8.17 (d, 1H), 7.74 (dd, 1H), 7.69 (dt, 1H), 7.65 (d, 3H), 7.57 (d, 1H), 7.42–7.39 (m, 3H), 7.00 (dd, 1H), 6.89 (s, 1H), 5.52 (s, 1H), 4.45 (q, 2H), 3.30 (s, 3H).

EXAMPLE 91F

4-(((4-cyanophenyl)(1-methyl-1H-imidazol-5-yl) methoxy)methyl)-3-(6-oxo-1,6-dihydropyridin-3-yl) benzonitrile A mixture of Example 91E (0.230 g, 0.543 mmol) in acetic acid (28 mL) and water (7 mL) was heated at 90° C. for 3 days and concentrated. The concentrate was lyophilized to provide 0.251 g (96%) of the desired acetic acid salt. The concentrate was dissolved in dichloromethane and washed with saturated $NaHCO_3$. The organic phase was dried ($MgSO_4$), filtered, and concentrated to provide 0.109 g of the desired product. The crude product was used directly without further purification. MS ($DCI/NH_3$) m/z 422.1

(M+H)+ (data for acetic acid salt); $^1$H NMR (CD$_3$OD) δ (data for free base) 7.78–7.71 (m, 4H), 7.67 (d, 1H), 7.60–7.57 (m, 1H), 7.55 (d, 1H), 7.51 (d, 2H), 7.45 (d, 1H), 6.68 (s, 1H), 6.55 (d, 1H), 5.76 (s, 1H), 4.57 (q, 2H), 3.45 (s, 3H).

EXAMPLE 91G 4-(((4-cyanophenyl)(1-methyl-1H-imidazol-5-yl)methoxy)methyl)-3-(6-oxo-1-propyl-1,6-dihydropyridin-3-yl)benzonitrile A solution of Example 91F (27.3 mg, 0.0648 mmol) in DMF (2 mL) at 0° C. was treated with NaH (60%, 3.1 mg, 0.0777 mmol), stirred for 15 minutes, and treated with n-propyl bromide (11.8 μL, 0. 130 mmol). The mixture was slowly warmed to room temperature and stirred for about 18 hours. The mixture was quenched with saturated NH$_4$Cl and extracted with ethyl acetate. The combined extracts were dried (MgSO$_4$), filtered, and concentrated. The concentrate was purified by flash column chromatography with 10:0.2:0.02 to 10:1:0.1 ethyl acetate/methanol/NH$_4$OH to provide 10.5 mg (35%) of the desired product. MS.(HR-FAB) m/z calculated: 464.2087 (M+H)+; observed: 464.2078 (M+H)+; $^1$H NMR (CDCl$_3$) δ 7.67 (d, 1H), 7.59 (d, 1H), 7.53 (d, 1H), 7.47–7.44 (m, 3H), 7.26–7.24 (m, 3H), 6.96 (s, 1H), 6.60–6.58 (m, 1H), 5.58 (s, 1H), 4.50 (q, 2H), 3.86 (t, 2H), 3.33 (s, 3H), 1.80–1.74 (m, 2H), 0.94 (t, 3H).

EXAMPLE 92

4-(((4-cyanophenyl)(1-methyl-1H-imidazol-5-yl)methoxy)methyl)-3-(6-propoxypyridin-3-yl)benzonitrile The desired product (6.5 mg, 22%) was isolated from the mixture formed in Example 91G.

$^1$H NMR (CDCl$_3$), δ 8.04 (d, 1H), 7.70–7.63 (m, 4H), 7.55 (d, 1H), 7.46–7.38 (m, 4H), 6.64 (s, 1H), 6.77 (d, 1H), 5.51 (s, 1H), 4.49 (q, 2H), 4.29 (t, 2H), 3.34 (s, 3H), 1.90–1.78 (m, 2H), 1.06 (t, 3H).

EXAMPLE 93

6-(2-(4-cyanophenyl)-2-hydroxy-2-(1-methyl-1H-imidazol-5-yl)ethoxy)-4'-(trifluoromethoxy)-1,1'-biphenyl-3-carbonitrile

EXAMPLE 93A (1R,2S,5R)-2-isopropyl-5-methylcyclohexyl (4-cyanophenyl)(oxo)acetate A mixture of ethyl (4-cyanophenyl)(oxo)acetate (35.2 g, 173 mmol), (1R,2S,5R)-(−)-menthol (41.0 g, 262 mmol), and titanium ethoxide (3.6 mL, 17 mmol) was heated to 80° C. under vacuum for 60 hours. The mixture was diluted with MTBE (1.5 L), washed sequentially with 10% HCl (2×300 mL), saturated aqueous NaHCO$_3$, and brine, dried (MgSO$_4$), filtered, and concentrated. The concentrate was purified by flash column chromatography on silica gel with 2% ethyl acetate/hexanes to provide the desired product (50.0 g, 92% yield). $^1$H NMR (CDCl$_3$) δ 8.12 (m, 2H), 7.82 (m, 2H), 5.01 (ddd, 2H), 2.15 (m, 1H), 1.91 (m, 1H), 1.72 (m, 2H), 1.55 (m, 2H), 1.16 (m, 2H), 0.97(d, 3H), 0.91 (d, 3H), 0.83 (d, 3H).

EXAMPLE 93B (1R,2S,5R)-2-isopropyl-5-methylcyclohexyl (4-cyanophenyl)(hydroxy)(1-methyl-1H-imidazol-5-yl)acetate A mixture of zinc dust (9.4 g, 143.7 mmol) in THF (5 mL) was treated with 1,2-dibromoethane (0.62 mL, 7.2 mmol), heated to 50° C., stirred for 15 minutes, and cooled to 30° C. The mixture was treated with chlorotrimethylsilane (0.91 mL, 7.2 mmol), stirred for 5 minutes, heated to reflux, treated slowly with 5-iodo-1-methyl-1H-imidazole (20.0 g, 96.2 mmol), and continued to reflux for 30 minutes. The reaction was cooled to room temperature and stirring was aborted to allow the excess zinc to settle to the bottom of the flask.

A solution of magnesium bromide diethyl etherate (10.3 g, 39.9 mmol) and Example 93A (50.0 g, 79.8 mmol) in THF (100 mL) was cooled to −10° C. and treated with a solution of the 1-methyl-5-zinciodo-1H-imidazole from above in THF (120 mL) over 15 minutes. The mixture was warmed to room temperature, stirred for 18 hours, quenched with saturated NH$_4$Cl (100 mL), and the layers were separated. The aqueous phase was extracted with ethyl acetate (300 mL) and the combined organic phases were washed with brine. The reaction mixture was filtered through diatomaceous earth (Celite®), treated with toluene (~250 mL), concentrated at a bath temperture of 60° C. The mixture was allowed to sit for 18 hours and then filtered. The filter cake was washed with toluene and dried under vacuum at 50° C. to provide 30.0 g (81% potent, 77% yield, 97.4% de). MS (ACPI) m/e 396 (M+H)+; $^1$H NMR (CD$_3$OD) δ 8.02 (br s, 1H), 7.78 (d, 2H), 7.63 (d, 2H), 7.13 (br s, 1H), 4.76 (ddd, 1H), 3.49 (s, 3H), 2.06 (br d, 1H), 1.72–1.60 (m, 2H), 1.55–1.42 (m, 1H), 1.30 (m, 1H), 1.14 (q, 1H), 1.07–0.98 (m, 2H), 0.95 (d, 3H), 0.94–0.84 (m, 1H), 0.66 (d, 3H), 0.50 (d, 3H).

EXAMPLE 93C 4-(1,2-dihydroxy-1-(1-methyl-1H-imidazol-5-yl)ethyl)benzonitrile A mixture of Example 93B (2.15 g, 78% potency, 4.24 mmol) in THF (6.5 mL) was treated with a solution of 2M LiBH$_4$ in THF (3.3 mL, 6.1 mmol), heated to 55° C. for 3 hours, cooled to room temperature, treated with 20% citric acid (12 mL), warmed to 50° C. for 30 minutes, and extracted with MTBE (2×20 mL). The aqueous phase was adjusted to pH>10 with 50% NaOH and extracted with 5:1 THF/ethyl acetate (2×30 mL). The combined organic phases were concentrated, treated with citric acid (1.0 g), and concentrated to a volume of approximately 6 mL. The solution was adjusted to pH>10 with 50% NaOH, stirred for 2 hours, and filtered. The filter cake was washed with water (2 mL) and dried under vacuum with an air bleed to provide 670 mg (61% potency, 40% potency adjusted yield) of the desired product as one enantiomer in high excess. MS (ACPI) m/e 244 (M+H)+; $^1$H NMR (CD$_3$OD) δ 7.70 (d, 2H) 7.55 (s, 1H) 7.54 (d, 2H) 7.18 (s, 1H) 4.00 (d, 1H) 3.89 (d, 1H) 3.30 (s, 3H).

EXAMPLE 93D 6-fluoro-4'-(trifluoromethoxy)-1,1'-biphenyl-3-carbonitrile

A 100 mL 3-necked flask equipped with a stir bar, a condenser, and a nitrogen inlet was flushed with nitrogen and then charged with 3-bromo-4-fluorobenzonitrile (2.507 g, 1.23×10$^{-2}$ mol), 4-trifluoromethoxyphenyl boronic acid (2.825 g, 1.23×10$^{-2}$ mol, 1.01 equiv), bis(triphenylphosphine)-palladium(II) chloride (2.0 mg, 2.85×10$^{-6}$ mol, 0.02 mol %), and sodium bicarbonate (1.577 g, 1.82×10$^{-2}$ mol, 1.5 equiv). The flask was then evacuated and purged with nitrogen three times, and charged with deoxygenated toluene (6 mL) and deoxygenated water (6 mL). The mixture was heated to 80° C. until HPLC analysis indicated the disappearance of the aryl bromide (less than 16 hours; HPLC conditions: Eclipse XDB-C8 (4.6 mm×150 mm), flow rate: 1.5 mL/min.; mobile phase: 80:20 water(0.1% $H_3PO_4$)/$CH_3CN$ to 20:80 in 8 minutes, hold to 15 minutes with the column at 35° C. and UV detection: 210 nm. Retention time for the product is 8.88 min, retention time for aryl bromide is 6.47 min, retention time for excess boronic acid is 5.64 min, and retention time for homocoupled product is 10.58 minutes). The reaction was cooled to room temperature and the phases were separated. The organic phase was filtered through a plug of silica (2.5 g) and the silica plug was washed with toluene (25 mL). The filtrate was concentrated to provide the desired product (3.472 g, 92% potency, 93% potency adjusted yield). HRMS (FAB) calcd. for $C_{14}H_7F_4NO$ (M+H)$^+$; 282.0542, found 282.0536; $^1H$ NMR (CDCl$_3$) δ 7.76 (dd, 1H), 7.68 (ddd, 1H), 7.56 (m, 2H), 7.34 (m, 2H), 7.30 (dd, 1H); $^{13}C$ (CDCl$_3$) δ 161.9, 149.5, 134.9, 133.5, 131.9, 130.4, 129.5, 121.2 (2), 120.4, 117.8, 117.7, 109.1; IR(KBr) 2230, 1514, 1490, 1265, 1256, 1223, 1210, 1157; Analytical: Pd 6 ppm, B<30 ppm, Na<1 ppm; mp~63.5–64.2° C.

EXAMPLE 93E 6-((2S)-2-(4-cyanophenyl)-2-hydroxy-2-(1-methyl-1H-imidazol-5-yl)ethoxy)-4'-(trifluoromethoxy)-1,1'-biphenyl-3-carbonitrile A mixture of Example 93C (399 mg, 1.6 mmol) and Example 93D (640 mg, 2.3 mmol) in DMF (4 mL) was cooled to 0° C., treated with 1M LiHMDS in THF (1.5 mL), warmed to room temperature, and stirred for 24 hours. The mixture was treated with 30% methanol (15 mL) and the mixture was filtered. The filter cake was mixed with ethyl acetate (5 mL) at 50° C. for 20 minutes, slowly cooled to 0° C., and stirred at 0° C. for 1 hour. The solid was filtered, washed with 1 mL cold ethyl acetate, and dried at 45° C. under vacuum to provide 250 mg (33% yield, >98% ee by HPLC) of the desired product. MS (ESI) m/e 505 (M+H)$^+$; $^1H$ NMR (DMSO-d$_6$) δ 7.82 (dd, 1H), 7.74 (d, 1H), 7.61 (d, 2H), 7.53 (s, 1H), 7.44 (d, 1H), 7.41–7.25 (m, 6H), 7.13 (d, 1H), 6.45 (s, 1H), 4.75 (d, 1H), 4.55 (d, 1H), 3.17 (s, 3H). $(\alpha)_D^{25}$ (free base)=−59.616° (c=10.156 mg/mL,$CH_3OH$).

Alternative Process for Forming Example 93E

EXAMPLE 93F 3-bromo-4-(2-(4-cyanophenyl)-2-hydroxy-2-(1-methyl-1H-imidazol-5-yl)ethoxy)benzonitrile A suspension of Example 93C (1.19 g, 4.9 mmol), 4-fluoro-3-bromobenzonitrile (1.50 g, 7.5 mmol), DMAP (0.12 g, 1 mmol), and potassium carbonate (5.00 g, 36 mmol) in DMSO (13 mL) at room temperature was stirred for 16 hours, quenched with water (20 mL), treated with ethyl acetate (70 mL), and filtered. The filter cake was washed with water and dried at 40° C. under vacuum to provide 1.50 g (72% yield, HPLC purity 95.6%) of the desired product. $^1H$ NMR (400 MHz, DMSO-d$_6$) δ 8.09 (d, 1H), 7.84–7.80 (m, 3H), 7.61–7.58 (m, 3H), 7.37 (d, 1H), 7.16 (d, 1H), 6.56 (br s, 1H), 4.67 (d, 1H), 4.52 (d, 1H), 3.19 (s, 3H).

EXAMPLE 93E 6-((2S)-2-(4-cyanophenyl)-2-hydroxy-2-(1-methyl-1H-imidazol-5-yl)ethoxy)-4'-(trifluoromethoxy)-1,1'-biphenyl-3-carbonitrile A 50 mL 3-necked flask equipped with a stir bar, a condenser, and a nitrogen inlet was flushed with nitrogen and charged with Example 93D (506.6 mg, 1.2 mmol), 4-trifluoromethoxyphenylboronic acid (396.4 mg, 1.73 mmol, 1.4 equiv), bis(triphenylphosphine)-palladium(II) chloride (40.0 mg, 5.77×10$^{-5}$ mol, 4.8 mol %), and potassium fluoride (216.2 mg, 3.72 mmol, 3.1 equiv). The flask was evacuated and purged with nitrogen three times, charged with deoxygenated THF (5 mL) and deoxygenated ethanol (5 mL). Vigorous stirring was continued while the mixture was maintained under a nitrogen atmosphere. The mixture was heated to 80° C. until the HPLC analysis indicated the disappearance of the aryl bromide (less than 4 hours). The assay yield was 89% for the desired product.

It will be evident to one skilled in the art that the present invention is not limited to the forgoing illustrative examples, and that it can be embodied in other specific forms without departing from the essential attributes thereof. It is therefore desired that the examples be considered in all respects as illustrative and not restrictive, reference being made to the appended claims, rather than to the foregoing examples, and all changes which come within the meaning and range of equivalency of the claims and therefore intended to be embraced therein.

What is claimed is:

1. A compound of formula (I)

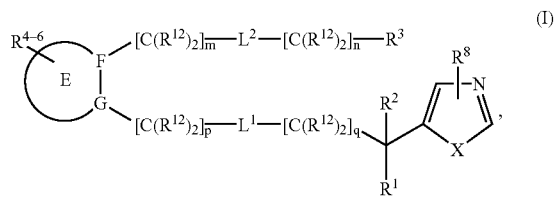

or a therapeutically acceptable salt thereof, wherein

E is a six-membered aromatic carbocyclic ring in which F and G are C;

$L^1$ is O;

$L^2$ is selected from the group consisting of a bond, $C_2$ alkenylene, $C_2$ alkynylene, O, $NR^9$, C(O), S, S(O), $SO_2$, $SO_2NR^9$, $NR^9SO_2$, $C(O)NR^9$, $NR^9C(O)$, and $CO_2$;

X is $NR^7$;

$R^1$ is selected from the group consisting of aryl and arylalkyl;

$R^2$ is selected from the group consisting of hydrogen, alkoxy, alkyl, amino, aminoalkyl, cyano, cyanoalkyl, cycloalkyl, cycloalkylalkyl, halo, haloalkyl, hydroxy, and hydroxyalkyl;

$R^3$ is selected from the group consisting of aryl, heterocycle, and cycloalkyl, wherein the heterocyle may be substituted or unsubstituted and is selected from the group consisting of benzodioxolyl, thiophenyl, quinolinyl, pyridinyl, and dihydropyridinyl;

$R^{4-6}$ are each independently selected from the group consisting of hydrogen, $NR^9C(O)$, $C(O)NR^9$, alkanoyl, alkenyl, alkoxy, alkoxyalkyl, alkyl, alkylsulfonyl, alkynyl, amido, amino, aminoalkyl, aminosulfonyl, aryl, arylalkyl, aryloxy, arylsulfonyl, azido, carboxy, cyano, cyanoalkyl, cycloalkyl, cycloalkylalkyl, halo, haloalkoxy, haloalkyl, hydroxy, hydroxyalkyl, nitro, nitroalkyl, oxo, and thio(oxo);

$R^7$ is selected from the group consisting of hydrogen, alkyl, aryl, cycloalkyl, cycloalkylalkyl, and trialkylsilyl;

R[9] is selected from the group consisting of hydrogen, alkoxyalkyl, alkyl, amidoalkyl, aminoalkyl, aryl, arylalkyl, cycloalkyl, cycloalkylalkyl, carboxyalkyl, hydroxyalkyl; and each R[12] is independently selected from the group consisting of hydrogen, alkoxy, alkyl, amino, halo, and hydroxy;

m is 0, 1, 2, 3 or 4;

n is 0, 1, 2, 3 or 4;

p is 0, 1, 2, 3 or 4; and q is 0, 1, 2, 3 or 4.

2. A compound according to claim 1 of formula (II)

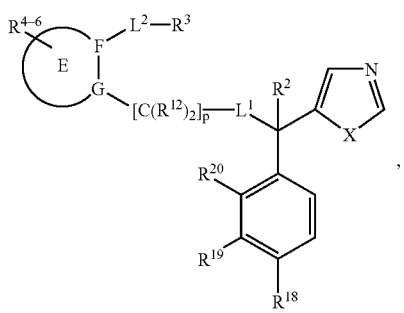

(II)

or a therapeutically acceptable salt thereof, wherein

E, F, G, L[1], L[2], X, R[2], R[3], R[4-6], R[12], and p are as defined in claim 1 and R[18], R[19], and R[20] are each independently selected from the group consisting of hydrogen, cyano, and halo.

3. A compound according to claim 2 wherein

L[2] is selected from the group consisting of a bond, NR[9]SO$_2$, and C(O)NR[9];

wherein each group is drawn with its left end attached to F and its right end attached to R[3];

R[2] is selected from the group consisting of hydrogen and hydroxy;

R[3] is selected from the group consisting of aryl and heterocycle wherein the heterocyle may be substituted or unsubstituted and is selected from the group consisting of benzodioxolyl, thiophenyl, quinolinyl, pyridinyl, and dihydropyridinyl;

R[12] is hydrogen; and p is 0 or 1.

4. A compound according to claim 3 wherein one of R[4-6] is cyano.

5. A compound according to claim 4 wherein

R[18] is cyano; and

R[19] and R[20] are hydrogen.

6. A compound according to claim 5 selected from the group consisting of 6-(((4-cyanophenyl)(1-methyl-1H-imidazol-5-yl)methoxy)methyl)-3'-methoxy(1,1'-biphenyl)-3-carbonitrile;

6-(((4-cyanophenyl)(1-methyl-1H-imidazol-5-yl)methoxy)methyl)-3'-ethoxy(1,1'-biphenyl)-3-carbonitrile;

3-(1,3-benzodioxol-5-yl)-4-(((4-cyanophenyl)(1-methyl-1H-imidazol-5-yl)methoxy)methyl)benzonitrile;

3'-chloro-6-(((4-cyanophenyl)(1-methyl-1H-imidazol-5-yl)methoxy)methyl)(1,1'-biphenyl)-3-carbonitrile;

N-(5-cyano-2-(((4-cyanophenyl)(1-methyl-1H-imidazol-5-yl)methoxy)methyl)phenyl)-2-thiophenesulfonamide;

N-(5-cyano-2-(((4-cyanophenyl)(1-methyl-1H-imidazol-5-yl)methoxy)methyl)phenyl)-4-methylbenzenesulfonamide;

5-cyano-2-(((4-cyanophenyl)(1-methyl-1H-imidazol-5-yl)methoxy)methyl)-N-(4-methylpyridin-2-yl)benzamide;

N-(3-chlorophenyl)-5-cyano-2-(((4-cyanophenyl)(1-methyl-1H-imidazol-5-yl)methoxy)methyl)benzamide;

4-(((4-cyanophenyl)(1-methyl-1H-imidazol-5-yl)methoxy)methyl)-3-(6-oxo-1-propyl-1,6-dihydropyridin-3-yl)benzonitrile; and 4-(((4-cyanophenyl)(1-methyl-1H-imidazol-5-yl)methoxy)methyl)-3-(6-propoxypyridin-3-yl)benzonitrile.

7. A compound according to claim 3 wherein one of R[4-6] is halo.

8. A compound according to claim 7 wherein R[3] is heterocycle wherein the heterocyle may be substituted or unsubstituted and is selected from the group consisting of benzodioxolyl, thiophenyl, quinolinyl, pyridinyl, and dihydropyridinyl.

9. A compound according to claim 8 wherein

R[8] is cyano; and

R[19] and R[20] are hydrogen.

10. A compound according to claim 9 selected from the group consisting of 4-(((2-(1,3-benzodioxol-5-yl)-4-chlorobenzyl)oxy)(1-methyl-1H-imidazol-5-yl)methyl)benzonitrile;

and 4-(((4-chloro-2-(5-formyl-2-thienyl)benzyl)oxy)(1-methyl-1H-imidazol-5-yl)methyl)benzonitrile.

11. A compound according to claim 7 wherein R[3] is aryl.

12. A compound according to claim 11 wherein the aryl is unsubstituted or substituted with one substituent selected from the group consisting of alkanoyl, alkoxy, alkyl, amino, cyano, formyl, halo, and haloalkyl.

13. A compound according to claim 12 wherein

R[18] is cyano; and

R[19] and R[20] are hydrogen.

14. A compound according to claim 13 selected from the group consisting of 4-(((2',5-dichloro(1,1'-biphenyl)-2-yl)methoxy)(1-methyl-1H-imidazol-5-yl)methyl)benzonitrile;

4-(((5-chloro-2'-methyl(1,1'-biphenyl)-2-yl)methoxy)(1-methyl-1H-imidazol-5-yl)methyl)benzonitrile;

4-(((5-chloro-2'-methoxy(1,1'-biphenyl)-2-yl)methoxy)(1-methyl-1H-imidazol-5-yl)methyl)benzonitrile;

4-(((3',5-dichloro(1,1'-biphenyl)-2-yl)methoxy)(1-methyl-1H-imidazol-5-yl)methyl)benzonitrile;

4-(((5-chloro-3'-methyl(1,1'-biphenyl)-2-yl)methoxy)(1-methyl-1H-imidazol-5-yl)methyl)benzonitrile;

4-(((5-chloro-3'-(trifluoromethyl)(1,1'-biphenyl)-2-yl)methoxy)(1-methyl-1H-imidazol-5-yl)methyl)benzonitrile;

4-(((5-chloro-3'-methoxy(1,1'-biphenyl)-2-yl)methoxy)(1-methyl-1H-imidazol-5-yl)methyl)benzonitrile;

4-(((5-chloro-3'-fluoro(1,1'-biphenyl)-2-yl)methoxy)(1-methyl-1H-imidazol-5-yl)methyl)benzonitrile;

4-(((4',5-dichloro(1,1'-biphenyl)-2-yl)methoxy)(1-methyl-1H-imidazol-5-yl)methyl)benzonitrile;

4-(((4-chloro-2-(1-naphthyl)benzyl)oxy)(1-methyl-1H-imidazol-5-yl)methyl)benzonitrile;

4-(((3'-amino-5-chloro(1,1'-biphenyl)-2-yl)methoxy)(1-methyl-1H-imidazol-5-yl)methyl)benzonitrile;

3'-chloro-6'-(((4-cyanophenyl)(1-methyl-1H-imidazol-5-yl)methoxy)methyl)(1,1'-biphenyl)-3-carbonitrile;

4-(((2'-acetyl-5-chloro(1,1'-biphenyl)-2-yl)methoxy)(1-methyl-1H-imidazol-5-yl)methyl)benzonitrile;

4-(((4'-acetyl-5-chloro(1,1'-biphenyl)-2-yl)methoxy)(1-methyl-1H-imidazol-5-yl)methyl)benzonitrile;

4-(((4'-tert-butyl-5-chloro(1,1'-biphenyl)-2-yl)methoxy)(1-methyl-1H-imidazol-5-yl)methyl)benzonitrile;

4-(((5-chloro-3'-ethoxy(1,1'-biphenyl)-2-yl)methoxy)(1-methyl-1H-imidazoi-5-yl)methyl)benzonitrile;

N-(5'-chloro-2'-(((4-cyanophenyl)(1-methyl-1H-imidazol-5-yl)methoxy)methyl)(1,1'-biphenyl)-3-yl)acetamide;

4-(((5-chloro-4'-(trifluoromethyl)(1,1'-biphenyl)-2-yl)methoxy)(1-methyl-1H-imidazol-5-yl)methyl)benzonitrile; and 4-(((5-chloro-3'-formyl(1,1'-biphenyl)-2-yl)methoxy)(1-methyl-1H-imidazol-5-yl)methyl)benzonitrile.

15. A compound according to claim 11 wherein the aryl is substituted with two or three substituents independently selected from the group consisting of alkoxy, alkyl, and halo.

16. A compound according to claim 15 wherein
$R^{18}$ is cyano; and
$R^{19}$ and $R^{20}$ are hydrogen.

17. A compound according to claim 16 selected from the group consisting of 4-(((5-chloro-3∝,4'-dimethyi(1,1'-biphenyl)-2-yl)methoxy)(1-methyl-1H-imidazol-5-yl)methyl)benzonitrile;

4-(((5-chloro-2',5'-dimethoxy(1,1'-biphenyl)-2-yl)methoxy)(1-methyl-1H-imidazol-5-yl)methyl)benzonitrile;

4-(((5-chloro-3',4'-dimethoxy(1,1'-biphenyl)-2-yl)methoxy)(1-methyl-1H-imidazol-5-yl)methyl)benzonitrile;

4-(((5-chloro-3',4',5'-trimethoxy(1,1'-biphenyl)-2-yl)methoxy)(1-methyl-1H-imidazol-5-yl)methyl)benzonitrile;

4-((1-methyl-1H-imidazol-5-yl)((2',3',5-trichloro(1,1'-biphenyl)-2-yl)methoxy)methyl)benzonitrile;

4-((1-methyl-1H-imidazol-5-yl)((3',5,5'-trichloro(1,1'-biphenyl)-2-yl)methoxy)methyl)benzonitrile; and 4-((1-methyl-1H-imidazol-5-yl)((3',4',5-trichloro(1,1'-biphenyl)-2-yl)methoxy)methyl)benzonitrile.

18. A compound according to claim 1 of formula (III)

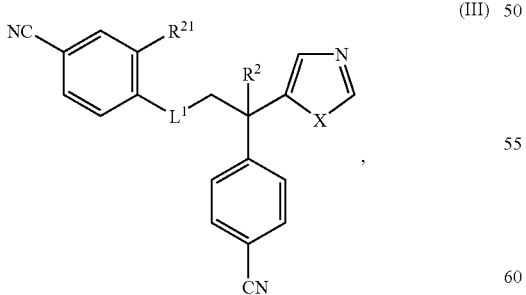

(III)

or a therapeutically acceptable salt thereof, wherein
$L^1$, X, and $R^2$ axe as defined in claim 1; and
$R^{21}$ is selected from the group consisting of aryl and heterocycle wherein the heterocycle may be substituted or unsubstituted and is selected from the group consisting of benzodioxolyl, thiophenyl, quinolinyl, pyridinyl, and dihydropyridinyl.

19. A compound according to claim 18 wherein
$L^1$ is O;
X is $NR^7$; and
$R^2$ is selected from the group consisting of amino, halo and hydroxy.

20. A compound according to claim 19 wherein
$R^2$ is hydroxy; and
$R^{21}$ is aryl.

21. A compound according to claim 20 selected from the group consisting of 6-(2-(4-cyanophenyl)-2-hydroxy-2-(1-methyl-1H-imidazol-5-yl)ethoxy)-3'-methoxy-1,1'-biphenyl-3-carbonitrile;

6-(2-(4-cyanophenyl)-2-hydroxy-2-(1-methyl-1H-imidazol-5-yl)ethoxy)-3',4'-difluoro-1,1'-biphenyl-3-carbonitrile;

6-(2-(4-cyanophenyl)-2-hydroxy-2-(1-methyl-1H-imidazol-5-yl)ethoxy)-4'-(trifluoromethoxy)-1,1'-biphenyl-3-carbonitrile;

3'-chloro-6-(2-(4-cyanophenyl)-2-hydroxy-2-(1-methyl-1H-imidazol-5-yl)ethoxy)-4'-fluoro-1,1'-biphenyl-3-carbonitrile;

6-(2-(4-cyanophenyl)-2-hydroxy-2-(1-methyl-1H-imidazol-5-yl)ethoxy)-3',5'-difluoro-1,1'-biphenyl-3-carbonitrile;

6-(2-(4-cyanophenyl)-2-hydroxy-2-(1-methyl-1H-imidazol-5-yl)ethoxy)-3'-(trifluoromethoxy)-1,1'-biphenyl-3-carbonitrile;

3',4'-dichloro-6-(2-(4-cyanophenyl)-2-hydroxy-2-(1-methyl-1H-imidazol-5-yl)ethoxy)-1,1'-biphenyl-3-carbonitrile;

3',5'-dichloro-6-(2-(4-cyanophenyl)-2-hydroxy-2-(1-methyl-1H-imidazol-5-yl)ethoxy)-1,1'-biphenyl-3-carbonitrile;

6-(2-(4-cyanophenyl)-2-hydroxy-2-(1-methyl-1H-imidazol-5-yl)ethoxy)-3'-fluoro-1,1'-bipbenyl-3-carbonitrile;

3'-chloro-6-(2-(4-cyanophenyl)-2-hydroxy-2-(1-methyl-1H-imidazol-5-yl)ethoxy)-1,1'-biphenyl-3-carbonitrile;

4-(2-(4-cyanophenyl)-2-hydroxy-2-(1-methyl-1H-imidazol-5-yl)ethoxy)-3-(1-naphthyl)benzonitrile; and (S)-6-(2-(4-cyanophenyl)-2-hydroxy-2-(1-methyl-1H-imidazol-5-yl)ethoxy)-4'-(trifluoromethoxy)-1,1'-biphenyl-3-carbonitrile.

22. A compound according to claim 19 wherein
$R^2$ is hydroxy; and
$R^{21}$ is heterocycle wherein the heterocyle may be substituted or unsubstituted and is selected from the group consisting of benzodioxolyl, thiophenyl, quinolinyl, pyridinyl, and dihydropyridinyl.

23. A compound a ccording to claim 22 selected from the group consisting of 3-(1,3-benzodioxol-5-yl)-4-(2-(4-cyanophenyl)-2-hydroxy-2-(1-methyl-1H-imidazol-5-yl)ethoxy)benzonitrile;

4-(2-(4-cyanophenyl)-2-hydroxy-2-(1-methyl-1H-imidazol-5-yl)ethoxy)-3-quinolin-8-ylbenzonitrile; and 4-(2-(4-cyanophenyl)-2-hydroxy-2-(1-methyl-1H-imidazol-5-yl)ethoxy)-3-(2,2-difluoro-1,3-benzodioxol-5-yl)benzonitrile.

24. A compound according to claim 19 wherein
$R^2$ is halo; and
$R^{21}$ is aryl.

25. A compound according to claim 24 selected from the group consisting of
- 6-(2-(4-cyanophenyl)-2-fluoro-2-(1-methyl-1H-imidazol-5-yl)ethoxy)-3'-methoxy-1,1'-biphenyl-3-carbonitrile;
- 6-(2-(4-cyanophenyl)-2-fluoro-2-(1-methyl-1H-imidazol-5-yl)ethoxy)-3',4'-difluoro-1,1'-biphenyl-3-carbonitrile;
- 6-(2-(4-cyanophenyl)-2-fluoro-2-(1-methyl-1H-imidazol-5-yl)ethoxy)-4'-(trifluoromethoxy)-1,1'-biphenyl-3-carbonitrile;
- 3'-chloro-6-(2-(4-cyanophenyl)-2-fluoro-2-(1-methyl-1H-imidazol-5-yl)ethoxy)-4'-fluoro-1,1'-biphenyl-3-carbonitrile;
- 6-(2-(4-cyanophenyl)-2-fluoro-2-(1-methyl-1H-imidazol-5-yl)ethoxy)-3',5'-difluoro1,1'-biphenyl-3-carbonitrile;
- 6-(2-(4-cyanophenyl)-2-fluoro-2-(1-methyl-1H-imidazol-5-yl)ethoxy)-3'-(trifluoromethoxy)-1,1'-biphenyl-3-carbonitrile;
- 3',4'-dichloro-6-(2-(4-cyanophenyl)-2-fluoro-2-(1-methyl-1H-imidazol-5-yl)ethoxy)-1,1'-biphenyl-3-carbonitrile;
- 3',5'-dichloro-6-(2-(4-cyanophenyl)-2-fluoro-2-(1-methyl-1H-imidazol-5-yl)ethoxy)-1,1'-biphenyl-3-carbonitrile;
- 6-(2-(4-cyanophenyl)-2-fluoro-2-(1-methyl-1H-imidazol-5-yl)ethoxy)-3'-fluoro-1,1'-biphenyl-3-carbonitrile; and
- 3'-chloro-6-(2-(4-cyanophenyl)-2-fluoro-2-(1-methyl-1H-imidazol-5-yl)ethoxy)-1,1'-biphenyl-3-carbonitrile.

26. A compound according to claim 19 wherein
$R^2$ is halo; and
$R^{21}$ is heterocycle wherein the heterocycle may be substituted or unsubstituted and is selected from the group consisting of benzodioxolyl, thiophenyl, quinolinyl, pyridinyl, and dihydropyridinyl.

27. A compound according to claim 26 selected from the group consisting of
- 3-(1,3-benzodioxol-5-yl)-4-(2-(4-cyanophenyl)-2-fluoro-2-(1-methyl-1H-imidazol-5-yl)ethoxy)benzonitrile;
- 4-(2-(4-cyanophenyl)-2-fluoro-2-(1-methyl-1H-imidazol-5-yl)ethoxy)-3-quinolin-8-ylbenzonitrile; and
- 4-(2-(4-cyanophenyl)-2-fluoro-2-(1-methyl-1H-imidazol-5-yl)ethoxy)-3-(2,2-difluoro-1,3-benzodioxol-5-yl)benzonitrile.

28. A compound according to claim 19 wherein
$R^2$ is amino; and
$R^{21}$ is aryl.

29. A compound according to claim 28 which is
6-(2-amino-2-(4-cyanophenyl)-2-(1-methyl-1H-imidazol-5-yl)ethoxy)-4'-(trifluoromethoxy)-1,1'-biphenyl-3-carbonitrile.

30. A compound which is
6-(2-(4-cyanophenyl)-2-hydroxy-2-(1-methyl-1H-imidazol-5-yl)ethoxy)-4'-(trifluoromethoxy)-1,1'-biphenyl-3-carbonitrile.

31. A compound which is
6-((2S)-2-(4-cyanophenyl)-2-hydroxy-2-(1-methyl-1H-imidazol-5-yl)ethoxy)-4'-(trifluoromethoxy)-1,1'-biphenyl-3-carbonitrile.

32. A pharmaceutical composition comprising a compound of claim 1 or a therapeutically acceptable salt thereof, in combination with a therapeutically acceptable carrier.

33. A method for reducing tumor size by inhibiting farnesyltransferase in a patient in recognized need of such treatment comprising administering to the patient a therapeutically acceptable amount of a compound of claim 1, or a therapeutically acceptable salt thereof.

34. A method for treating cancer by inhibiting farnesyltransferase in a patient in recognized need of such treatment comprising administering to the patient a therapeutically acceptable amount of a compound of claim 1, or a therapeutically acceptable salt thereof.

* * * * *